(12) United States Patent
Palais et al.

(10) Patent No.: US 8,296,074 B2
(45) Date of Patent: *Oct. 23, 2012

(54) MELTING CURVE ANALYSIS WITH EXPONENTIAL BACKGROUND SUBTRACTION

(75) Inventors: Robert Andrew Palais, Salt Lake City, UT (US); Carl Thomas Wittwer, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 13/271,764

(22) Filed: Oct. 12, 2011

(65) Prior Publication Data

US 2012/0116686 A1  May 10, 2012

Related U.S. Application Data

(63) Continuation of application No. 12/067,642, filed as application No. PCT/US2006/036605 on Sep. 20, 2006, now Pat. No. 8,068,992.

(60) Provisional application No. 60/719,250, filed on Sep. 20, 2005.

(51) Int. Cl.
*G06F 19/00* (2011.01)
*G06F 15/00* (2006.01)
*C12Q 1/68* (2006.01)

(52) U.S. Cl. .................. 702/19; 435/6.1; 700/1
(58) Field of Classification Search .................. None
See application file for complete search history.

(56) References Cited

U.S. PATENT DOCUMENTS

2005/0233335 A1  10/2005  Wittwer et al.
2006/0019253 A1   1/2006  Wittwer et al.

FOREIGN PATENT DOCUMENTS

WO          2004/038038          3/2008

OTHER PUBLICATIONS

Zhou, L. et al., "High-resolution DNA melting analysis for simultaneous mutation scanning and genotyping in solution", Clin. Chem. (2005) 51(10):1770-1777.
Wilhelm, J., et al, Real-time polymerase chain reaction:, ChemBioChem (2003) 4(11):1120-1128.
Wilhelm, J. et al., "SoFAR: software for fully automatic evaluation of real-time PCR data", Biotechniques (2003) 34(2):324-332.
European Patent Office Action for Application No. 06803889.2 dated Aug. 20, 2010 (10 pages).
Duda, Richard O., et al., "Pattern Classification", 2nd ed., New York:Wiley-Interscience, 2001:550-553.
Wittwer, CT, et al., "Nucleic acid techniques", In:Burtis C, Ashwood B, Bruns D eds. Tietz Textbook of Clinical Chemistry and Molecular Diagnostics, 4th Edition, New York, Elsevier, Chapter 37, 2005.
Xiao W, et al., "Denaturing high-performance liquid chromatography: A review", Hum. Mutat 2001: 17:439-74.
Zhou L, et al. "Closed-Tube Genotyping with Unlabeled Oligonucleotide Probes and a Saturating DNA Dye," Clin Chem. 2004;50:1328-35.
Zhou L, et al. "High-resolution DNA melting curve analysis to establish HLA genotypic identity." Tissue Antigens 2004;64:156-64.
Zhou L, et al. "High-resolution DNA melting analysis for simultaneous mutation scanning and genotyping in solution," Clin Chem 2005;51:1770-7.
Abrams E S, et al. "Comprehensive detection of single base changes in human genomic DNA using denaturing gradient gel electrophoresis and a GC clamp." Genomics 1990; 7:463-75.
Bennett C.D., et al. "The lightertyper: high-throughput genotyping using fluorescent melting curve analysis." biotechniques Jun. 2003; 34: 1288-1295.
Bernard PS, et al. "Homogeneous multiplex genotyping of hemochromatosis mutations with fluorescent hybridization probes." Am J Pathol 1998; 153:1055-61.
Bobadilla JL, et al. "Cystic fibrosis: A worldwide analysis of CFTR mutations—correlation with incidence data and application to screening." Hum Mutat 2002; 14:575-606.
Breslauer KJ, et al. "Predicting DNA duplex stability from the base sequence." Proc Natl Acad Sci USA 1986; 83:3746-50.
Carmody MW, et al. "Inhibition of DNA hybridization following partial dUTP substitution." BioTechniques 1993;15:692-9.
Chou LS, et al. "Unlabeled oligonucleotide probes modified with locked nucleic acids for improved mismatch discrimination in genotyping by melting analysis." Biotechniques 2005; 39: 644-50.
Cradic KW, et al. "Substitution of 3'-phosphate cap with a carbon-based blocker reduces the possibility of fluorescence resonance energy transfer probe failure in real-time PCR assays." Clin Chem 2004; 50: 1080-2.
Crockett, AO, et al. "Fluorescein-labeled oligonucleotides for real-time pcr: using the inherent quenching of deoxyguanosine nucleotides. "Anal. Biochem. 2001; 290:89-97. De Kok JB, et al. "Rapid genotyping of single nucleotide polymorphisms using novel minor groove binding DNA oligonucleotides (MGB probes)." Hum Mutat 2002; 19:554-9.
Dobrowolski SF, et al. "Validation of dye-binding/high-resolution thermal denaturation for the identification of mutations in the SLC22A5 gene." Hum Mutat 2005; 25:306-13.
Graham R, Liew M, Meadows C, Lyon E, Wittwer CT. Distinguishing different DNA heterozygotes by high-resolution melting. Clin Chem 2005; 51.
Gundry CN, et al. "Rapid F508del and F508C assay using fluorescent hybridization probes." Genet Test 1999; 3:365-70.
Gundry, C N. et al, "Amplicon Melting Analysis with Labeled Primers: A Close-Tube Method for Differentiating Homozygotes and Heterozygotes," Clinical Chemistry (2003), 49(3):396-406.
Herrmann MG, et al. "Rapid beta-globin genotyping by multiplexing probe melting temperature and color." Clin Chem 2000;46:425-8.
Herrmann MG, et al. "DNA melting analysis for mutation scanning and genotyping: a cross platform comparison." Clin Chem 2006; 52: 494-503.

(Continued)

*Primary Examiner* — John S Brusca
(74) *Attorney, Agent, or Firm* — Barnes & Thornburg LLP

(57) ABSTRACT

A method for clustering melting profiles of a plurality of nucleic acid samples, comprising measuring the fluorescence of each nucleic acid sample as a function of temperature to produce a respective raw melting curve for each respective nucleic acid sample, and clustering genotypes of the plurality of nucleic acid samples to form a plurality of clusters of melting curves. A system for analyzing a plurality of nucleic acid samples comprising an instrument for sequentially heating fluorescently detectable complexes while monitoring their fluorescence, a central processing unit (CPU) for performing computer executable instructions, and a memory storage device for storing computer executable instructions that when executed by the CPU cause the CPU to cluster genotypes of a plurality of nucleic acid samples.

36 Claims, 34 Drawing Sheets

OTHER PUBLICATIONS

Jobs M, et al. "DASH-2: flexible, low cost, and high-throughput SNP genotyping by dynamic allele-specific hybridization on membrane arrays." Genome Res 2003; 13: 916-24.

Lay M J, et al. "Real-time fluorescence genotyping of factor V Leiden during rapid-cycle PCR." Clin. Chem. 1997;43:2262-7.

Leber M, et al. "A fractional programming approach to efficient DNA melting temperature calculation." Oxford Press 2005; 21: 2375-82.

Lee LG, et al. "Allelic discrimination by nick-translation PCR with fluorogenic probes." Nucleic Acids Res 1993;21:3761-6. 1993;21:3761-6.

Liew M, et al. "Genotyping of single-nucleotide polymorphisms by high-resolution melting of small amplicons." Clin Chem 2004; 50:1156-64.

Liew M, et al. "Genotyping of human platelet antigens 1-6 and 15 by high-resolution amplicon melting and conventional hybridization probes," J Mol Diag, 2006;8:97-104.

Margraf R, et al. "Masking Selected Sequence Variation by Incorporating Mismatches Into Melting Analysis Probes." Wiley Interscience 2006; 27(3): 269-78.

Marras SA, et al. "Genotyping SNPs with molecular beacons." Methods Mol Biol. 2003; 212:111-28.

McKinney JT, et al. "Rapid, comprehensive screening of the human medium chain acyl-CoA dehydrogenase gene." Mol Genet Metab 2004; 82:112-20.

Millward H, et al. "Homogeneous amplification and mutation scanning of the p53 gene using fluorescent melting curves." Clin Chem 2002; 48:1321-8.

Nataraj A J, et al. "Single-strand conformation polymorphism and heteroduplex analysis for gel-based mutation detection." Electrophoresis 1999; 20:1177-85.

Orita M, et al. "Detection of polymorphisms of human DNA by gel electrophoresis as single-strand conformation polymorphisms." Proc Natl Acad Sci USA 1989; 86:2766-70.

Peyret N, et al. "Nearest-neighbor thermodynamics and NMR of DNA sequences with internal A.A, C.C, G.G, and T.T mismatches." Biochemistry 1999; 38:3468-77.

Prince JA, et al. "Robust and accurate single nucleotide polymorphism genotyping by dynamic allele-specific hybridization (DASH); design criteria and assay validation." Genome Res 2001; 11: 152-62.

PCT International Search Report and Written Opinion for related PCT/US06/36605 (Sep. 20, 2006).

PCT International Preliminary Report on Patentability for related PCT/US06/36605 (Sep. 20, 2006).

Plambeck J, "How Temperture Affects Chemical Equilibria." Chemical Sciences 1996; 1-4, Retrieved from Internet , http://www.valberta.ca/~iplambec/che/pl02/P02062.html.

Reed GH, et al. "Sensitivity and specificity of single-nucleotide polymorphism scanning by high-resolution melting analysis." Clin Chem 2004; 50:1748-54.

Ririe KM, et al. "Product differentiation by analysis of DNA melting curves during the polymerase chain reaction," Anal Biochem 1997; 245:154-60.

Ross PD, et al. "The thermodynamic contribution of the 5-methyl group of thymine in the two- and three-stranded complexes formed by poly(dU) and poly(dT) with poly(dA)." Biopolymers 2003;68:210-22.

Santalucia J, "A unified view of polymer, dumbbell, and oligonucleotide DNA nearest-neighbor thermodynamics." Proc Natl Acad Sci USA 1998; 95: 1460-5.

Santalucia J, "The use of spectroscopic techniques in the study of DNA stability." Oxford Press, New York 2000;329-56.

Santalucia J, et al. "The thermodynamics of DNA structural motifs." Annu Rev Biophys Struct 2004; 33: 415-40.

Silvestrini R, et al. "Quality Control for Evaluation of the S-Phase Fraction by Flow Cytometry: A Multicentric Study" Cytometry 1994; 18: 11-16.

Taylor G R, et al. "Enzymatic methods for mutation scanning." Genet. Anal. 1999; 14:181-6.

Von Ahsen N, et al. "oligonucleotide melting temperatures under pcr conditions:" Clin Chem 2001; 47: 1956-61.

Wang JK, et al. "High-throughput SNP genotyping by single-tube PCR with t,-shift primers." Biotechniques 2005; 39:885-93.

Wartell R M, et al., "Detecting single base substitutions, mismatches and bulges in DNA by temperature gradient gel electrophoresis and related methods." J Chromatogr A 1998; 806:169-85.

Whitcombe D, et al. "Detection of PCR products using self-probing amplicons and fluorescence." Nat Biotechnol 1999; 17:804-7.

Willmore C, et al. "Detection of c-kit-activating mutations in gastrointestinal stromal tumors by high-resolution amplicon melting analysis." Am J Clin Pathol 2004; 122:206-16.

Wittwer CT, et al. "Continuous fluorescence monitoring of rapid cycle DNA amplification." Biotechniques 1997; 22:130-1, 134-8.

Wittwer CT, et al. "Real-time multiplex PCR assays." Methods 2001;25:430-42.

Wittwer CT, et al. "High-resolution genotyping by amplicon melting analysis using LCGreen." Clin Chem 2003;49:853-60.

Wittwer CT, et al. "Diagnostic molecular microbiology; principles and applications." Washington DC: ASM Press, 2004:71-84.

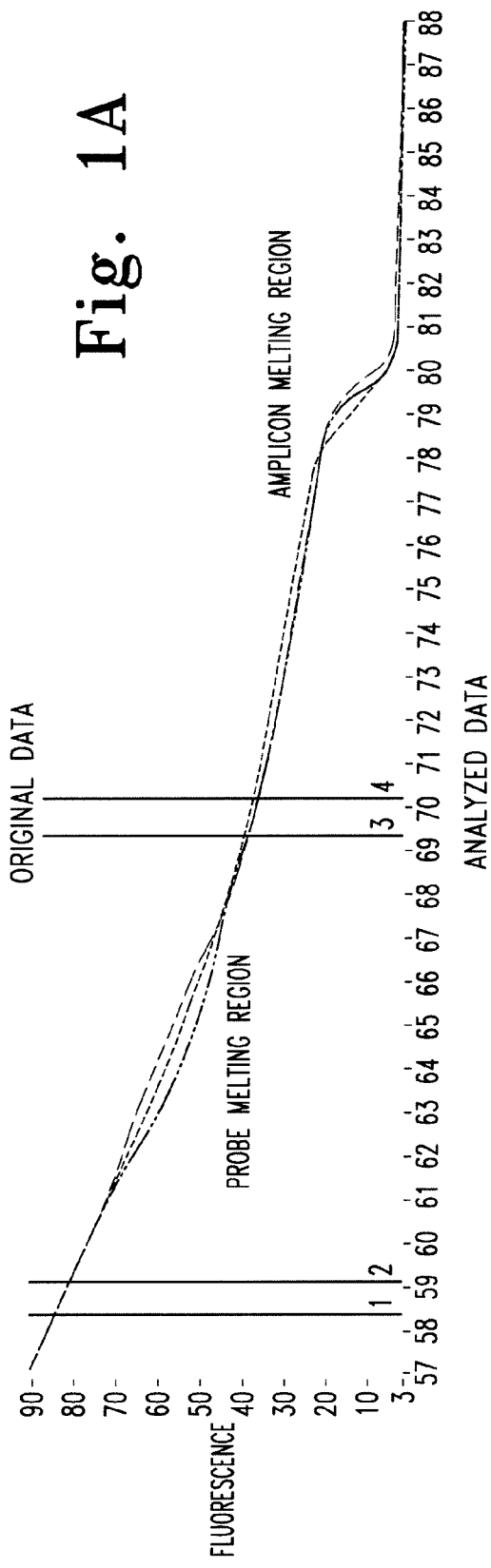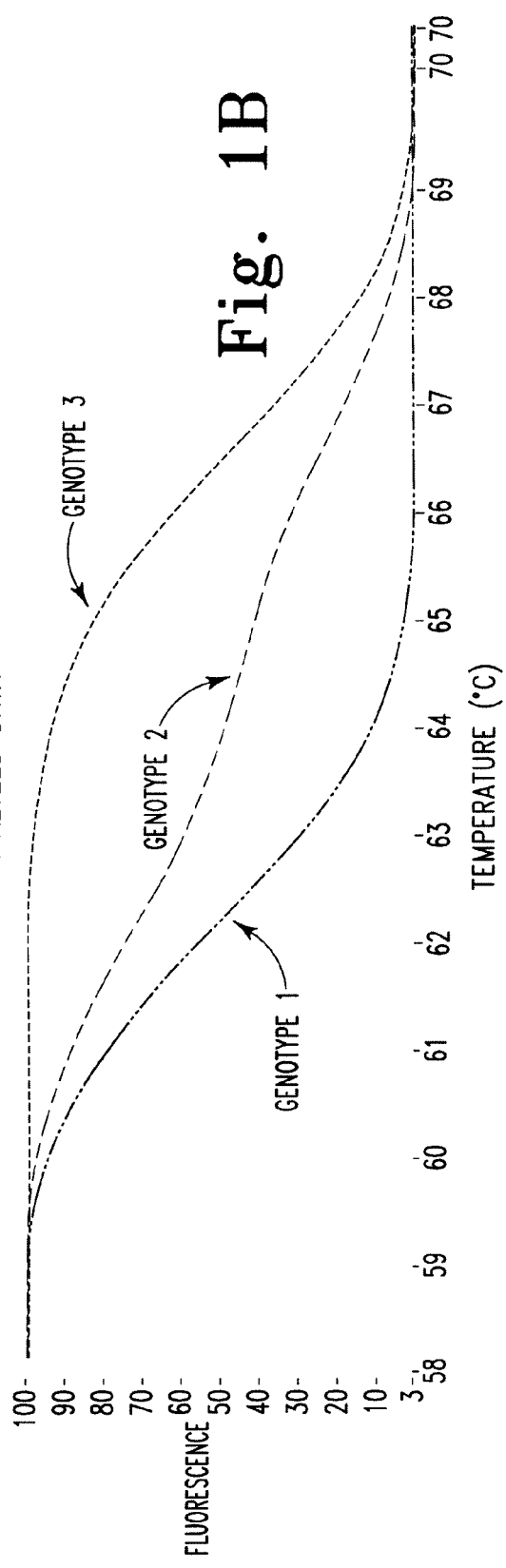

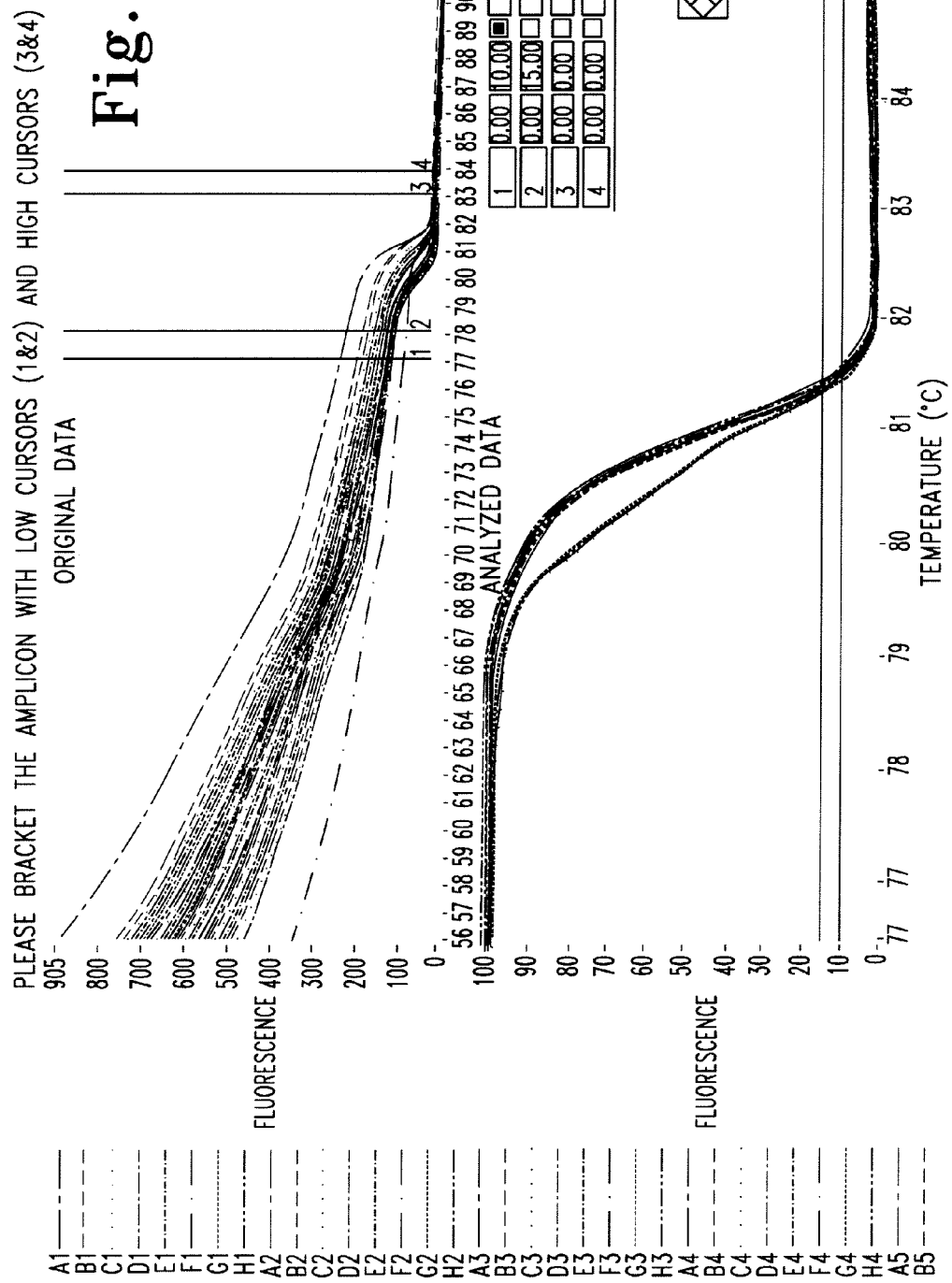

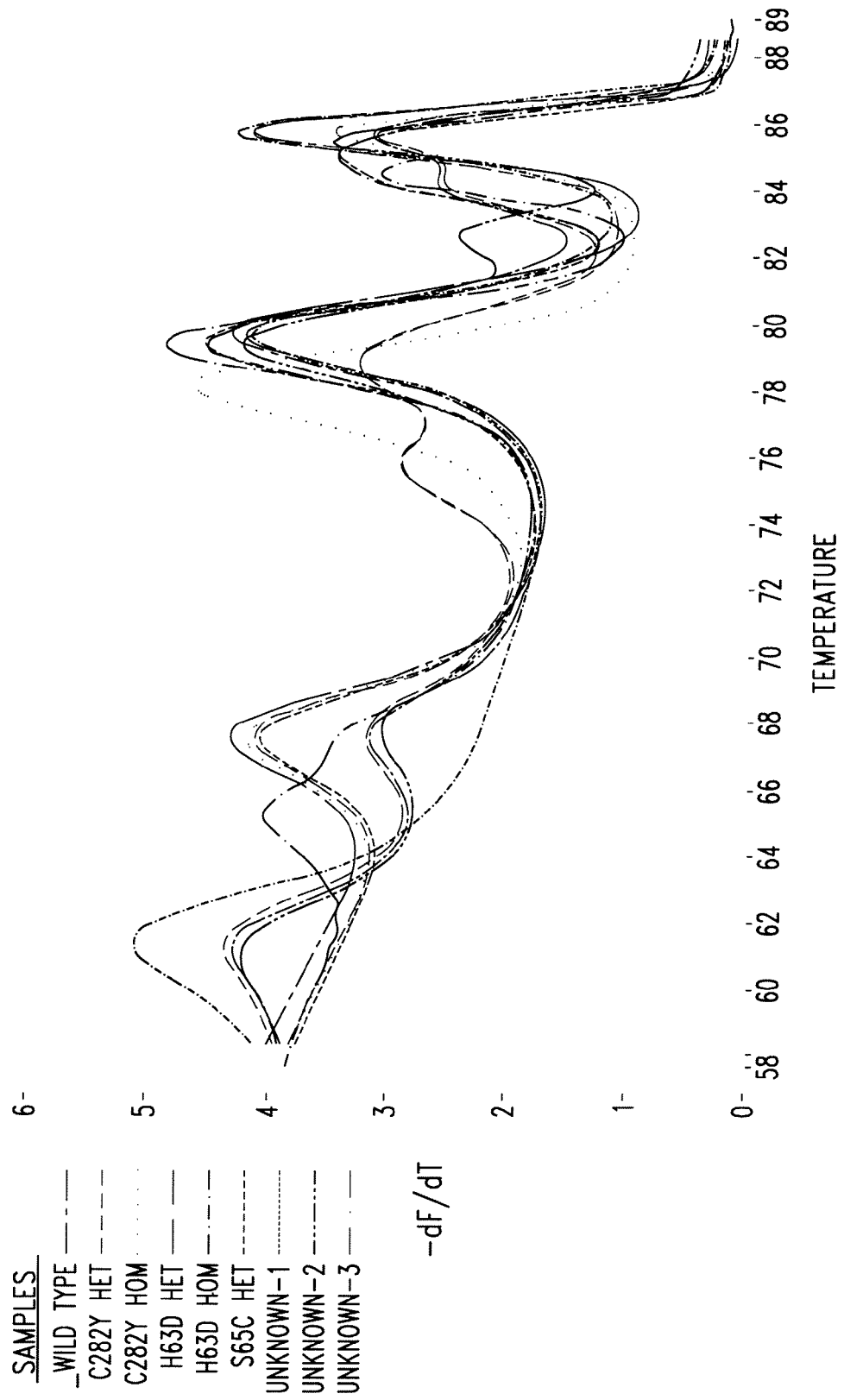

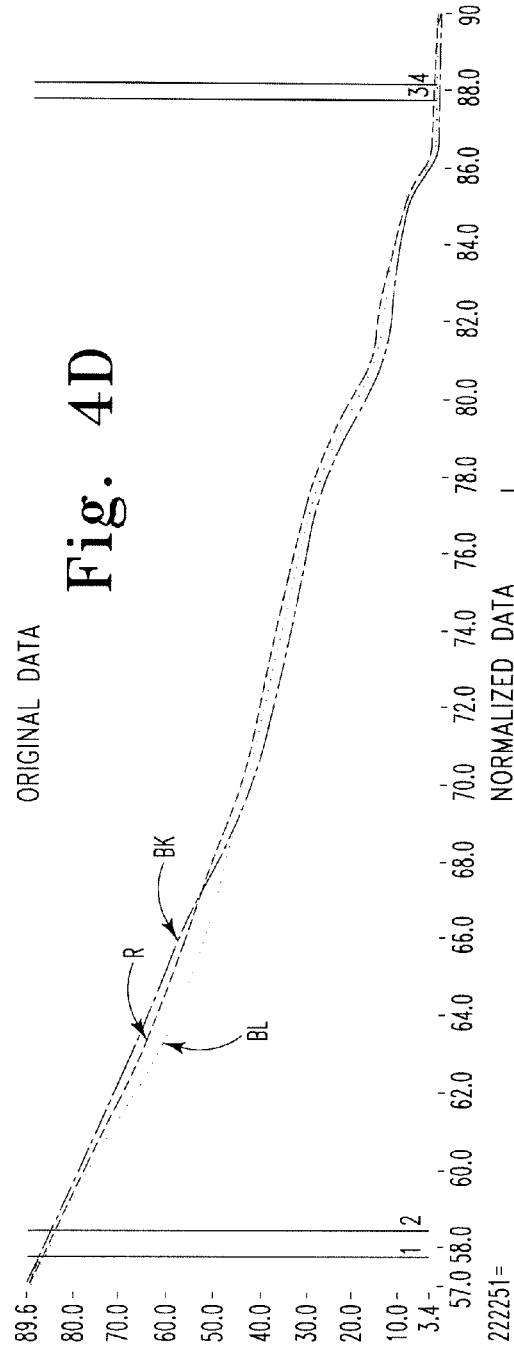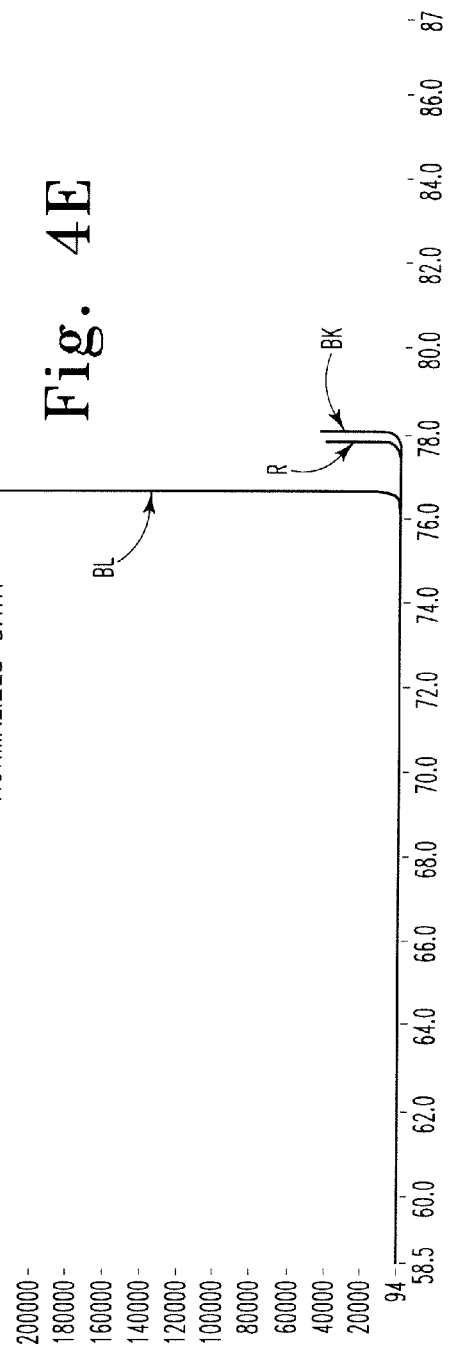

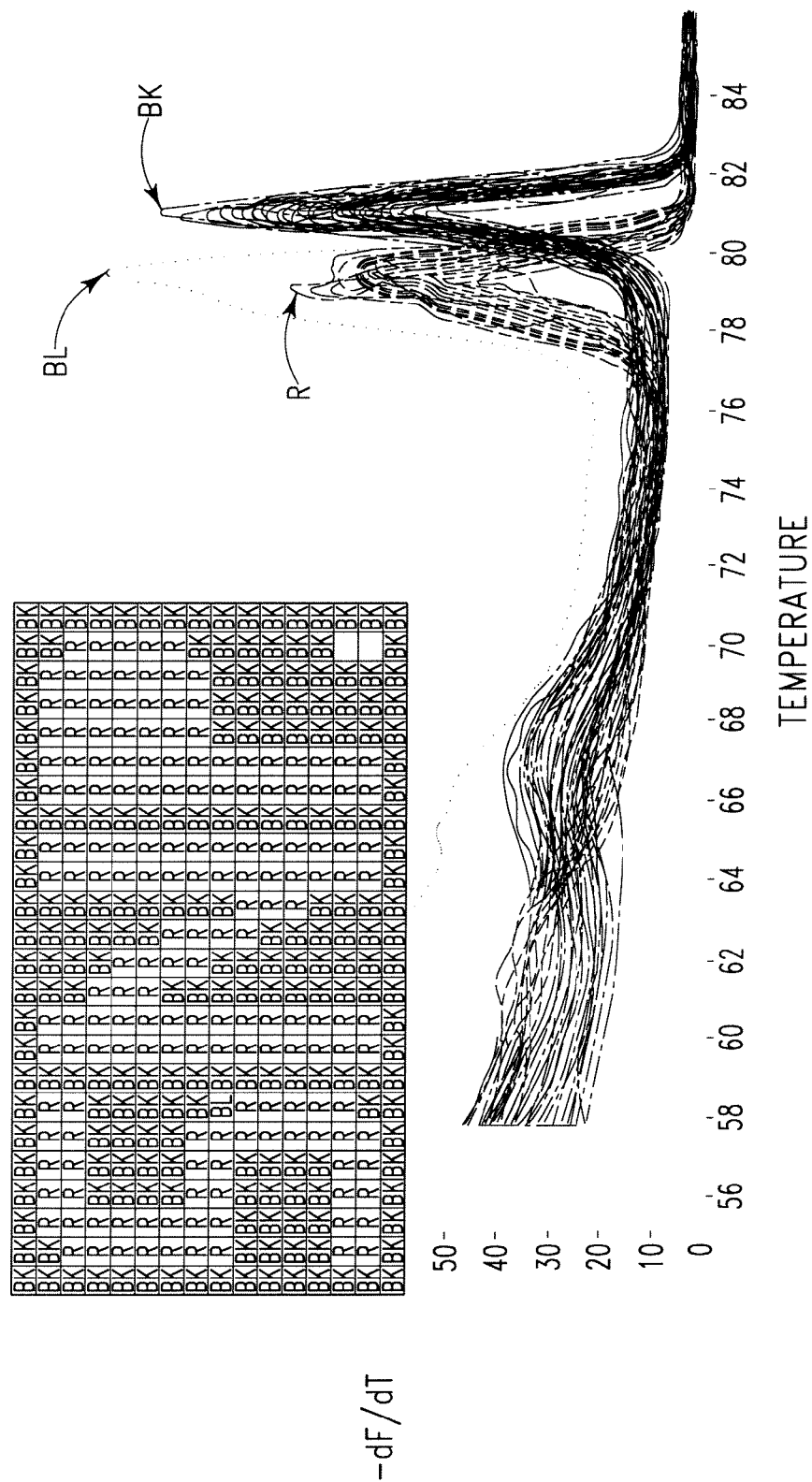

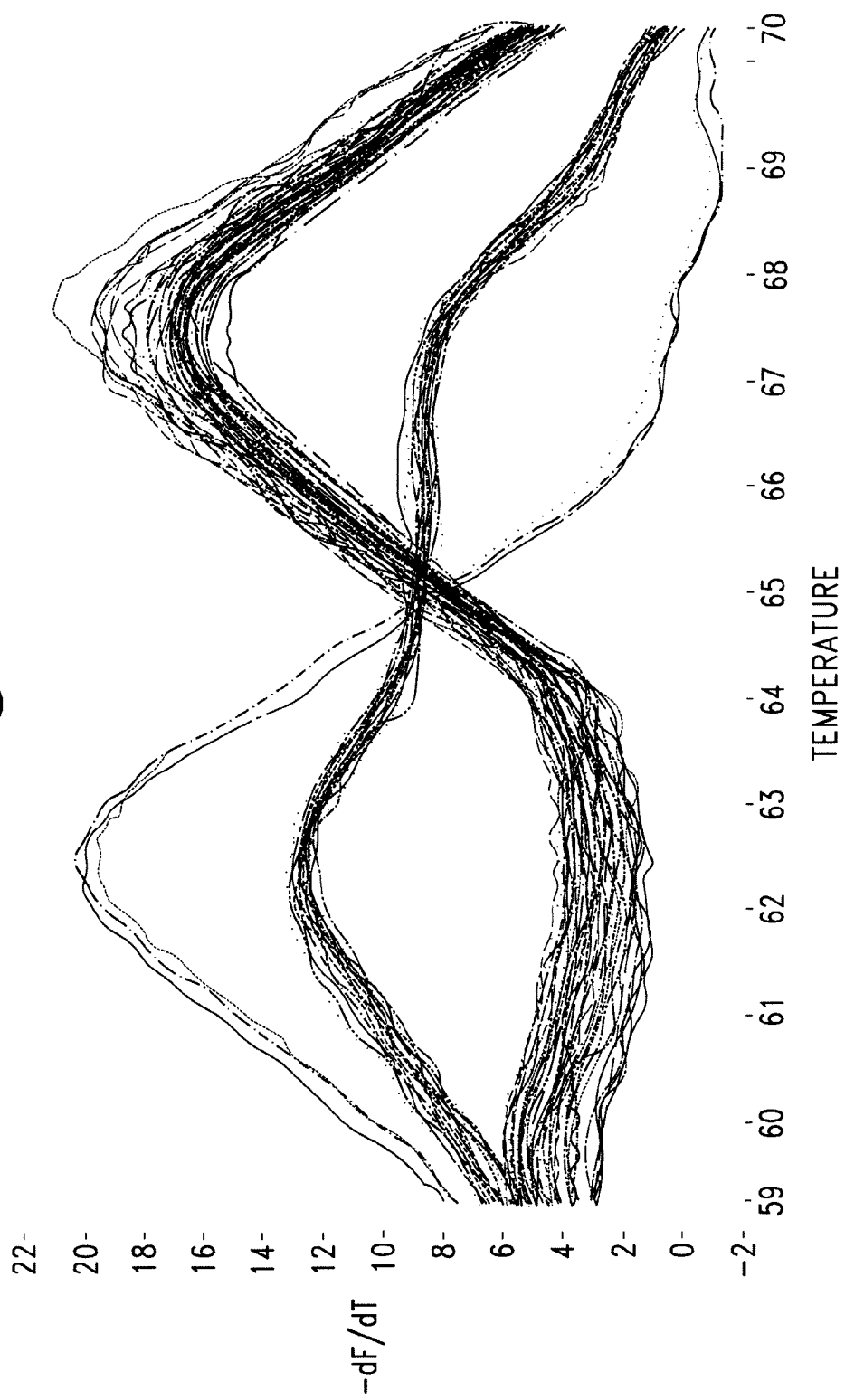

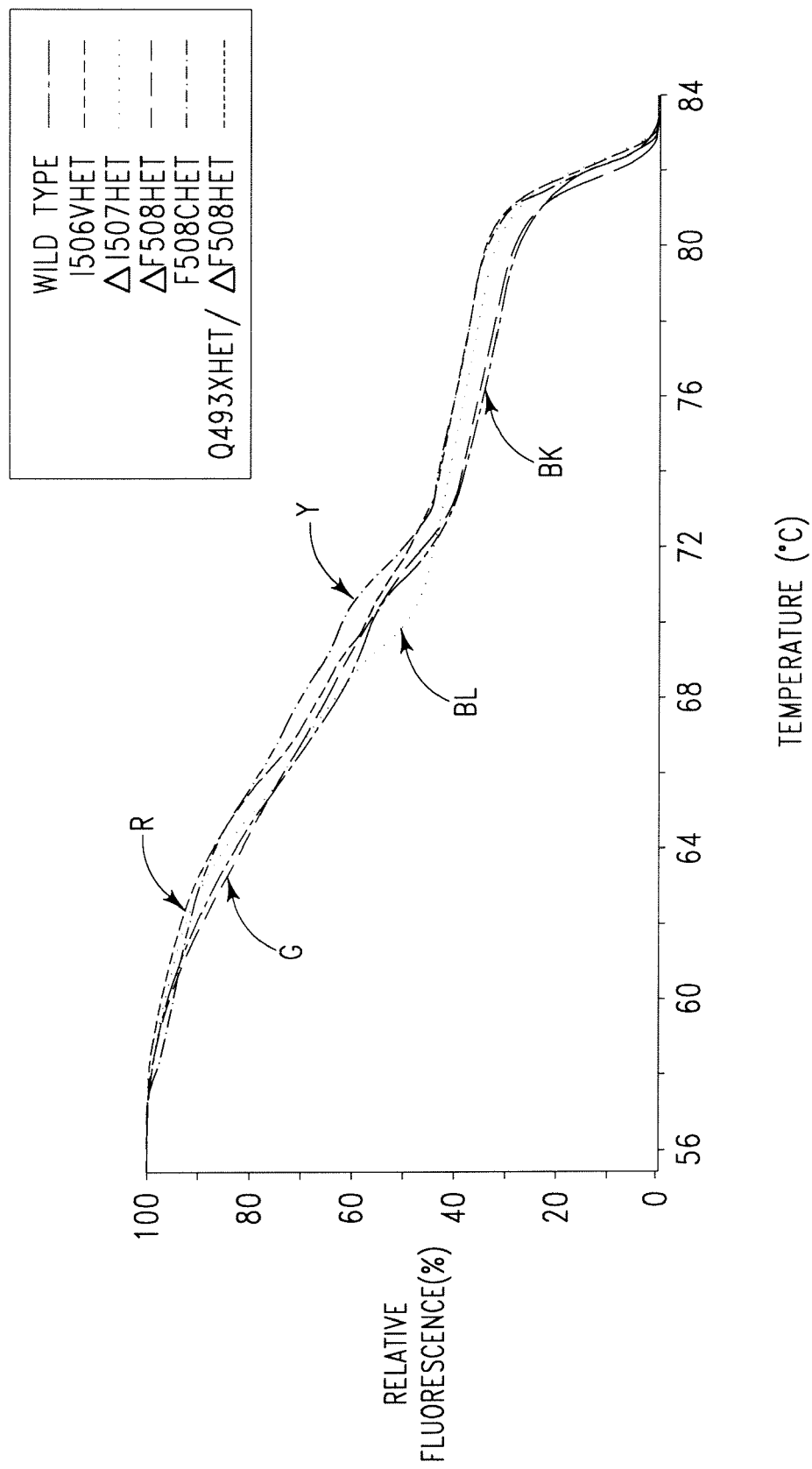

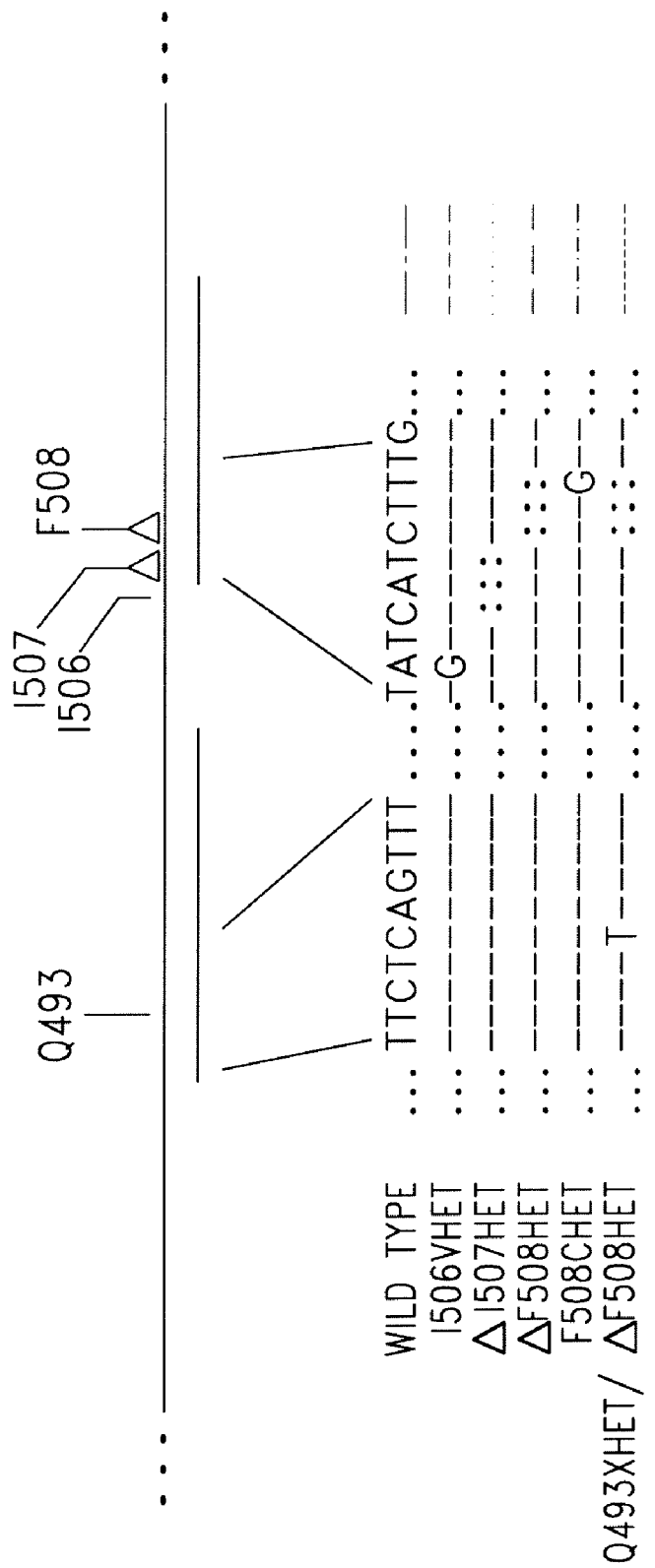

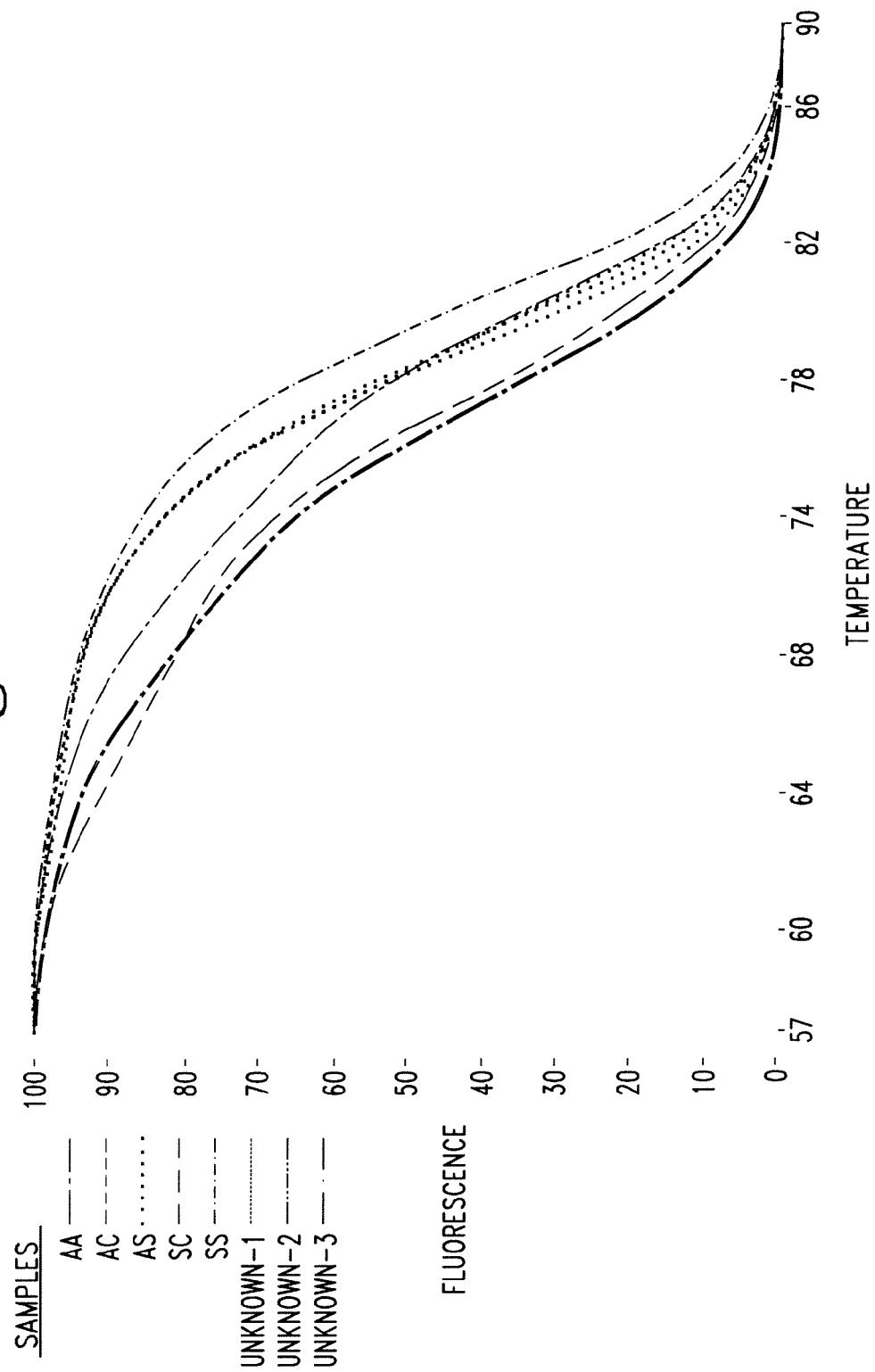

SEQUENCE LISTING

```
<160> NUMBER OF SEQ ID NOS: 9

<210> SEQ ID NO 1
<211> LENGTH: 100
<212> TYPE: DNA
<213> ORGANISM: Homo sapiens

<400> SEQUENCE: 1
ctgaaaggtt acttcaagga caaaatacct gtattcctcg cctgtccagg gatctgctct     60
tacagattag aagtagtcct attagcccag aggcgatgtc                          100

<210> SEQ ID NO 2
<211> LENGTH: 21
<212> TYPE: DNA
<213> ORGANISM: Homo sapiens

<400> SEQUENCE: 2
ctgaaaggtt acttcaagga c                                               21

<210> SEQ ID NO 3
<211> LENGTH: 15
<212> TYPE: DNA
<213> ORGANISM: Homo sapiens
```

```
-continued

<400> SEQUENCE: 3
gacatcgcct ctggg                                                          15

<210> SEQ ID NO 4
<211> LENGTH: 22
<212> TYPE: DNA
<213> ORGANISM: Homo sapiens

<400> SEQUENCE: 4 tggacataaggagcggacaggt                                                    22

<210> SEQ ID NO 5
<211> LENGTH: 10
<212> TYPE: DNA
<213> ORGANISM: Homo sapiens

<400> SEQUENCE: 5
tcttggagaa                                                                10

<210> SEQ ID NO 6
<211> LENGTH: 10
<212> TYPE: DNA
<213> ORGANISM: Homo sapiens

<400> SEQUENCE: 6
aggtcaacga                                                                10

<210> SEQ ID NO 7
<211> LENGTH: 10
<212> TYPE: DNA
<213> ORGANISM: Homo sapiens

<400> SEQUENCE: 7
ttctcagttt                                                                10

<210> SEQ ID NO 8
<211> LENGTH: 11
<212> TYPE: DNA
<213> ORGANISM: Homo sapiens

<400> SEQUENCE: 8
tatcatcttt g                                                              11

<210> SEQ ID NO 9
<211> LENGTH: 45
<212> TYPE: DNA
<213> ORGANISM: Homo sapiens

<400> SEQUENCE: 9
ccatggtgca cctgactcct gaggagaagt ctgccgttac tgccc                         45
```

MELTING CURVE ANALYSIS WITH EXPONENTIAL BACKGROUND SUBTRACTION

CROSS REFERENCE TO RELATED APPLICATION

This application is a continuation of U.S. Ser. No. 12/067,642 filed Mar. 20, 2008, now U.S. Pat. No. 8,068,992. U.S. Ser. No. 12/067,642 is the U.S. national phase of PCT/US2006/036,605 filed Sep. 20, 2006. PCT/US2006/036,605 claims the benefit of the Sep. 20, 2005 filing date of U.S. Ser. No. 60/719,250. All of U.S. Ser. No. 12/067,642, PCT/US2006/036,605 and U.S. Ser. No. 60/719,250 are hereby incorporated by reference herein.

FIELD OF THE INVENTION

Generally the present invention relates to nucleic acid melting curve analysis. More specifically various embodiments of the present invention relate to methods and systems for analyzing the melting profiles of double stranded nucleic acids by removing the background fluorescence signals.

BACKGROUND OF THE INVENTION

Methods for analyzing DNA sequence variation can be divided into two general categories: 1) genotyping for known sequence variants and 2) scanning for unknown variants. There are many methods for genotyping known sequence variants, and single step, homogeneous, closed tube methods that use fluorescent probes are available (Lay M J, et al., Clin. Chem 1997; 43:2262-7). In contrast, most scanning techniques for unknown variants require gel electrophoresis or column separation after PCR. These include singlestrand conformation polymorphism (Orita O, et al., Proc Natl Acad Sci USA 1989; 86:2766-70), heteroduplex migration (Nataraj A J, et al., Electrophoresis 1999; 20:1177-85), denaturing gradient gel electrophoresis (Abrams E S, et al., Genomics 1990; 7:463-75), temperature gradient gel electrophoresis (Wartell R M, et al., J Chromatogr A 1998; 806:169-85), enzyme or chemical cleavage methods (Taylor G R, et al., Genet Anal 1999; 14:181-6), as well as DNA sequencing. Identifying new mutations by sequencing also requires multiple steps after PCR, namely cycle sequencing and gel electrophoresis. Denaturing high-performance liquid chromatography (Xiao W, et al., Hum Mutat 2001; 17:439-74) involves injecting the PCR product into a column.

Single nucleotide polymorphisms (SNPs) are by far the most common genetic variations observed in man and other species. In these polymorphisms, only a single base varies between individuals. The alteration may cause an amino acid change in a protein, alter rates of transcription, affect mRNA spicing, or have no apparent effect on cellular processes. Sometimes when the change is silent (e.g., when the amino acid it codes for does not change), SNP genotyping may still be valuable if the alteration is linked to (associated with) a unique phenotype caused by another genetic alteration.

There are many methods for genotyping SNPs. Most use PCR or other amplification techniques to amplify the template of interest. Contemporaneous or subsequent analytical techniques may be employed, including gel electrophoresis, mass spectrometry, and fluorescence. Fluorescence techniques that are homogeneous and do not require the addition of reagents after commencement of amplification or physical sampling of the reactions for analysis are attractive. Exemplary homogeneous techniques use oligonucleotide primers to locate the region of interest and fluorescent labels or dyes for signal generation. Various PCR-based methods are completely closed-tubed, using a thermostable enzyme that is stable to DNA denaturation temperature, so that after heating begins, no additions are necessary.

Several closed-tube, homogeneous, fluorescent PCR methods are available to genotype SNPs. These include systems that use FRET oligonucleotide probes with two interacting chromophores (adjacent hybridization probes, TaqMan® probes, Molecular Beacons, Scorpions), single oligonucleotide probes with only one fluorophore (Gquenching probes, Crockett, A. O. and C. T. Wittwer, Anal. Biochem. 2001; 290:89-97 and SimpleProbes®, Idaho Technology), and techniques that use a dsDNA dye instead of covalent, fluorescently-labeled oligonucleotide probes.

PCR methods that monitor DNA melting with dsDNA fluorescent dyes have become popular in conjunction with real-time PCR. Because PCR produces enough DNA for fluorescent melting analysis, both amplification and analysis can be performed in the same tube, providing a homogeneous, closed-tube system that requires no processing or separation steps. dsDNA dyes are commonly used to identify products by their melting temperature, or $T_m$.

The power of DNA melting analysis depends on its resolution. Studies with UV absorbance often required hours to collect high-resolution data at rates of 0.1-1.0° C./min to ensure equilibrium. In contrast, fluorescent melting analysis is often acquired at 0.1-1.0° C./sec and resolution is limited to 2-4 points/° C. With recent advances in electronics (e.g., 24-bit A-to-D converters), high-resolution melting can be performed rapidly with 10-100 times the data density (50-100 points/° C.) of conventional real-time PCR instruments, as recently demonstrated for probe and PCR product melting. Furthermore, saturating DNA dyes, such as LCGreen® Plus (Idaho Technology, Salt Lake City, Utah), that maximize detection of mismatched duplexes (heteroduplexes) are now available (see, e.g. U.S. Patent Publication Nos. 2005/0233335 and 2006/0019253, herein incorporated by reference in their entireties). These two developments dramatically increase the power of fluorescence-based DNA melting for robust identification of single-base changes within PCR products.

High-resolution melting analysis for gene scanning relies primarily on the shape of the melting transition of the PCR products. An available method for screening for heterozygous single nucleotide polymorphisms (SNPs) within products up to 1,000 bp has a sensitivity and specificity of 97% and 99%, respectively. In many cases, high-resolution analysis of the melting transition also allows genotyping without probes. Even greater specificity for variant discrimination over a smaller region can be obtained by using unlabeled probes. Specific genotypes are inferred by correlating sequence alterations under the probe to changes in the probe $T_m$. With the recent advances with dyes and instrumentation, high-resolution gene scanning and genotyping with unlabeled probes can optionally be done simultaneously in the same reaction. Both PCR product and probe melting transitions may be observed in the presence of a saturating DNA dye. In addition to screening for any sequence variant between the primers in the PCR product, common polymorphisms and mutations can be genotyped. Furthermore, unbiased, hierarchal clustering can accurately group the melting curves into genotypes. One, two, or even more unlabeled probes can be used in a single PCR.

In simultaneous genotyping and scanning, product melting analysis detects sequence variants anywhere between two primers, while probe melting analysis identifies variants under a probe. If a sequence variant is between the primers and under a probe, both the presence of a variant and its genotype are obtained. If product melting indicates a variant but the probe does not, then the variation likely occurs between the primers but not under the probe, and further analysis for genotyping is necessary. Probes can be placed at sites of common sequence variation so that in most cases, if product scanning is positive, the probes will identify the sequence variants, greatly reducing the need for sequencing. With one probe, the genotype of an SNP can be established by both PCR product and probe melting. With two probes, two separate regions of the sequence can be interrogated for genotype and the rest of the PCR product scanned for rare sequence variants. Multiple probes can be used if they differ in melting temperature and if each allele presents a unique pattern of probe and/or product melting.

In one illustrative example, a population is screened for cystic fibrosis mutations. Since only 3.8% of Caucasians are cystic fibrosis carriers, one would expect 96.2% of randomly screened individuals to be negative by complete (exon and splice site) sequencing. With 27 exons, the percentage of sequencing runs expected to be positive is less than 0.14%. That is, only about 1 in 1000 sequencing runs would be useful. This is why sequencing is not recommended for cystic fibrosis screening. Instead, a selected mutation panel is usually performed that detects 83.7% of cystic fibrosis alleles.

Alternatively, consider simultaneous scanning and genotyping for cystic fibrosis screening by high-resolution melting. If the amplicon length is kept under 400 bp, the sensitivity of high-resolution scanning approaches 100.0%. If common mutations and polymorphisms are analyzed with unlabeled probes in the same reaction, then about 80% of mutations will also be genotyped. Compared to screening by de novo sequencing, the sequencing burden can be reduced by 99.97%.

Closed-tube genotyping methods that use melting analysis have the capacity to scan for unexpected variants. Melting methods also use less complex and fewer probes than allele specific methods that require one probe for each allele analyzed. Allele discrimination by $T_m$ or curve shape is an interesting option to fluorescent color. Dyes that generically stain double-stranded DNA are attractive for simplicity and cost. Although the reliability of genotyping by amplicon melting is controversial, a recent study found that 21 out of 21 heteroduplex pairs tested were distinguishable by high-resolution melting of small amplicons (Graham R, Liew M, Meadows C, Lyon E, Wittwer C T. Distinguishing different DNA heterozygotes by high-resolution melting. Clin Chem 2005; 51).

Although common sequence variants can usually be genotyped with one or two unlabeled probes in the same reaction, more than two probes and/or sequential reactions can also be used. For example, multiple overlapped probes can locate unexpected rare variants to within the region covered by one probe. Additional probes can be designed to identify the exact position and sequence of the variation. However, DNA sequencing is a more direct approach for identifying new, previously unknown variations, particularly when the amplified region is highly variable. Nevertheless, in the vast majority of genetic analysis, the amplified wild type sequence is known and potential common variants are limited. In these cases, scanning and genotyping can be performed in one step by DNA melting with simple oligonucleotides. No fluorescent probes or separations are required, and both amplification (15 min) and melting analysis (1-2 min) can be rapid.

As discussed above, simultaneous genotyping and scanning, as well as other genotyping techniques that employ melting analysis have been promising areas of research. However, the melting curve analysis prior to high-resolution capabilities provided a lack of specificity and accuracy. With the advent of high-resolution melting curve analysis, background fluorescence noise can interfere with the use of melting curves to accurately genotype SNPs, detect sequence variations, and detect mutations. Depending on the amplicon, previous background fluorescence removal techniques have led to some erroneous calls. By example, the baseline technique uses linear extrapolation as a method for normalizing melting curves and removing background fluorescence. This technique works well with labeled probes. However, this and other previous normalization techniques have not worked as well with unlabeled probes (Zhou L, Myers A N, Vandersteen J G, Wang L, Wittwer C T. Closed-Tube Genotyping with Unlabeled Oligonucleotide Probes and a Saturating DNA Dye. Clin Chem. 2004; 50:1328-35) multiplex small amplicon melting (Liew M, Nelson L, Margraf R, Mitchell S, Erali M, Mao R, Lyon E, Wittwer C T. Genotyping of human platelet antigens 1-6 and 15 by high-resolution amplicon melting and conventional hybridization probes. J Mol Diag, 2006; 8:97-104) and combined amplicon and unlabeled probe melting (Zhou L, Wang L, Palais R, Pryor R, Wittwer C T). High-resolution melting analysis for simultaneous mutation scanning and genotyping in solution. Clin Chem 2005; 51:1770-7, hereby incorporated by reference), nor do they work as well for small amplicons. At least in part, this is because unlabeled probe and small amplicon melting methods often require background subtraction at lower temperatures (40-80° C.) then is usual for standard amplicon melting at 80-95° C. At these lower temperatures, the low temperature baseline is not linear, but a curve with rapidly increasing fluorescence at low temperatures. When linear extrapolation is used, the lines can intersect before the melting transition is complete, and when this occurs the previous techniques do not provide the most accurate means for melting curve analysis, in part due to their mathematical reliance on absolute fluorescence.

It would be advantageous for a system and method to genotype SNPs, detect sequence variations, and/or detect mutations with high accuracy in double stranded nucleic acids through use of high resolution melting profile techniques. It would be further advantageous if the background fluorescence could be automatically and accurately separated from a double stranded nucleic acid sample melting profile. It would be a further advantage if the system and method performed accurate melting curve analysis for small and large amplicons, as well as with unlabeled probes.

SUMMARY OF THE INVENTION

According to an aspect of the invention, a method is provided for clustering melting profiles of a plurality of nucleic acid samples. Each respective sample comprises a respective nucleic acid and a molecule that binds the respective nucleic acid to form a respective fluorescently detectable complex. The method comprises measuring the fluorescence of each nucleic acid sample as a function of temperature to produce a respective raw melting curve for each respective nucleic acid sample, and clustering genotypes of the plurality of nucleic acid samples to form a plurality of clusters of melting curves. The clustering is hierarchically achieved upon assigning a distance between each pair of melting profiles.

Illustratively according to this aspect, the method further comprises normalizing the raw melting curves.

Illustratively according to this aspect, the distance assigned is based on a distance metric selected from the group consisting of: the maximal distance between curves; the average of the absolute value of the distance between curves at all temperature points; and, the average of the root mean square of the distance between curves at all temperature points.

Illustratively according to this aspect, the number of clusters is determined automatically by selecting a maximum ratio of distances between adjacent cluster levels.

Illustratively according to this aspect, accuracy of the number of clusters is obtained by ordering the ratios of distances between each two adjacent cluster levels.

Illustratively according to this aspect, a distance between clusters is determined as the minimum distance between any two curves in each cluster.

Illustratively according to this aspect, each respective raw melting curve comprises a respective background fluorescence signal and a respective nucleic acid sample signal. The respective background signals are separated from the respective nucleic acid sample signals by use of an exponential algorithm to generate respective corrected melting curves. The respective corrected melting curves comprise the respective nucleic acid sample signals.

Illustratively according to this aspect, each respective background signal is calculated by fitting a decreasing exponential to a slope of a respective raw fluorescence versus temperature curve. The decreasing exponential is fit to the respective melting curve profile through at least two slope values located on the respective melting curve profile where no sample melting occurs.

Illustratively according to this aspect, respective first and second slope values are used to derive each respective background signal. The respective first and second slope values are taken from points on the respective raw melting curve where no sample nucleic acid melting occurs.

Illustratively according to this aspect, each respective background signal is calculated using the equation $e^{a(T_R-T_L)}=B'(T_R)/B'(T_L)$, where $a=(\ln(B'(T_R)/B'(T_L)))/(T_R-T_L)$, $B'(T_L)$ is the first slope value, and $B'(T_R)$ is the second slope value. The background signal separation comprises using the equation $M(T)=F(T)-Ce^{a(T-T_L)}$, where $M(T)$ is the respective nucleic acid sample signal, $F(T)$ is the respective raw melting curve, and $C=B'(T_L)/a$.

Illustratively according to this aspect, each respective nucleic acid sample is a double-stranded product of a PCR reaction.

Illustratively according to this aspect, each respective melting profile comprises a melting transition for both a PCR product and an unlabeled probe.

Illustratively according to this aspect, each respective background fluorescence signal is calculated by fitting a respective decreasing exponential to a respective background fluorescence versus temperature curve. The respective decreasing exponential is derived from the respective first slope value taken from a point before the nucleic acid melting transition. The respective second slope value is taken from a point after the nucleic acid melting transition.

Illustratively according to this aspect, the method further comprises measuring a respective first slope value and a respective second slope value of the respective raw melting curve or a derivative thereof. The respective first slope value and the respective second slope value are obtained from a region of the respective raw melting curve not attributed to the sample melting. The method further comprises using the respective first slope value and respective second slope value to find an exponential representative of background noise to separate a respective background signal from a respective nucleic acid sample signal.

Illustratively according to this aspect, the method further comprises performing a difference function to identify differences between a corrected melting curve of a first one of the plurality of nucleic acid samples and a corrected melting curve of a second one of the plurality of nucleic acid samples.

Illustratively according to this aspect, the method further comprises performing a curve overlay function with the corrected melting curve of the first one of the plurality of nucleic acid samples and the corrected melting curve of the second one of the plurality of nucleic acid samples. The curve overlay function requires a single data point.

Illustratively according to this aspect, the distance between normalized curves is determined as an orthogonal metric.

Illustratively according to this aspect, the orthogonal metric is calculated using the equation $f_1(T)-f_2(T)=\max\{\sqrt{(1+f_1'(T)^2)}, \sqrt{(1+f_2'(T)^2)}\}$.

According to another aspect, a system for analyzing a plurality of nucleic acid samples comprises an instrument for sequentially heating fluorescently detectable complexes while monitoring their fluorescence. Each complex comprises a nucleic acid and a fluorescent species. The melting instrument is adapted to measure and to record sample temperature and sample fluorescence to determine sample fluorescence as a function of sample temperature to produce respective melting profiles of the respective fluorescently detectable complexes. Each melting profile comprises a respective background fluorescence signal and a respective sample fluorescence signal. The system further comprises a central processing unit (CPU) for performing computer executable instructions and a memory storage device for storing computer executable instructions that when executed by the CPU cause the CPU to cluster genotypes of a plurality of nucleic acid samples. Clustering is dynamically achieved by associating the distance between the sample melting curves.

Illustratively according to this aspect, the CPU performs clustering of genotypes of a plurality of double stranded nucleic acid samples. Clustering is dynamically achieved by associating a minimum distance between the sample melting curves of distinct genotype clusters.

Illustratively according to this aspect, the CPU and the memory storage device together comprise a CPU for performing computer executable instructions and memory storage device for storing computer executable instructions. When executed by the CPU, the computer executable instructions cause the CPU to analyze respective nucleic acids for sequence variations. This process includes separating respective background fluorescence signals from respective melting profiles by an exponential algorithm to generate respective corrected melting curves. The respective corrected melting curves comprise respective sample signals.

Illustratively according to this aspect, separating respective background fluorescence signals from respective melting profiles comprises measuring a first slope value and a second slope value of each respective melting profile. The first slope value and the second slope value of each respective melting profile are obtained from a region of the respective melting profile not attributed to sample melting. The first slope value and the second slope value are used to find an exponential function representative of the respective background fluorescence. The first slope value and second slope value are taken from points on the respective melting profile with a temperature greater than $T_m$.

Illustratively according to this aspect, the respective exponential function is calculated using the equation $e^{a(T_R-T_L)}=B'(T_R)/B'(T_L)$, where $a=(\ln(B'(T_R)/B'(T_L)))/(T_R-T_L)$, $B'(T_L)$ is the respective first slope value, and $B'(T_R)$ is the respective second slope value. The subtraction comprises using the equation $M(T)=F(T)-Ce^{a(T-T_L)}$, where $M(T)$ is the respective sample signal, $F(T)$ is the respective melting profile, and $C=B'(T_L)/a$.

Illustratively according to this aspect, the CPU normalizes the raw melting curves.

Illustratively according to this aspect, clustering is based on a distance metric selected from the group consisting of: the maximal distance between curves; the average of the absolute value of the distance between curves at all temperature points; and, the average of the root mean square of the distance between curves at all temperature points.

Illustratively according to this aspect, the CPU determines the number of clusters by selecting a maximum ratio of distances between adjacent cluster levels.

Illustratively according to this aspect, the CPU determines accuracy of the number of clusters by ordering the ratios of distances between two each adjacent cluster levels to determine the largest ratio.

Illustratively according to this aspect, the CPU determines a distance between clusters as the minimum distance between any two curves in each cluster.

According to yet another aspect, a method of analyzing a plurality of nucleic acid sample melting plots comprises subjecting each of the melting plots to at least one of exponential background subtraction, a curve overlay function, a difference plot function, and the clustering function.

Illustratively according to this aspect, the plurality of nucleic acid sample melting plots are subjected to exponential background subtraction using the equation $e^{a(T_R-T_L)}=B'(T_R)/B'(T_L)$, where $a=(\ln(B'(T_R)/B'(T_L)))/(T_R-T_L)$, $B'(T_L)$ is a first slope value, and $B'(T_R)$ is a second slope value. The subtraction comprises using the equation $M(T)=F(T)-Ce^{a(T-T_L)}$, where $M(T)$ is a sample signal, $F(T)$ is a signal function, and $C=B'(T_L)/a$.

Illustratively according to this aspect, the plurality of nucleic acid sample melting plots are subjected to the curve overlay function. The plurality of melting plots are shifted by using the equation $$\min\_c \int_a^b ((f(z)+c)-g(z))2\,dz = \int_a^b g(z)-f(z)\,dz$$

where $f(z)$ and $g(z)$ represent sections between two normalized fluorescence values. c is a constant that makes the mean difference of $(x_1(y)+c)-x_2(y)$ equal to zero.

Illustratively according to this aspect, the plurality of nucleic acid sample melting plots are subjected to the difference plot function. The difference between a first melting plot and a second melting plot of the plurality of melting plots is approximated using $f_1(T)-f_2(T)=\max\{\sqrt{(1+f_1'(T)^2)}, \sqrt{(1+f_2'(T)^2)}\}$.

Illustratively according to this aspect, the plurality of nucleic acid sample melting plots are subjected to the clustering function. The clustering function has a mathematical representation $\min\_\{f_1 \in C_1, f_2 \in C_2\}$, where $\|f_1-f_2\|$, and where $f_1$ represents a melting curve associated with subcluster $C_1$ to generate a plurality of clusters of melting plots.

Illustratively according to this aspect, the plurality of nucleic acid sample melting plots are subjected to the exponential background subtraction. The method further comprises performing the curve overlay function, the difference plot function, and the clustering function.

According to a further aspect, a method is provided for clustering melting profiles of a plurality of nucleic acid samples, each comprising a respective nucleic acid and a molecule that binds the respective nucleic acid to form a respective fluorescently detectable complex. The method comprises measuring the fluorescence of each nucleic acid sample as a function of temperature to produce a respective raw melting curve for each respective nucleic acid sample, normalizing the raw melting curves, and genotyping the plurality of nucleic acid samples by unbiased hierarchal clustering by forming a plurality of clusters of the melting curves wherein each cluster represents a genotype.

According to yet a further aspect, a system is provided for analyzing a plurality of curves, each represented as a signal function. The system comprises an instrument comprising a central processing unit (CPU) for performing computer executable instructions and a memory storage device for storing computer executable instructions that when executed by the CPU cause the CPU to cluster the plurality of curves. The clustering is hierarchically achieved upon assigning a distance between each pair of signal functions.

Illustratively according to this aspect, the distance is based on a distance metric selected from the group consisting of: the maximal distance between curves; the average of the absolute value of the distance between curves at all temperature points; and, the average of the root mean square of the distance between curves at all temperature points.

BRIEF DESCRIPTION OF THE DRAWINGS

FIGS. 1A-B are high resolution melting curves of a Factor V Leiden gene target interrogated with an unlabeled probe. FIG. 1A displays the original melting curves. FIG. 1B shows genotyping after exponential background subtraction.

FIG. 2A shows original melting curves of the Factor V Leiden gene target (top) and the melting curves after exponential background subtraction and the improved curve overlay function (bottom).

FIG. 3A shows a raw melting curve (top panel) and a failed attempt at genotyping the sample by the previous genotyping function (bottom panel). FIG. 3B shows a raw melting curve (top panel) and a successful result of genotyping the sample by the novel clustering function (bottom panel). FIG. 3C provides the melting curve of FIG. 3B (bottom panel) along side the 96 well reaction plate.

FIGS. 4A-F shows unlabeled probe and whole amplicon genotyping of the hemochromatosis gene target. FIG. 4A is a high resolution original melting curve. FIG. 4B is a negative derivative plot of the melting curve on FIG. 4A. FIG. 4C is the result of exponential background subtraction of the melting curve of FIG. 4B. FIG. 4D shows the original melting curve, and FIG. 4E shows a failed linear baseline normalization of the data in FIG. 4D. FIG. 4F shows genotyping of the hemochromatosis gene after exponential background subtraction.

FIGS. 5A-D show high resolution melting curves of the Factor V Leiden locus and unbiased hierarchal clustering after various functions. FIG. 5A shows the original melting curve data. FIG. 5B shows the negative derivative of the original melting data. FIG. 5C shows a linear baseline subtraction performed on the data of FIG. 5B. FIG. 5D shows the exponential background subtraction function performed on the data of FIG. 5A, followed by normalization and plotting as the negative derivative.

FIGS. 6A-D show high resolution melting curves of the Factor V Leiden locus with unlabeled probe genotyping. FIG. 6A shows the original melting curve data. FIG. 6B shows the result of a negative derivative plot on the data of FIG. 6A. FIG. 6C shows a negative derivative plot of the probe region after exponential background subtraction using slopes from regions indicated on the data of FIG. 6B. FIG. 6D shows the clustering of 3 genotypes performed by the clustering function on the data of FIG. 6C.

FIGS. 7A-D show scanning and genotyping data of exon 11 of the cystic fibrosis transconductance regulator (CFTR) gene. FIG. 7A shows the variant sequences analyzed under the unlabeled probes. FIG. 7B shows the normalized melting curves after exponential background subtraction. FIG. 7C shows the negative derivative plot of the probe region. FIG. 7D shows a difference plot of the PCR product melting transition.

FIGS. 8A-D show high resolution melting curves of exon 10 of the CFTR gene. FIG. 8A shows the variant sequences under the probes. FIG. 8B shows a normalized melting curve after exponential background subtraction. FIG. 8C shows the negative derivative plot performed on the data of FIG. 8B. FIG. 8D shows a difference plot of the PCR product melting transition.

FIG. 9C shows the clustered genotypes of the normalized melting curves of FIG. 9B.

FIG. 10A is a normalized melting curve after exponential background subtraction. FIG. 10B shows the difference plot after the previous vertical difference plot technique. FIG. 10C shows the difference plot after the orthogonal difference plot technique.

DETAILED DESCRIPTIONS OF ILLUSTRATIVE EMBODIMENTS

Figure 2B:
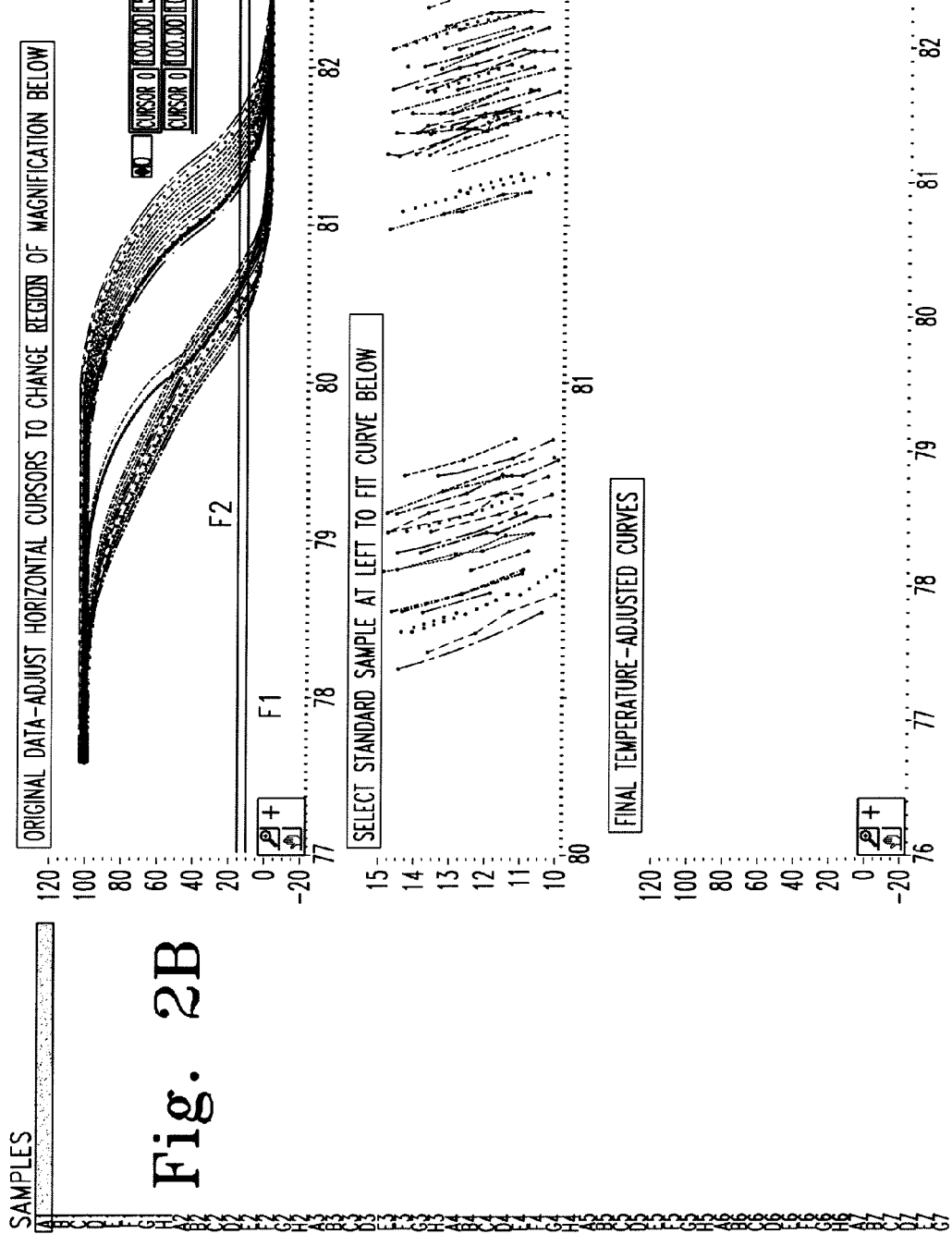
FIG. 2B shows the failed attempt of a previous curve overlay function on the original melting curve of FIG. 2A.

Referring to FIG. 1, a melting curve profile is shown before (FIG. 1A) and after (FIG. 1B) the exponential background subtraction (EBS) normalization is performed. EBS is a method for normalizing raw melting curve data and provides a better data set for analysis and genotyping. Performing EBS on a derivative or raw melting curve results in a corrected melting curve better suited for detailed analysis. Raw melting curves (FIG. 1A) often plot fluorescence values as a function of temperature.

In one example, exponential background subtraction is calculated by fitting the slope of the raw melting curve at two temperatures, $T_L$ and $T_R$. The raw melting curve is represented by the Equation Set (1), below, where $F(T)$ represents the raw melting curve, $M(T)$ represents the nucleic acid sample signal, and where $B(T)$ represents the background signal. $T_L$ and $T_R$ are obtained from points away from the melting transition temperatures of the sample signal where the melting transition does not significantly affect the slope, therefore the slope ($M'(T)$) of the signal ($M(T)$) is essentially zero and effectively vanishes exponentially. This is reflected in Equation Set (2).

$$F(T)=M(T)+B(T) \quad \text{Equation Set (1)}$$

$$F'(T_L)=B'(T_L) \text{ and } F'(T_R)=B'(T_R). \quad \text{Equation Set (2)}$$

An exponential model is fit for Equation 3, where the form of the exponential is shifted to $T_L$ for numerical stability to these two values:

$$B'(T)=aCe^{a(T-T_L)} \text{ at } T=T_R, T_L. \text{ At } T=T_L, \text{ this gives } aC=B'(T_L) \text{ and at } T_R \text{ this gives } B'(T)=aCe^{a(T_R-T_L)}=B'(T_R).$$

$$B(T)=Ce^{a(T-T_L)}$$

$$B'(T)=aCe^{a(T-T_L)} \text{ at } T=T_R, T_L$$

$$aC=B'(T_L) \text{ at } T=T_L$$

$$aCe^{a(T_R-T_L)}=B'(T_R) \text{ at } T=T_R \quad \text{Equation Set (3)}$$

It is understood that $T_L$ and $T_R$ have been measured in generating the raw melting curve, and therefore these values are used to obtain the parameters (a) and (C), as shown in Equation Set (4).

$$e^{a(T_R-T_L)}=B'(T_R)/B'(T_L), \text{ so that } a=(\ln(B'(T_R)/B'(T_L)))/(T_R-T_L)$$

$$C=B'(T_L)/a$$

$$M(T)=F(T)-Ce^{a(T-T_L)} \text{(Background removed)} \quad \text{Equation Set (4)}$$

Because the slopes of $T_L$ and $T_R$ are used to determine the exponential background rather than the fluorescent values, the background subtraction may be calculated without reference to the amount of signal present, which may vary due to amount of materials present or simply sample-to-sample variation.

The signal $M(T)$ may optionally be normalized, illustratively to the range 0-100 by applying the linear shift and resealing according to Equation Set (5) on the interval of interest.

$$M(T)=100(M(T)-m)/(M-m), \text{ where } m=\min\{M(T)\} \text{ and } M=\max\{M(T)\} \quad \text{Equation Set (5)}$$

Alternatively, in another example, an exponential can be fit to the background fluorescence of a derivative melting curve. The background is removed by fitting the height of a numerically computed derivative curve with an exponential, then subtracting the background from the raw melting curve. Since the derivative of an exponential is an exponential with the same decay rate, exponential background subtraction is applied in the present embodiment to the derivative curve by subtracting an exponential fit of the values at the temperatures of interest. In this method, one may use the value (height) of the collective derivative curve at the two temperatures $T_L$ and $T_R$ and fit these values to the corresponding model for $B'(T)=De^{a(T-T_L)}$ where D corresponds to aC from the derivation above. In this situation, the parameters D and a are solved as follows. At $T=T_L$, this gives $D=B'(T_L)$ so there is no need to solve for the parameter D; it appears directly as a measurement. At $T_R$ this gives $De^{a(T_R-T_L)}=B'(T_R)$. Dividing the second equation by the first gives $e^{a(T_R-T_L)}=B'(T_R)/B'(T_L)$ so that $a=\ln(B'(T_R)/B'(T_L))/(T_R-T_L)$ consistent with the method above (the exponential decay rates of an exponential and its derivative are the same) though now the values of B' are determined from the height of the numerical derivative of the measured data instead of the fitting the slope of the measured data. Finally, the derivative of the signal with the background derivative removed by subtraction is obtained: $M'(T)=F'(T)-De^{a(T-T_L)}$ with the parameters D and a determined as above. As above, the derivative signal $M'(T)$ may optionally be normalized, illustratively to the range 0-100 by applying the linear shift and resealing $M'(T)=100(M'(T)-m)/(M-m)$ where $m=\min\{M'(T)\}$ and $M=\max\{M'(T)\}$ on the interval of interest, respectively.

In FIG. 1, illustrative melting curves are shown for various genotypes in a model system of the Factor V Leiden gene using an unlabeled probe. Transitions for melting of both the unlabeled probe and the amplicon are visible. In this illustrative example, line pairs 1 (lines 1, 2) and 2 (lines 3, 4), as shown in FIG. 1A, represent respective cursor pairs. Each cursor pair provides a region outside of the melt transition for extracting temperature intervals of the raw melting curve data that are used for determining $F(T_L)$ and $F(T_R)$ in EBS analysis. Each of the two regions is selected so that they are small enough that the slope does not change significantly in the region, but wide enough to provide an accurate sample of the local slope. However, since the background is an exponential, the slope will not be constant if the region is widened too much. In one example, automatic initial positioning algorithms may be provided in the software. For example, background regions may be identified where the exponential differential equation is satisfied, $y'=Cy$ where C is constant. If desired, the software may permit the user to adjust the cursors to try to improve the results. Alternatively, the software may permit the user to set the cursors to specific areas, if the melting transition regions are known. Other methods of setting the regions are possible.

In the present example, melting curves were generated from data taken from the HR-1 melting instrument. A slope value $T_L$ is generated from cursor pair 1 and $T_R$ is generated from cursor pair 2. In this example, the cursor pairs are respectively located at approximately 76° C. and 85° C., but it is understood that the placement of the cursor pairs will vary depending upon the melting transitions of the nucleic acid(s) present in the sample. Cursor pair 1 and 2 bracket the probe melting transition of the sample nucleic acid, but cursor pair 2 is also located before the amplicon melting transition region. After the exponential fit is performed with the slopes generated from the cursor pairs the exponential background subtraction is performed. FIG. 1B represents the probe melting region after the background has been subtracted, using the EBS equations and normalization discussed above. Exponential background subtraction for the amplicon melting region using the same or different cursor pairs can be performed (not shown) with the same exponential found for the probe melting region.

While illustratively the cursor pairs are placed on either side of at least one melt transition, it is understood that the position of the cursor pairs may vary in the practice of this invention. For example, in an alternative embodiment, slope values ($T_L$ and $T_R$) are both obtained from points before the probe melting region. In yet another alternative embodiment, slope values ($T_L$ and $T_R$) are both obtained from points after the probe melting region but before the amplicon melting region. In yet another alternative embodiment, slope values ($T_L$ and $T_R$) are both obtained from points after the amplicon melting region. In yet another alternative embodiment, slope values ($T_L$ and $T_R$) are obtained from points before the probe melting region and after the amplicon melting region. In another alternative embodiment, the slope values ($T_L$ and $T_R$) are obtained at any two points on the raw melting curve where neither the probe nor the amplicon are melting. Although the illustrative cursor pairs are spaced apart from each other, it is possible to do exponential background subtraction with two slope values ($T_L$ and $T_R$) that are close together. Such may be useful for very crowded melting curves with limited non-melting regions.

Exponential background removal identifies the sample melting curve signal independent of user choice of where the user decides to fit the background, as long as $T_L$ and $T_R$ are outside the melting range. In general, background noise includes background fluorescence signals and alternate non-nucleic acid melting signals, both of which interfere with the analysis of the sample data. By example, when using unlabeled probes and multiplex amplicons at lower temperatures (less than 80° C.), background noise at low temperatures has occasionally previously prevented the identification of sample signal curves.

Prior art methods for background subtraction may fail as the background signals and the sample signals approach an equal amplitude. Even where the sample signal is significantly higher than the background, the exponential background subtraction has been found to be more consistent and accurate.

As an example, the exponential background subtraction provides enhanced accuracy and specificity when distinguishing the melting curves of samples. A recent study found 100% accuracy in distinguishing between a normal wild type sample and a homozygous mutant sample where the amplicons were approximately 40 base pairs in length. Prior to the use of exponential background subtraction, it was theoretically understood that a fraction of small amplicons of a normal wild type sample and their homologous mutant sample would have identical curves, particularly if the GC content remained the same between the two amplicons. The use of higher resolution melting and exponential background removal is therefore attributed to extremely high accuracy of genotyping and mutation scanning of double stranded nucleic acid samples.

High resolution melting analysis is useful to obtain viable results for identifying the efficacy of background removal and genotyping. Melting analysis may be performed on a variety of melting instruments, including the high-resolution melting instruments HR-1™ (a capillary-based melter) and Light-Scanner® (a plate-based melter) (both Idaho Technology, Salt Lake City, Utah). However, it is understood that melting curve analysis may be performed in the absence of amplification, particularly on highly uniform nucleic acid samples. In one illustrative melting protocol using the HR-1, the samples were first amplified in the LightCycler® (Roche Diagnostics Corp, Indianapolis, Ind.) (or in the RapidCycler® (Idaho Technology, Salt Lake City, Utah)), then heated momentarily in the LightCycler to 94° C. and rapidly cooled (program setting of −20° C./s) to 40° C. The LightCycler capillaries can be transferred one at a time to the high-resolution instrument and heated, illustratively at 0.3° C./s. The HR-1 is a single sample instrument that surrounds one Light-Cycler capillary with an aluminum cylinder. The system is heated by Joule heating through a coil wound around the outside of the cylinder. Approximately 50 data points may acquired for every ° C. The LightScanner is a plate-based system that provides high resolution melting on 96- or 384- well microtiter plates. PCR may be performed in any compatible plate-based thermal cycler.

In some cases it is advantageous not to denature the product after PCR before melting curve acquisition. For example, when the goal is to type the number of repeat sequences (e.g., STRs, VNTRs), amplification may be stopped at the extension step during the exponential phase of the reaction before plateau, and then melting analysis is performed. This way, homoduplex extension products can be analyzed. In repeat typing, homoduplex products can be more informative than heteroduplex products, especially since many different heteroduplex products may form from different alignment of the repeats. In some cases, it may be helpful to obtain both a homoduplex melting curve (without prior denaturation) and a heteroduplex melting curve (with denaturation and the formation of all possible duplex combinations). The difference between these two melting curves gives a measure of the extent of heteroduplexes that can be formed, using the same sample as the "homoduplex control".

Previous background subtraction techniques often included numerical differentiation as an element. Numerical differentiation of raw data involves artificial fitting and smoothing, which can affect the efficacy of the data. Common numerical differentiation techniques include negative derivative curves and integrated derivative curves. The present embodiment does not require the raw data to be numerically differentiated. This is an advantage over previous background subtraction techniques. The conversion of raw data to derivative curves often involves the amplification of background noise and artificial smoothing of significant features of the melting data. The present embodiment is capable of distinguishing subtle but molecularly significant differences in melting data, which is an advantage over previous techniques that involved derivative curve analysis.

While the above exponential background subtraction method is used in reference to nucleic acid melting curves, it is understood that this method may be applied to a variety of data sets, including other biological data sets, having exponential background noise, and is particularly suited where background subtraction without using the value of the signal for calculation is important.

Curve Overlay Function

An alternative embodiment includes a curve overlay function for use in melting curve analysis. Previous methods of curve overlay, or temperature shifting, include the steps of selecting a fluorescence interval, usually at low fluorescence (e.g., 5-15%) of the normalized melting curve, fitting a second degree polynomial to all points within the interval for each curve, and then shifting each curve to best overlay the plots in this interval. Curve overlay corrects any minor inter-run temperature variation and increases the ability to distinguish heterozygotes from homozygotes. However, the previous method failed when fewer than three (3) points were in the interval. Absent the three data points, the previous method could not provide a means for automatic and accurate curve overlay, as the known mathematical overlay methods could not be applied with high accuracy. Known methods of mathematical overlay include the least distance method, the lowest average of absolute distance values method, and the least squares method.

The present embodiment analyzes the normalized melting curves by overlaying them between a lower dependent variable value ($y_L$) and a higher dependent variable value ($y_H$). This is performed by extracting all numerical (x,y) values in the interval provided that all (y) values continue to decrease, or all (y) values continue to increase. Instead of fitting (y) as a function of (x) and finding the best overlay of such fits, the ordered pairs are reversed, thereby making (x) a function of (y). An example of the optimal least squares fit of one horizontally shifted function is shown in Equation Set 6, $x_1(y)+c$ to another, $x_2(y)$ is obtained by finding the constant c which makes the mean difference of $(x_1(y)+c)-x_2(y)$ equal to zero.

$$\min\_c \int_a^b ((f(z)+c)-g(z))2\,dz = \int_a^b g(z)-f(z)\,dz \quad \text{Equation Set (6)}$$

The value $x_2(y)$ is obtained by finding the constant (c), thereby making the mean difference of $(x_1(y)+c)-x_2(y)$ equal to zero. The value (z) represents a variable of integration. The value (z) in Equation Set 6 represents either value (x) or value (y), which is in part due to the independent variable being the original (y) and equal to the fluorescence value. The functions f(z) and g(z) represent sections between two normalized fluorescence values (low and high) that are chosen for overlay of two normalized melting curves, where temperature is plotted as a function of fluorescence. The value (dz) is a normalized measure on a normalized fluorescence interval.

In order to scan for heterozygotes within a PCR product, the shape is more important than the absolute temperature or $T_m$. Heterozygotes produce heteroduplexes that melt at lower temperatures and distort the shape of an overall melting curve. Shape differences are more efficient to use when identifying different genotypes than absolute $T_m$s because temperature variation can be caused by minor sample differences and instrument variability. Possible sample differences include, but are not limited to, variances in ionic strength and the occurrence of evaporation during processing procedures. Instrument variability is also possible with respect to relative and exact well positions on the sample plates.

As discussed above, previous methods for comparing curve shape included the overlay of curves by shifting them along the temperature axis, implemented by fitting a second degree polynomial to a small fluorescence interval of each curve. An arbitrary standard curve was then chosen, and the remaining curves were shifted to overlay the standard curve over this region. However, when the data density and fluorescence interval are small, the previous method is prone to failure, as shown in FIG. 2B. The top panel (FIG. 2B) includes melting curves for a PCR fragment of Factor V Leiden from 96 genomic DNA samples, having been normalized by the exponential background subtraction method. Three distinct genotype clusters are visible within FIG. 2B. Also shown in the top panel are fluorescence interval markers F1, F2 over which the overlay is attempted. The first interval marker F1 is approximately at 10% fluorescence and the second interval marker F2 is approximately at 15% fluorescence. A magnified plot of actual data points from 80 to 82° C. contained within the selected fluorescence interval is shown in the middle panel. Various curves show that fewer than three points are included within this interval, which makes a quadratic fit impossible and ultimately leads to failure of the previous curve overlay method, as shown in the bottom panel.

The present embodiment utilizes the algorithm of Equation Set (6) (FIG. 2A) with the same data set. The present embodiment accurately and successfully analyzes the data, and in fact needs only one data point from each of the respective curves to do so, thereby providing a novel and improved method of analysis. In the top panel of FIG. 2A, raw data are shown along with vertical cursors (See FIG. 1A and description above) that define the regions for slope estimation of the exponential background. Provided in the bottom panel (FIG. 2A) is the normalized background subtracted curves that have been successfully temperature shifted so that all curves are overlaid within the 10-15% fluorescence region.

The present embodiment is an advantageous method over previous methods for various reasons, including that only one (1) data point is required for validity and accuracy of the curve overlay function. The present embodiment is furthermore advantageous as it has rigorous optimality for least-squares fitting. It is contemplated that the present embodiment of the curve overlay function can be represented in numerous mathematical representations other than described herein, and Equation Set (6) is considered one of such examples.

Difference Plot Function

Another alternative embodiment includes an improved difference plot function for analyzing differences between nucleic acid sample melting curves. Previous methods subtracted all curves from an arbitrary reference curve or an average of reference curves. The result of the subtraction was purely the vertical distance between curves at each temperature point. These difference plots visually magnified the difference between curves so they could be more easily viewed. However, the vertical distance between curves does not accurately portray the shortest distance between curves. This is especially the case when the fluorescence value of the melting curves drop at a significant rate or negative slope. This shortcoming presented an artifact known as a "variation bubble", which is often clearly visible where the decrease in fluorescence is maximal.

A novel improvement in the present difference plot function is to weight the differences between curves according to the slope of the curves. This provides a better distance metric between curves so that common and distinct genotypes can be correctly and automatically identified. Weighting balances the effect of slope on the difference measure between curves. When weighting is not performed, standard vertical differencing overemphasizes the difference between curves when the slope is steep, enlarging the spread of melting curves within the same genotype. The present method provides a practical computable approximation to the orthogonal difference between melting curves, which thus better represents variations in the distance between curves.

The present embodiment provides a novel method for analysis of melting curve data. The analyzed melting curves may be normalized by various known methods, but the novel exponential background subtraction described herein is preferable. Instead of the vertical distance at each temperature, an orthogonal distance between curves is advantageous. The present embodiment obtains the least distance between curves, which is the least distance between curves at each point. When the fluorescence is dropping rapidly, instead of using the vertical distance between lines, a metric orthogonal to the slope of curves is more useful and accurate to assess differences between curves. When measuring orthogonal distances between two curves, the results are often different depending on which curve is used as the reference. The present embodiment provides a method to estimate the orthogonal distance between two curves.

To compensate for exaggerated emphasis upon the melting regions of two melting curves being compared and consequent de-emphasis upon regions surrounding their primary melts when using simple vertical differencing, $f_1(T)-f_2(T)$, an approximation of the orthogonal distance between curves can be found by using Equation Set (7).

$$f_1(T)-f_2(T)=\max\{\sqrt{(1+f_1'(T)^2)}, \sqrt{(1+f_2'(T)^2)}\} \quad \text{Equation Set (7)}$$

Equation Set 7 is an example of a method for taking the melting regions of both melting curves into account symmetrically. The equation further generalizes the orthogonal distance from the origin to the line (y=b−mx), where the vertical distance from the origin is (b), but where the orthogonal distance from the origin is $(b/\sqrt{(1+m^2)})$. The result of the present embodiment is a measurement which reflects sequence dependent variations in the melting curves more sensitively and evenly throughout the range of measurement, while being suitable for automated and dynamic use within a computer system. An example of difference functions are provided in FIGS. 10A-C where both the previous vertical (FIG. 10B) and the novel orthogonal (FIG. 10C) differences are plotted using normalized melting curves that have had their background exponentially subtracted. Vertical difference plots show a "variation bubble" around the region of steepest slope, even though all samples are wild types. The variation bubble is eliminated when orthogonal differencing is employed.

Weighting balances the effect of slope on the difference measure between curves. When weighting is not performed, standard vertical differencing overemphasizes the difference between curves when the slope is steep, enlarging the spread of melting curves within the same genotype. The present invention provides a practically computable approximation to the orthogonal difference between melting curves which thus better represents variations in the distance between curves.

Genotype Clustering Function

Yet another alternative embodiment includes a genotype clustering function with automatic determination of the number of clusters. Specifically, unbiased hierarchal clustering was used in contrast to previous methods that clustered genotypes based on learned data sets and arbitrary cutoffs. Since the genotypes are usually unknown before analysis, prior data sets do not satisfactorily predict the appropriate grouping of future data sets. Such learned data set methods are often unable to provide an accurate and automated means for clustering, particularly for unknown genotypes. In contrast, unbiased hierarchal clustering requires no prior learning or established cutoffs and robustly adjusts to the quality and resolution of the available melting data.

The novel unbiased hierarchal clustering method is based on a distance metric between melting curves. The distance metric is selected from: 1) the maximal distance between curves, 2) the average of the absolute value of the distance between curves at all temperature points, and 3) the average of the root mean square of the distance between curves at all temperature points. Preferably, the distance metric is derived after EBS, normalization, optional curve overlay, and is the novel orthogonal distance metric described in the previous section. Sequential, unbiased, hierarchal clustering is then performed as is standard in the art.

Automatic determination of the most likely number of clusters is a novel aspect of the present disclosure. Specifically, the likelihood for each level of clustering (number of clusters) is determined by considering the ratio of distances between cluster levels. During hierarchal clustering, two subclusters $C_1$ and $C_2$ are joined into a larger cluster by considering the weighted average of all points in each subcluster (the quantity minimized to determine which subclusters to merge at each stage). Instead of using the weighted averages to calculate the distance ratios, the minimum distance between curves in distinct clusters is used as a more accurate measure of the separation between clusters of data and their subclusters. This compensates for the naturally growing distances between the weighted average curves representing hierarchical sub-clusters formed during the agglomerative clustering process by keeping the distance measure associated with sub-clusters limited to the distance between the nearest-neighboring curves in each sub-cluster, rather than the distance between the most recently joined weighted averages. The present embodiment accurately determines which cluster level is the most likely by assessing the ratio between two adjacent cluster level distances. This ratio provides a more accurate and stable likelihood assessment of the clustering level (number of clusters), accurately separating fine scale from large scale phenomena. The largest ratio defines the most likely number of clusters, the next largest ratio defines the second most likely number of clusters, etc. In genotyping applications where there are sufficient curves for multiple representations of the main genotypes, this method provides a robust criterion for identifying the genotyping level in hierarchical clustering intrinsically.

A mathematical representation of the clustering process is shown at Equation Set (8), where $\|f_1-f_2\|$ represents the distance metric used in the ratio that orders the cluster levels (number of clusters) by likelihood. The difference measurement ($\|f_1-f_2\|$) indicates the measure of distance between two normalized melting curves and is selected from a group comprising: the mean absolute separation, the mean squared separation, and the maximum separation at a chosen temperature. It is contemplated that various other known methods for measuring distances between two melting curves may be used with respect to Equation Set 8.

$$\min\_\{f_1 \epsilon C_1, f_2 \epsilon C_2\} \|f_1-f_2\| \qquad \text{Equation Set (8)}$$

At a point when subclusters $C_1$ and $C_2$ have been joined the value ($f_1$) represents a melting curve associated with subcluster $C_1$, and the value ($f_2$) is a melting curve associated with subcluster $C_2$. The value ($\min\_\{f_1 \epsilon C_1, f_2 \epsilon C_2\}$) represents the smallest value of the distance among all pairs of melting curves, where a first value is taken from a first subcluster, the first subcluster having been joined, and a second value being taken from a second sub-cluster.

The present embodiment is a new method for measuring the distance between cluster levels to determine the likelihood of a particular level (number of clusters). The new distance measure is the minimal distance between any two members, as long as each is from a different cluster. In order to determine the likelihood of any cluster level (i.e., 3 vs. 4 vs. 5 clusters), the ratio of the distance to the next cluster is divided by the distance to the previous cluster. The above method provides the correct classification of genotypes when parameters such as cursor locations are varied. When the weighted averages are used rather than the distance between the nearest-neighboring curves in each sub-cluster to determine the ratio, the choice of the most likely number of clusters is much less stable. Furthermore, the present embodiment can be automatically executed with high accuracy.

Figure 3A:
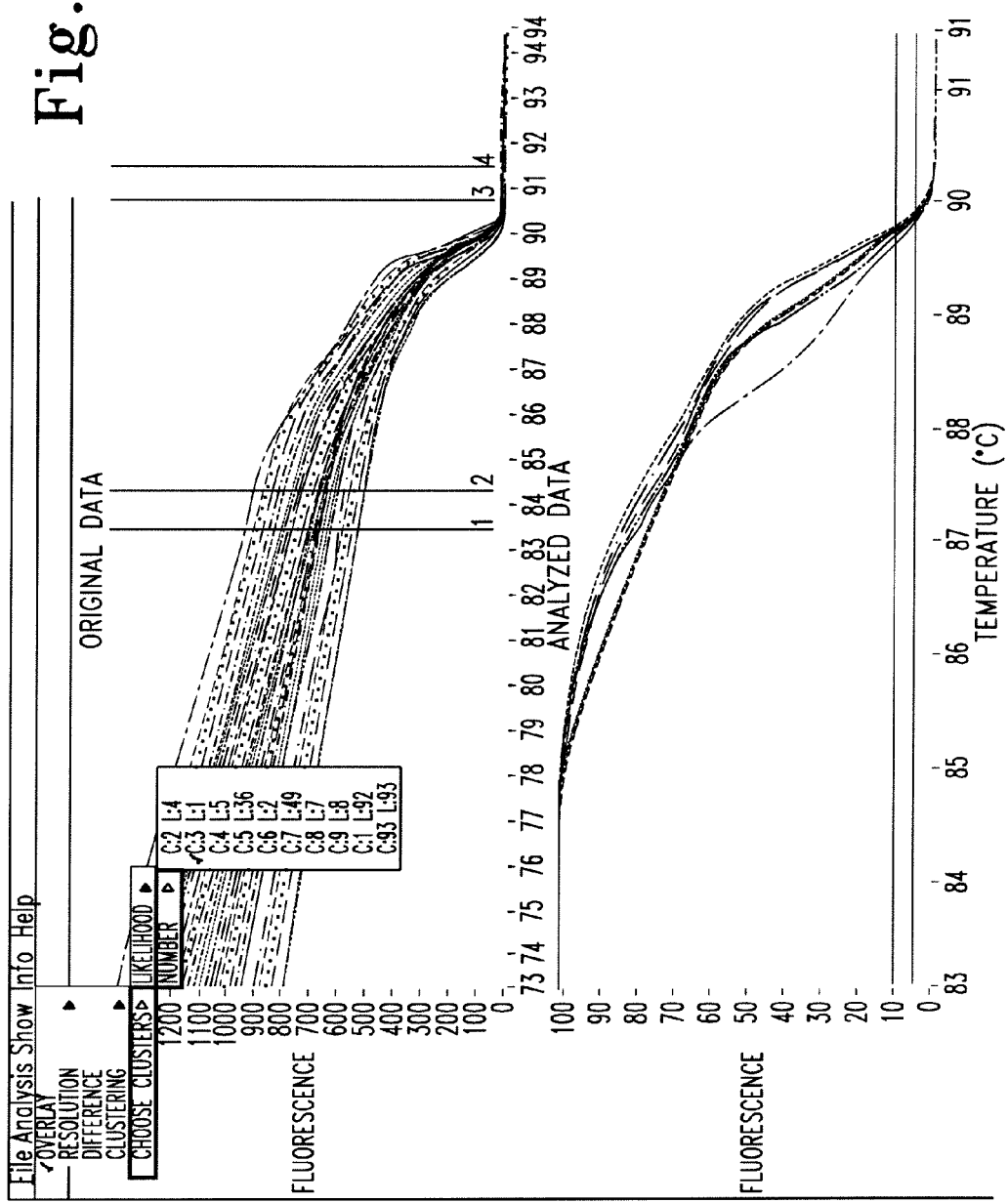
FIGS. 3A-C show analyzed melting curves of the Hepatic Lipase gene.
Figure 3B:
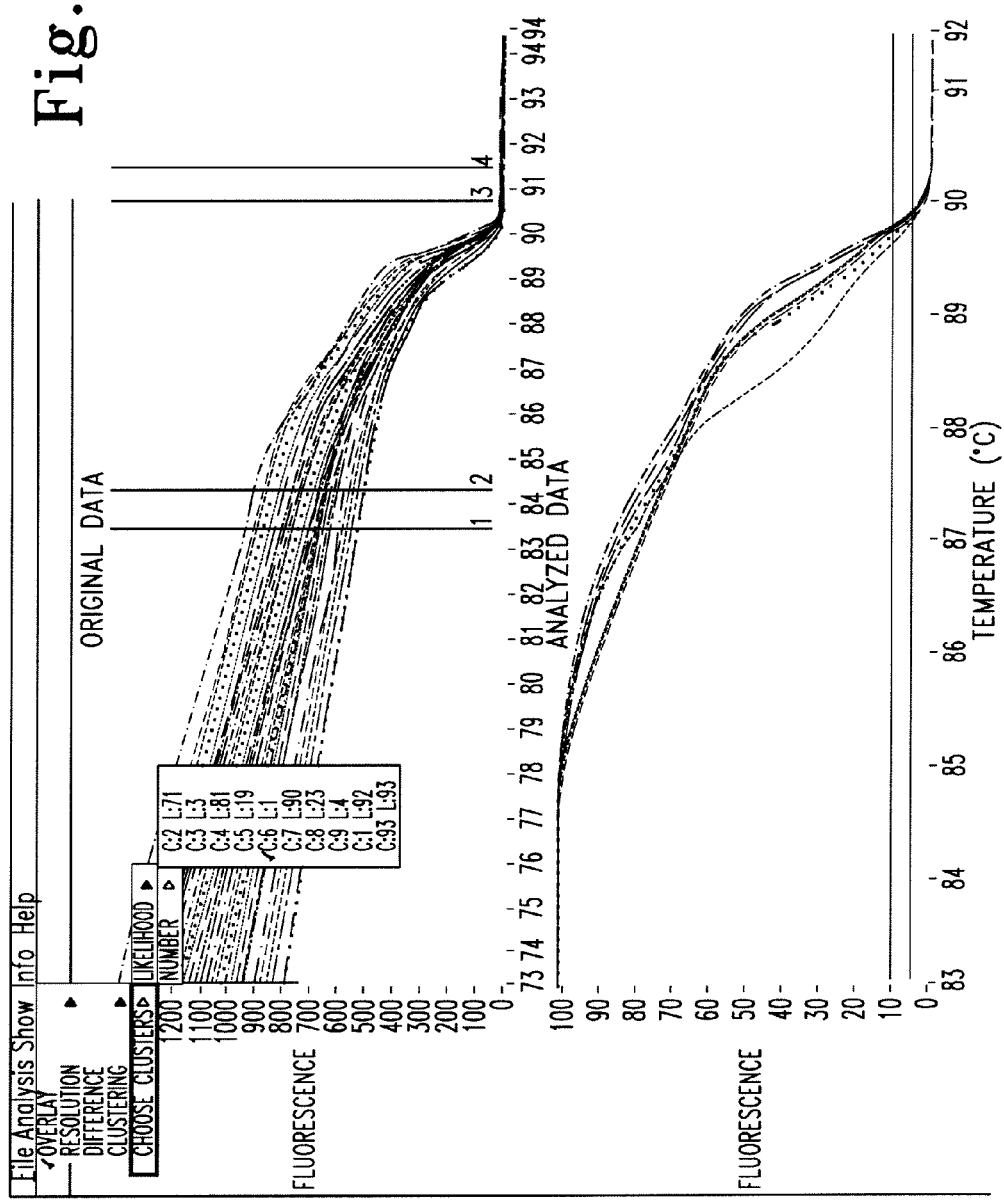
Figure 3C:
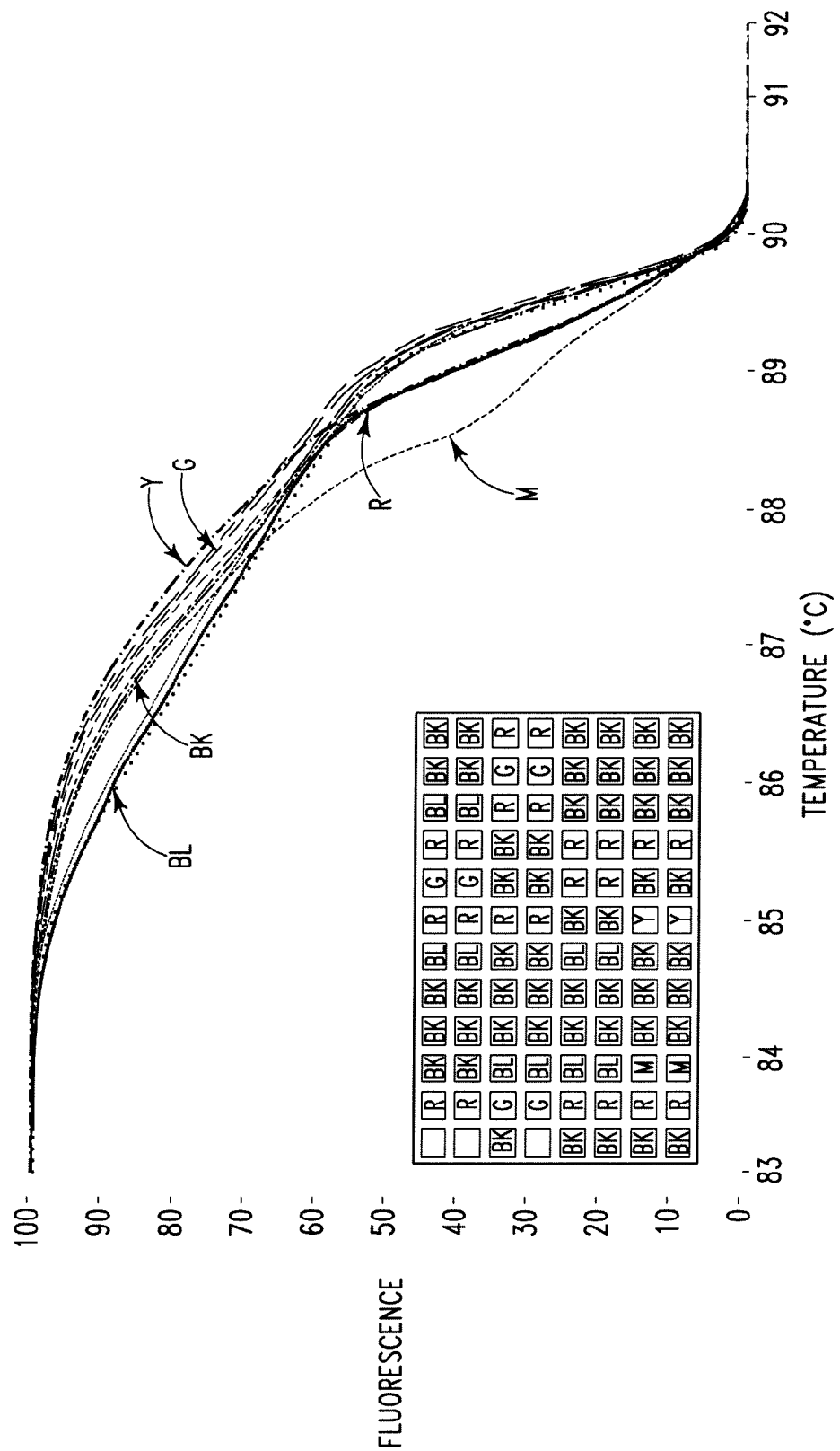

FIGS. 3A-C demonstrate the ability of the novel clustering function to assign the correct number of genotype clusters to a multi-sample melting curve. Six separate genotypes of human genomic DNA of the hepatic lipase gene were amplified (BioRad iCycler) using 10 µl reaction volumes in a 96 well plate. The 1× LightScanner® Master Mix (Idaho Technology, Salt Lake City, Utah) was used. The samples were heated from 75° C. to 94° C. at 0.1° C./second in the Light-Scanner melting instrument.

FIG. 3A shows a screen shot of the raw melting curve (top panel) for the hepatic lipase gene amplification and melting transition. The bottom panel shows the result of the previous clustering function along with a drop-down menu indicating that the previous clustering function incorrectly indicates the presence of only three distinct genotype clusters in the samples, which are represented as three separate colored line clusters.

FIG. 3B shows a screen shot of the raw melting curve (top panel) for the hepatic lipase gene amplification and melting transition. The bottom panel shows the result of the present embodiment clustering function along with a drop-down menu indicating that the novel clustering function correctly indicates the presence of six distinct genotype clusters in the samples, which are represented as six separate colored line clusters. FIG. 3C demonstrates that the user can identify the samples by genotype by their positioning on the 96 well reaction plate shown along side the fluorescence vs. temperature plot of FIG. 3B.

It is understood that melting plots may be analyzed using one or more of the algorithms of exponential background subtraction, curve overlay function, difference plot function, and the clustering function, and that each of these methods may be used alone or in any combination and may be used in combination with other methods of analyzing melting plots.

EXAMPLE 1

Hemochromatosis (HFE) Mutation and Polymorphism Genotyping

Hemochromatosis gene mutations and polymorphisms are known to interfere with normal iron metabolism in Humans. In this illustrative example, detection and identification of polymorphism and mutation genotypes through melting curve analysis is more accurate with exponential background subtraction then baseline background subtraction. Analysis was performed with small amplicons (78 bp and 40 bp) in order to increase the $T_m$ difference between different homozygote samples. Unlabeled probes are utilized for genotyping SNPs that otherwise could not be easily genotyped by amplicon melting.

Figure 4A:
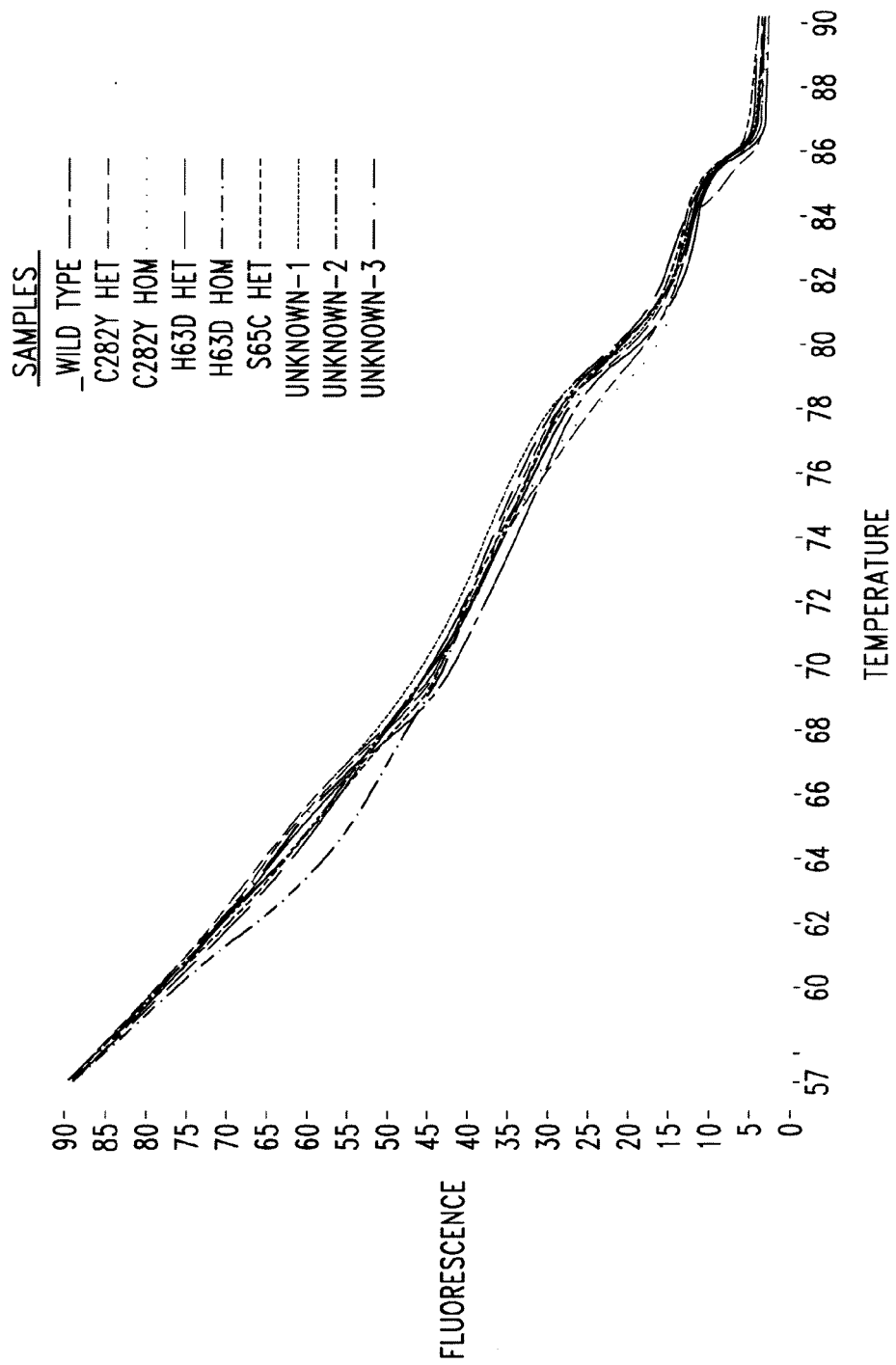
Figure 4C:
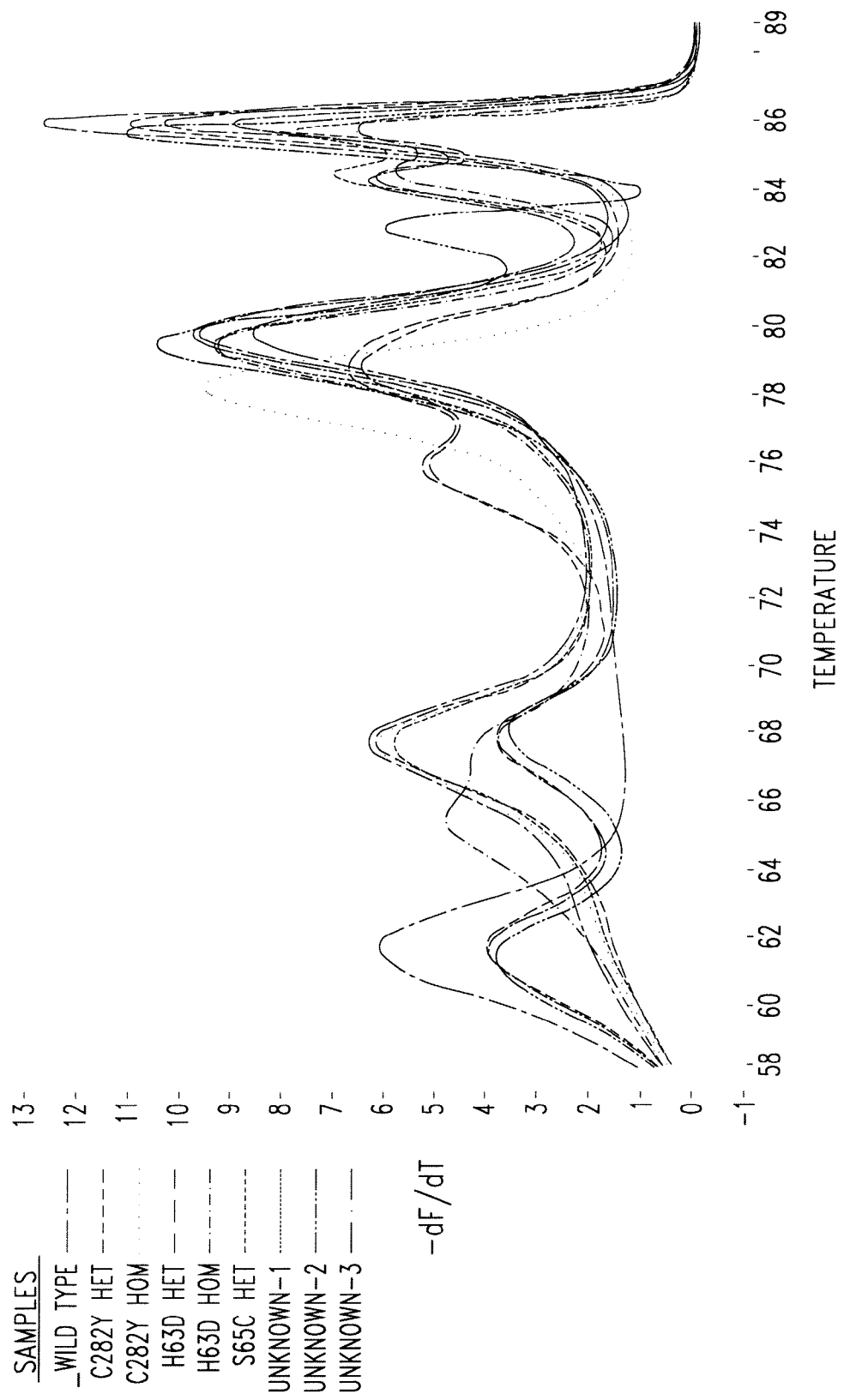
Figure 4F:
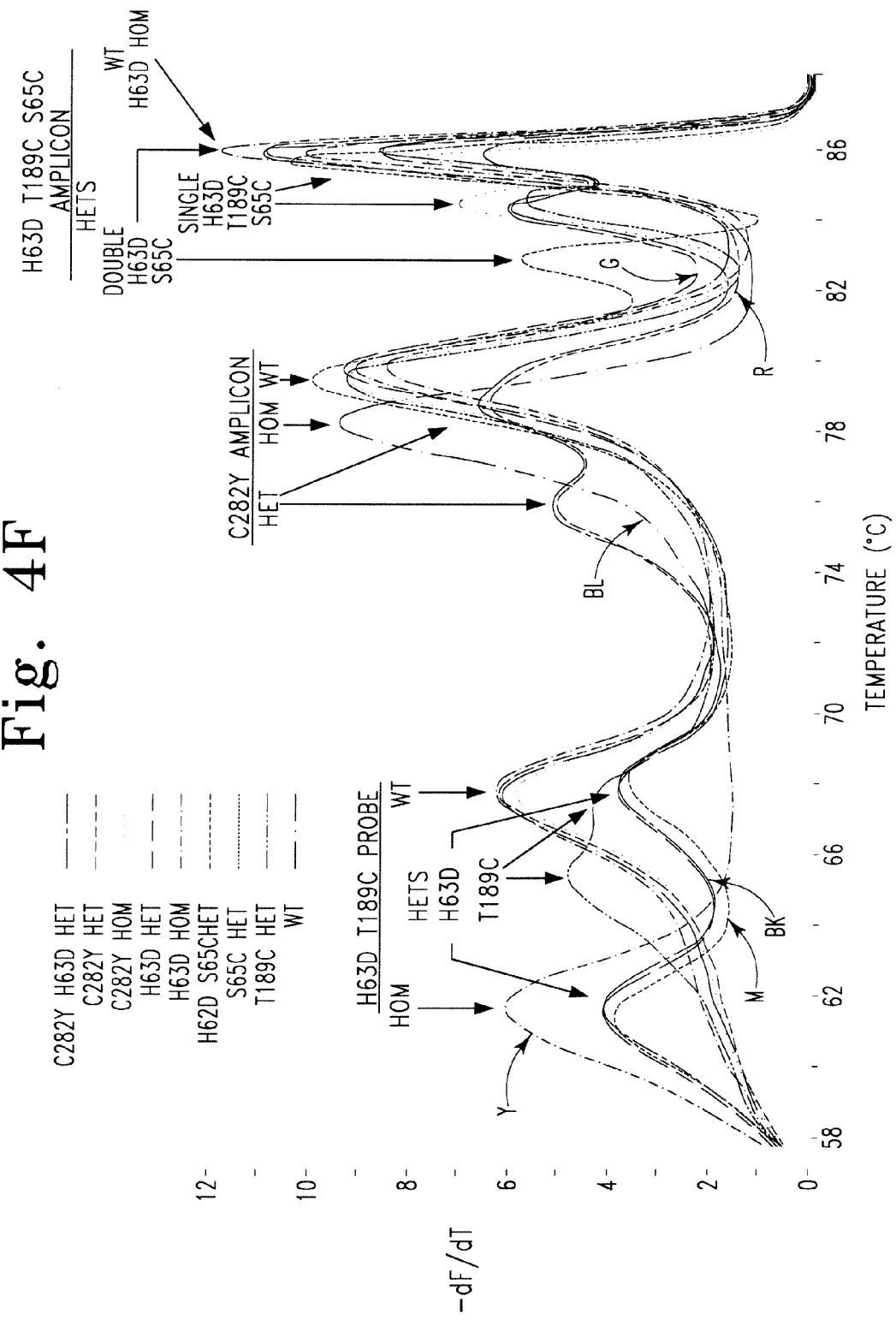

Human genomic DNA representing distinct hemochromatosis genotypes can be amplified by various PCR instruments. An exemplary method includes 10 µl reaction volumes with a Roche LightCycler® 2.0. Following PCR amplification, the HFE samples are heated in an HR-1 (Idaho Technology) melting instrument for approximately 115 seconds. The resulting florescence versus temperature plot is depicted as FIG. 4A. The derivative melting curves are shown in FIG. 4B. In this illustrative example, exponential background subtraction is performed on the derivative melting curves, and the normalized derivative melting curves are displayed as FIG. 4C. Compared to the exponential background normalized melting curve (FIG. 4C) the baseline technique for normalizing melting curves is clearly deficient. As shown in FIGS. 4D-4E, the baseline technique applied to a combined probe plus amplicon melting curve (FIG. 4D) results in a absence of useable data (FIG. 4E), even though the baseline and exponential background subtraction techniques used the same melting curve data set (FIG. 4B, 4D). Genotype identification of FIG. 4C for the C282Y homozygous and heterozygous, H63D heterozygous and homozygous and wild type samples is shown in FIG. 4F.

EXAMPLE 2

Factor V Leiden (384 Well Plate) Derivative Clustering Combined Probe and Amplicon Factor V Leiden is the most common hereditary blood coagulation disorder in the United States. It is present in approximately 5% of the Caucasian population and approximately 1.2% of the African American population. Factor V Leiden as a gene target is important for the detection of SNPs that are linked to coagulation disorder disposition.

Human Factor V Leiden genomic DNA samples representing different Factor V Leiden genotypes were amplified in an ABI 9700 with 10 µl reaction volume and 12 µl oil overlay. The assay included a Factor V Leiden amplicon of approximately 100 bp having a sequence of 5'-CTGAAAGGTTACT-TCAAGGACAAAAT ACCTGTATTCCTCGCCTGTCCAGGG ATCTGCTCTTA- CAGATTAGAAGTAGTCCTATTAGCCCA- GAGGCGATGTC-3' (SEQ. ID NO:1), which was amplified by forward primer 5'-CTGAAAGGTTACTTCAAGGAC-'3

(SEQ. ID NO:2) and reverse primer 5'-GACATCGC-CTCTGGG-3' (SEQ. ID NO:3). The assay also included an unlabeled probe 3'-TGGACATAAGGAGCGGACAGGT-5' (SEQ. ID NO:4) that is configured to hybridize to the forward strand of the amplicon, as indicated by the underline. The resultant PCR samples were heated from 58° C. to 88° C. at 0.1° C./s in a LightScanner melting instrument using a 384 well reaction plate. The total melting procedure required approximately 5 minutes for completion.

Figure 5A:
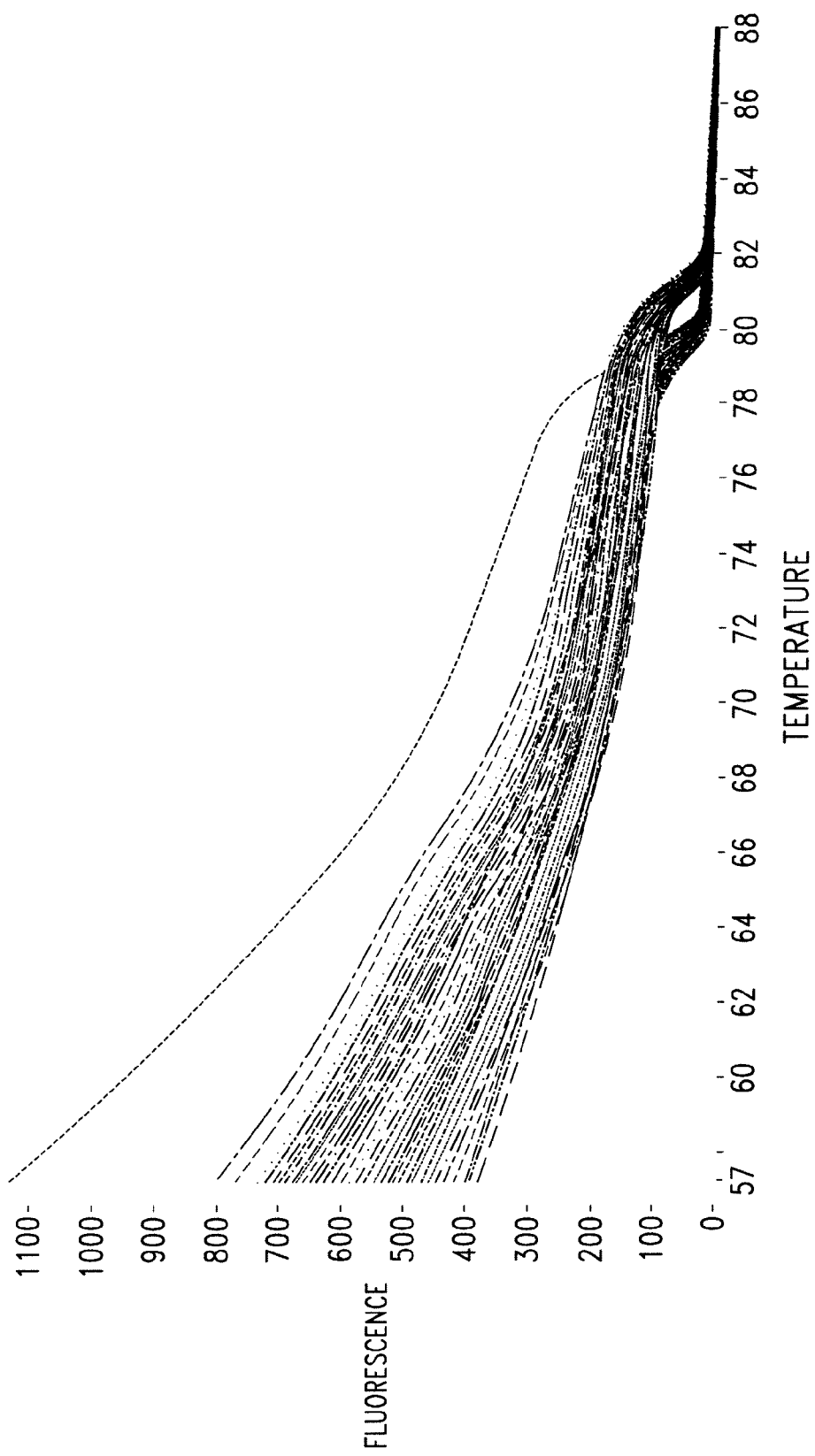

The LightScanner melting instrument measured and recorded the fluorescence as a function of temperature. The raw melting curve result of the procedure is shown in FIG. 5A. The negative derivative of the melting curve of FIG. 5A was calculated and is shown in FIG. 5B. A representative diagram of the 384 well plate is shown in FIG. 5B along with the clustering of the genotypes. Background removal has not been performed, and the clustering performed did not correctly genotype several of the samples tested (compare 384 well plate to that in FIG. 5D).

Figure 5C:
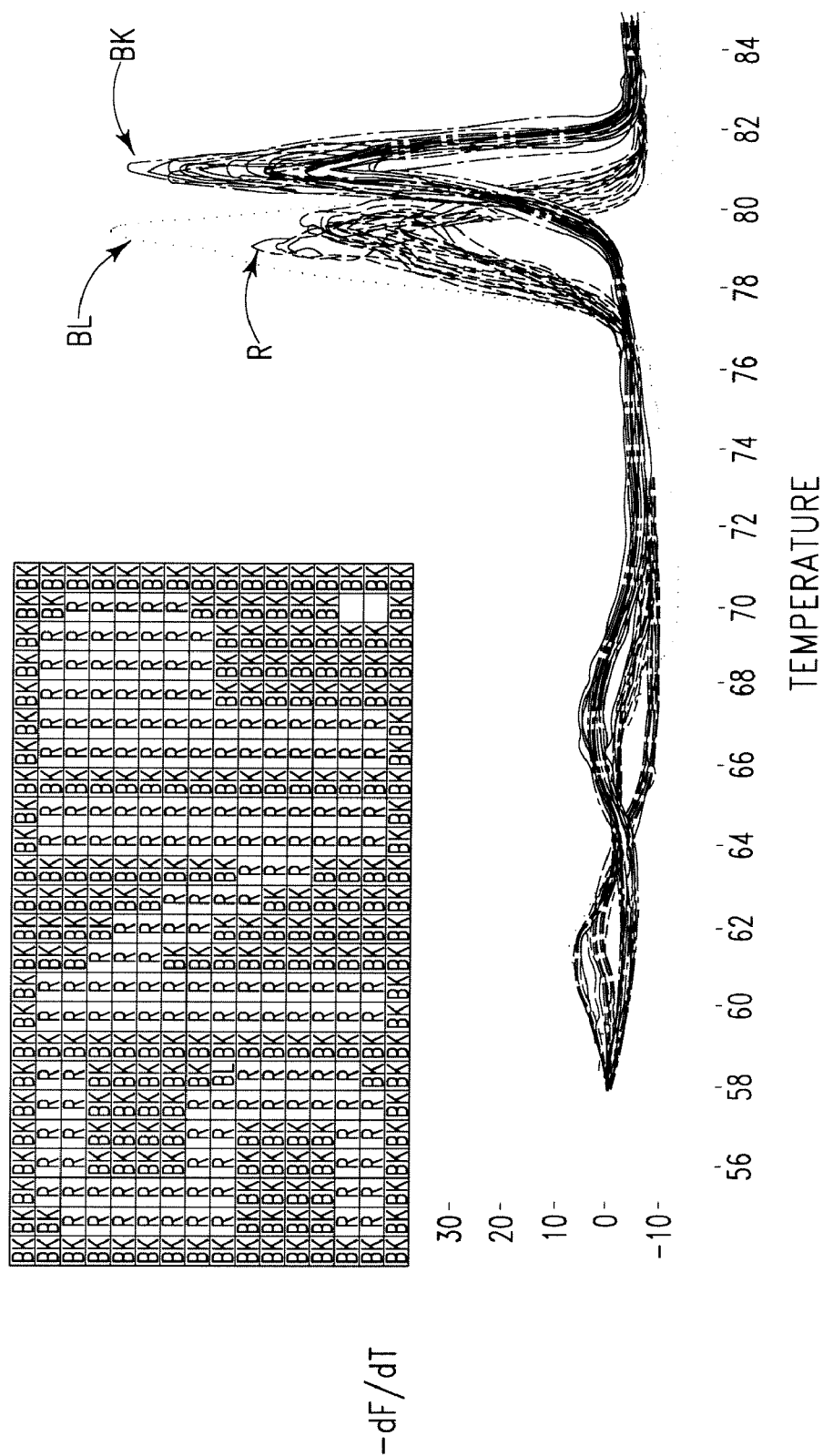

A linear correction function was performed on the derivative plot of FIG. 5B and is shown in FIG. 5C. A representative diagram of the 384 well plate is shown in FIG. 5C along with the clustering of the genotypes. It is clear from the 384 well plate that the clustering performed after the linear correction did not correctly genotype several of the samples tested. The linear correction performed on the derivative melting curve data includes deleting the end to end slope by subtracting a linear function.

Figure 5D:
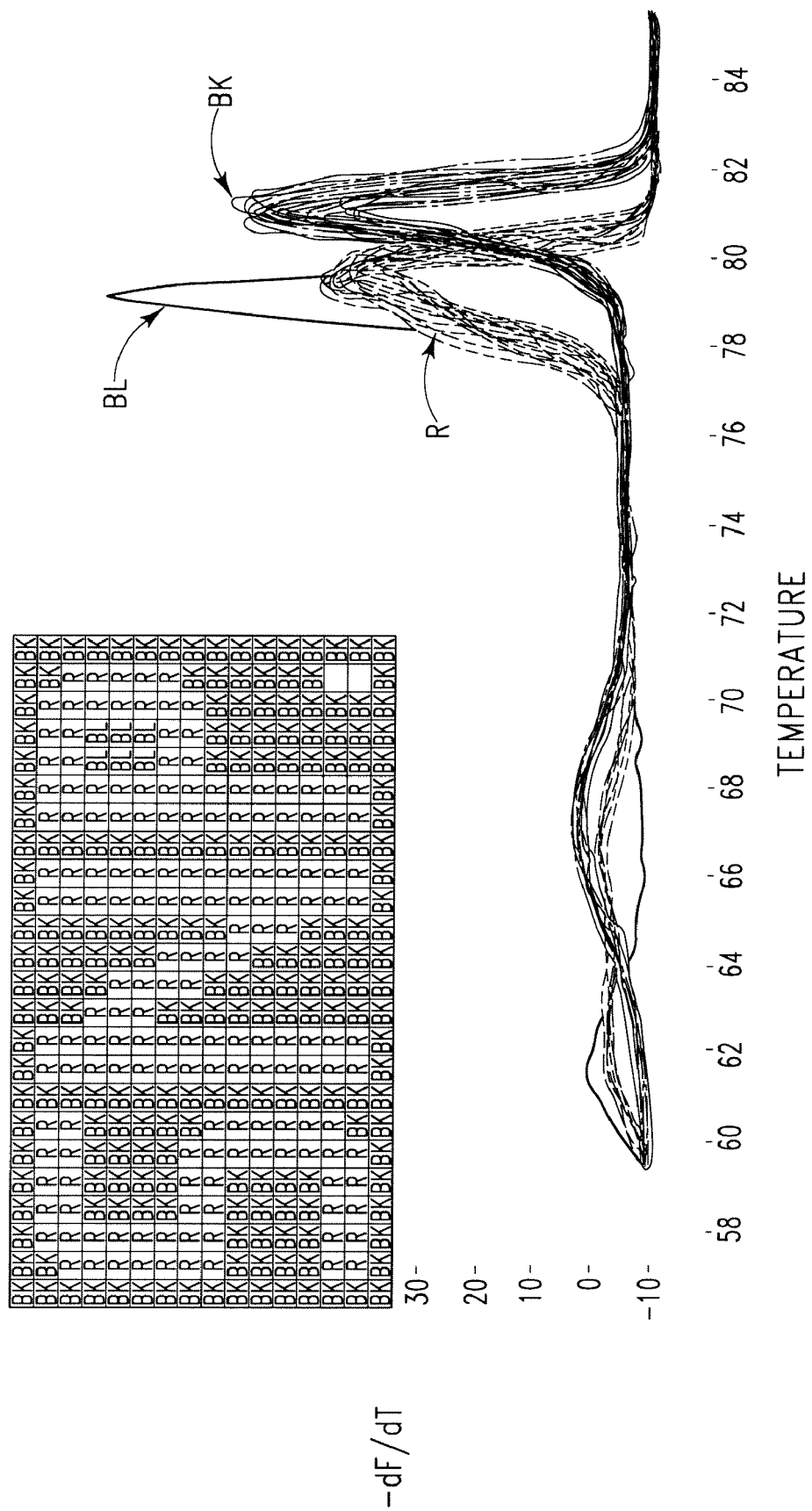

FIG. 5D represents the derivative melting curve data of FIG. 5B after exponential background subtraction has been performed on the data set. Only after the exponential background subtraction is the correct clustering of genotypes obtained. The accuracy of the genotype clustering is visible within the 384 well plate (FIG. 5D), where the letters "S-N-P" are spelled out indicating genotypes by plate position, and the proper identification is visible for both the amplicon and probe region of the Factor V Leiden gene target.

EXAMPLE 3

Factor V Leiden (96 Well Plate) Derivative Clustering of Probe Only

Human Factor V Leiden genomic DNA samples representing different Factor V Leiden genotypes were amplified in an ABI 9700 with 10 µl reaction volume and 12 µl oil overlay. The assay included a Factor V Leiden amplicon and an unlabeled probe, as described above in Example 2, in the presence of 1× LCGreen Plus®. The resultant PCR samples were heated from 58° C. to 88° C. at 0.1° C./s in a LightScanner melting instrument using a 96 well reaction plate. The total melting procedure required approximately 5 minutes for completion.

Figure 6A:
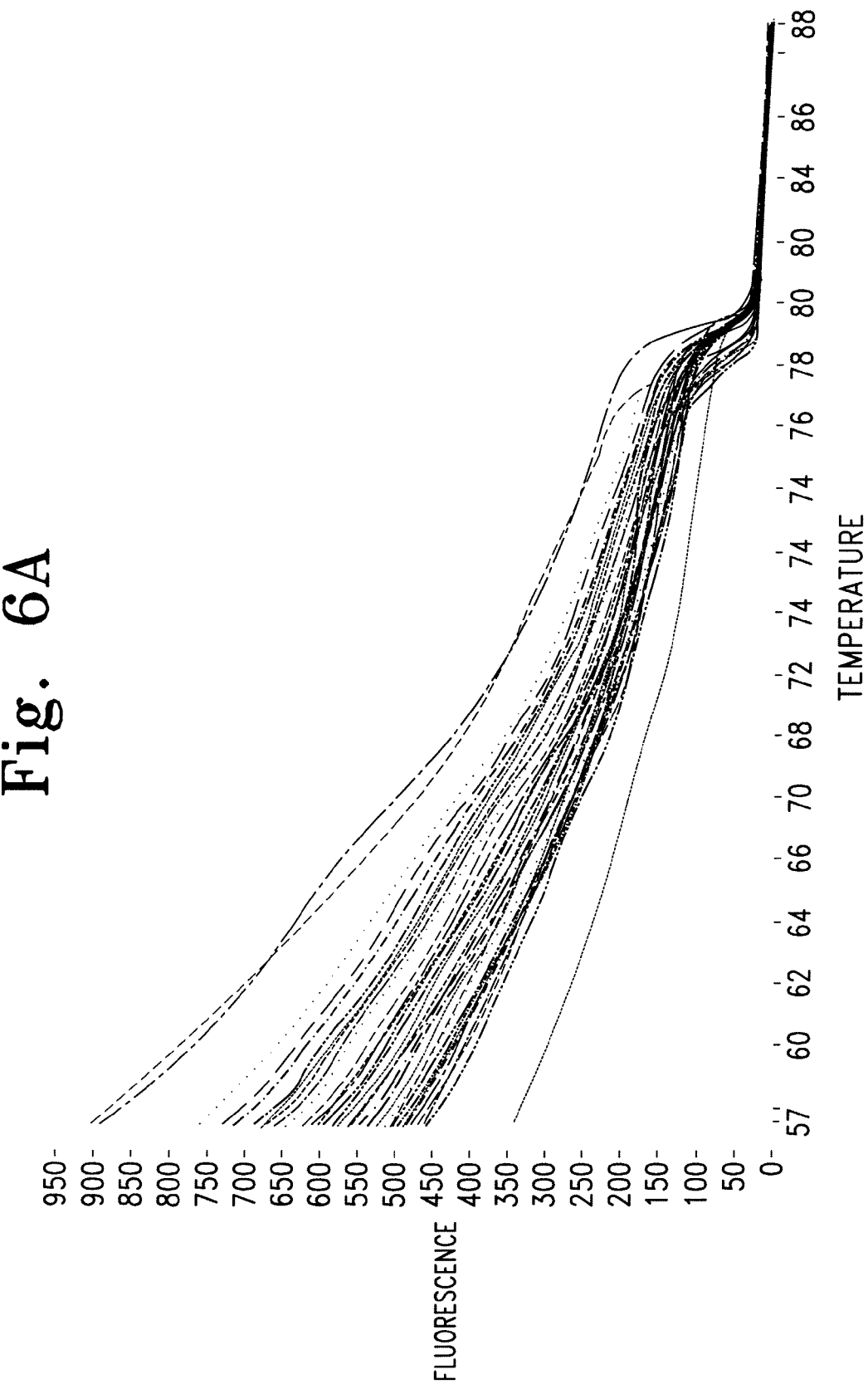
Figure 6B:
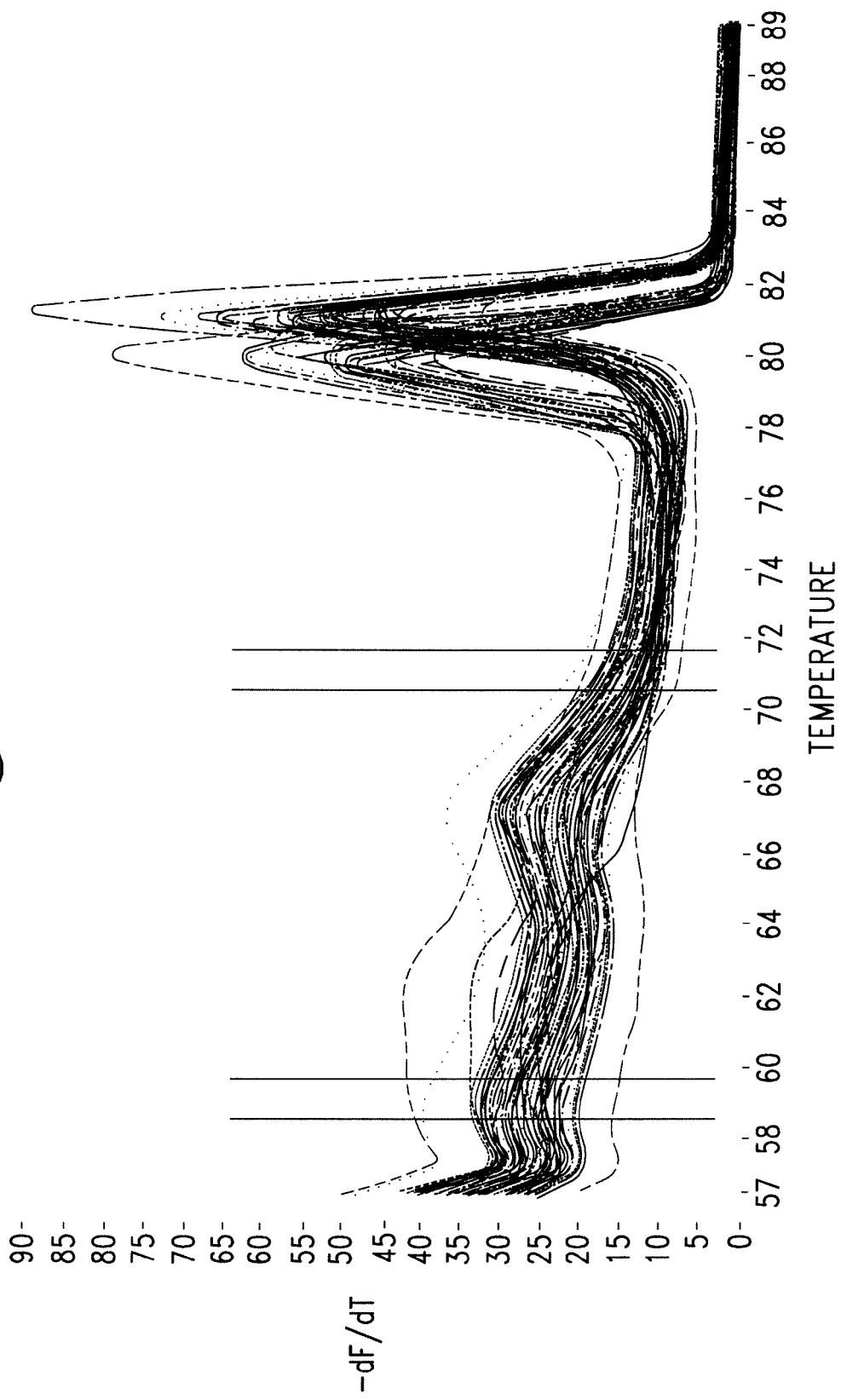
Figure 6D:
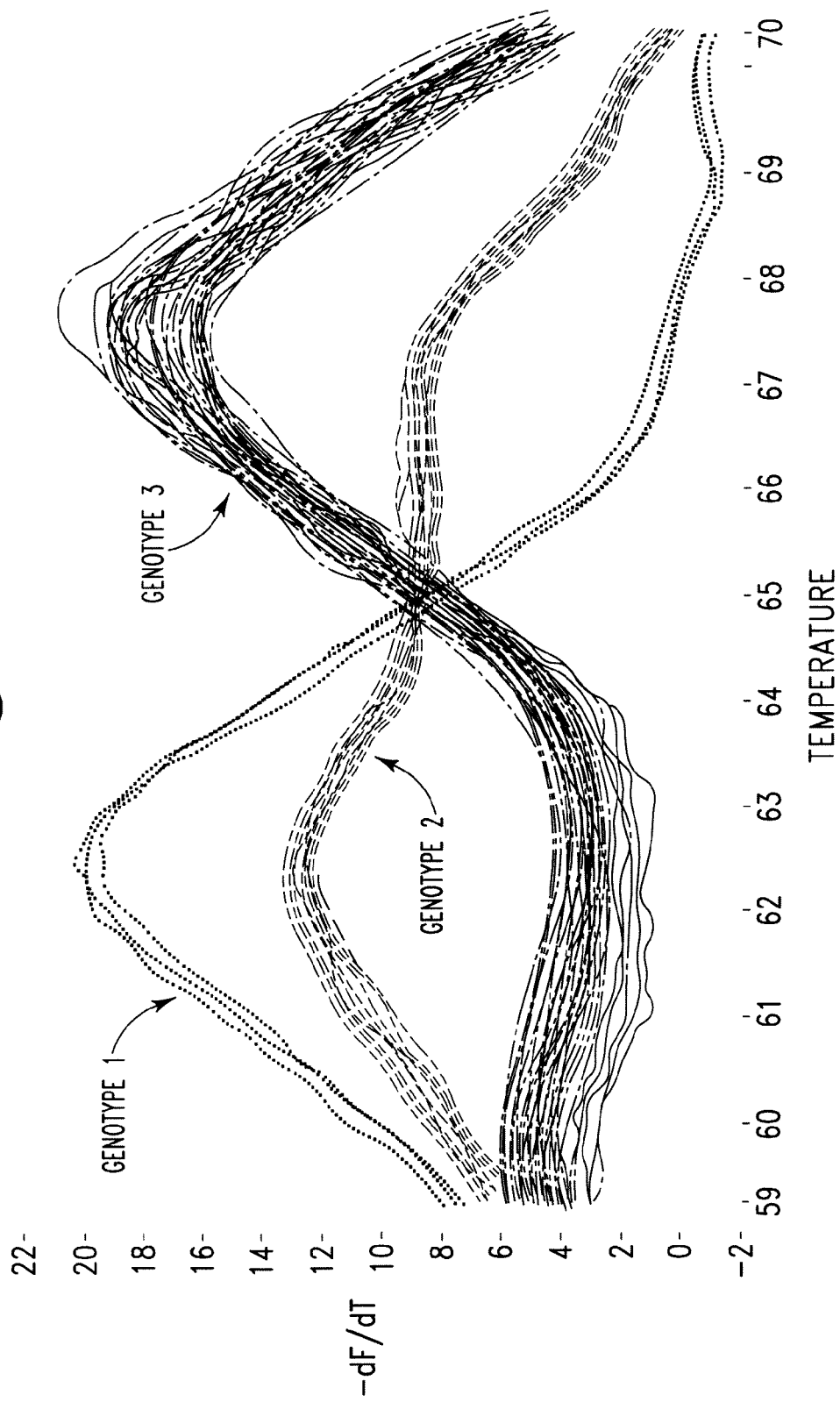

The LightScanner melting instrument measured and recorded the fluorescence as a function of temperature. The raw melting curve result of the procedure is shown in FIG. 6A. A negative derivative plot as a function of temperature was performed from the melting curve data of FIG. 6A and is shown in FIG. 6B. Two sets of vertical cursor lines are present at approximately 59° C. and 60° C., and 71° C. and 72° C. respectively. The exponential background subtraction technique slopes are generated using these cursor lines. Following the automatic calculation and fitting, the exponential background is subtracted from the raw negative derivative plot. The result of the exponential background subtraction specific to the probe region is shown in FIG. 6C. Though the vertical slope cursors are located on either side of the probe region, the exponential used for the probe region may also be used for the amplicon region. In fact, the absolute location of where the slopes are obtained is not determinative of the exponential, so long as the slopes are found at positions where no melting of the sample occurs. The probe region data (FIG. 6C) is automatically clustered by the genotype clustering function. The nucleic acid samples from the 96 well plate are clustered into three genotypes and shown in FIG. 6D.

Regarding Examples 4 and 5 the following procedures and instruments were used. Human genomic DNA of known Factor V Leiden genotype samples and heterozygous genomic DNA samples with selected cystic fibrosis mutations were used for analysis.

Predicted probe $T_m$s were lower than observed $T_m$s, perhaps because of dye stabilization. The melting temperature of different probe/allele duplexes was adjusted by probe length, mismatch position, and probe dU vs dT content. Extension of unlabeled probes during PCR was prevented by incorporating a 3'-phosphate during synthesis. Alternatively, other 3'-blocking mechanisms may be employed, illustratively by providing an additional two base mismatch to the 3'-end of the probe. When a 5'-exonuclease negative polymerase is used, probes should be designed to melt lower than the PCR extension temperature.

Primer asymmetry, illustratively at ratios of 1:5 to 1:10, may be used to produce sufficient double stranded product for amplicon melting and enough single stranded product for probe annealing. PCR for Factor V performed in 384-well format used 5 µl volumes, and included 20 ng of genomic DNA in 50 mM Tris, pH 8.3 with 3 mM MgCl.sub.2, 0.2 mM each dNTP, 500 µg/ml BSA, 1× LCGreen® PLUS (Idaho Technology), 0.2 U KlenTaq1™ (AB Peptides), and 70 ng TaqStart™ antibody (Clontech). PCR was performed in a 9700 thermal cycler (ABI) with an initial denaturation at 94° C. for 10 s, followed by 50 cycles of 94° C. for 5 s, 57° C. for 2 s, and 72° C. for 2 s. After PCR, the samples were heated to 94° C. for 1 s and then cooled to 10° C. before melting.

PCR for amplification of CFTR exons 10 and 11 was performed in 10 µl volumes and included 50 ng of genomic DNA in 50 mM Tris, pH 8.3 with 2 mM MgCl.sub.2, 0.2 mM each dNTP, 500 µg/ml BSA, 1× LCGreen I (Idaho Technology) and 0.4 U Taq polymerase (Roche). The PCR was performed in capillaries on a LightCycler (Roche) with an initial denaturation of 95° C. for 10 seconds followed by 45 cycles of 95° C. for 1 s, 54° C. for 0 s, and 72° C. for 10 s. After amplification, the samples were heated to 95° C. for 0 s and rapidly cooled to 40° C. before melting.

When the nucleic acid samples were amplified on 384-well plates, melting acquisition was performed on a prototype version of the LightScanner® (Idaho Technology). The standard 470 nm light-emitting diodes were replaced with 450 nm light-emitting diodes (Bright-LED Optoelectronics). In addition, the optical filters were changed to 425-475 nm excitation and 485 nm long-pass emission filters (Omega Optical). The plate was heated from 55 to 88° C. at 0.1° C./s with a 300 ms frame interval, 15 ms exposure and 100% LED power, resulting in about 25 points/° C.

Melting of CFTR exons was performed on the HR-1 high-resolution melting instrument (Idaho Technology) with 24-bit acquisition of temperature and fluorescence. After PCR on the LightCycler, each capillary was transferred to the HR-1 and melted from 50° C. to 90° C. with a slope of 0.3° C./s, resulting in 65 points/° C.

Melting curves can be analyzed on any suitable software known in the art. An exemplary software package for implementing the melting analysis methods of the various embodiments of the present invention is LabVIEW (National Instruments). Normalization and background subtraction was first performed by fitting an exponential to the background surrounding the melting transitions of interest. Derivative plots of probe melting transitions were obtained by Salvitsky-Golay polynomial estimation. Melting curves of PCR products were compared on difference plots of temperature-overlaid, normalized melting curves. The normalized melting curves were temperature-overlaid (to eliminate slight temperature errors between wells or runs) by selecting a fluorescence range (illustratively low fluorescence/high temperature, typically 5-10% fluorescence) and shifting each curve along the X-axis to best overlay a standard sample within this range. Difference plots of temperature-overlaid, normalized curves were obtained by taking the fluorescence difference of each curve from the average wild type curve at all temperature points. These analytical methods have been previously applied to mutation scanning and HLA matching.

Agglomerative, unbiased hierarchical clustering of melting curve data was performed by previous methods, custom programmed in LabVIEW. The distance between curves was taken as the average absolute value of the fluorescence difference between curves over all temperature acquisitions. The number of groups was automatically identified by selecting the largest ratio of distances between consecutive cluster levels. The clustering methods represent less accurate means for clustering genotypes than the novel clustering methods described herein (FIGS. 9A-D).

EXAMPLE 4

CFTR Scanning and Genotyping

Various exons of the cystic fibrosis transconductance regulator (CFTR) gene have been chosen to demonstrate simultaneous scanning and genotyping of multiple variants.

Figure 7A:
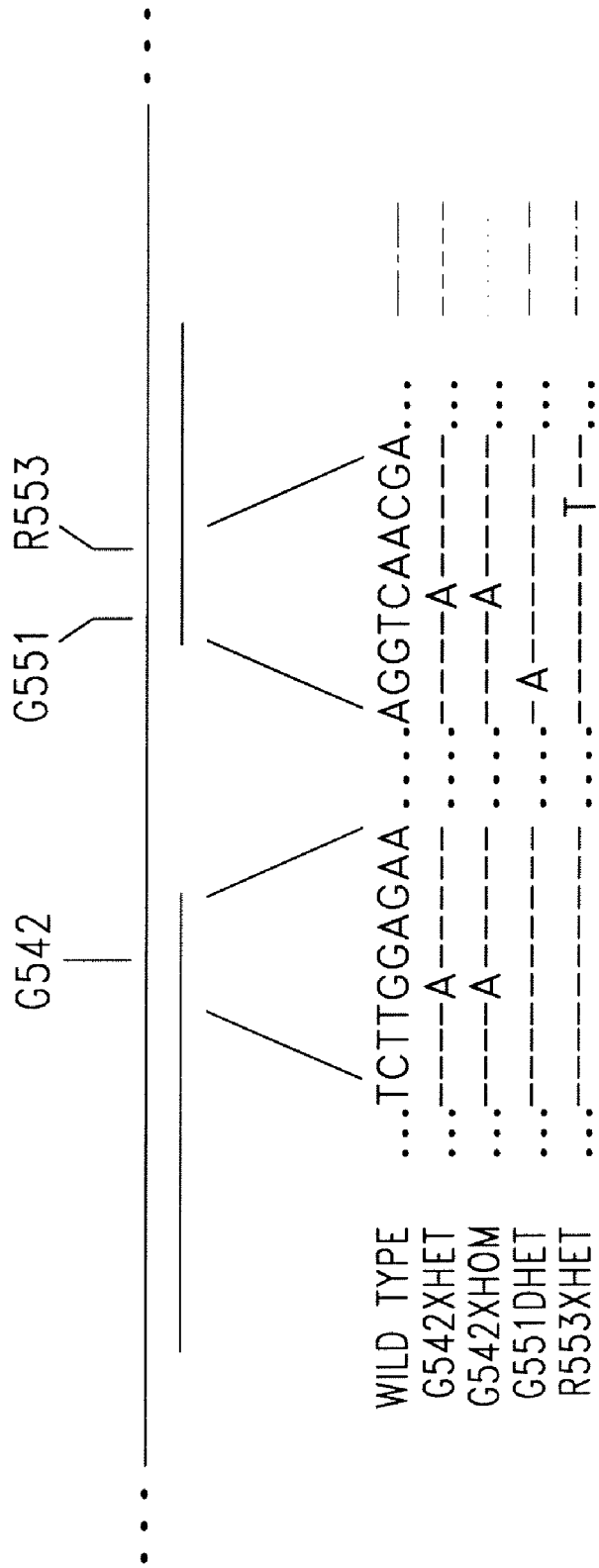
Figure 7C:
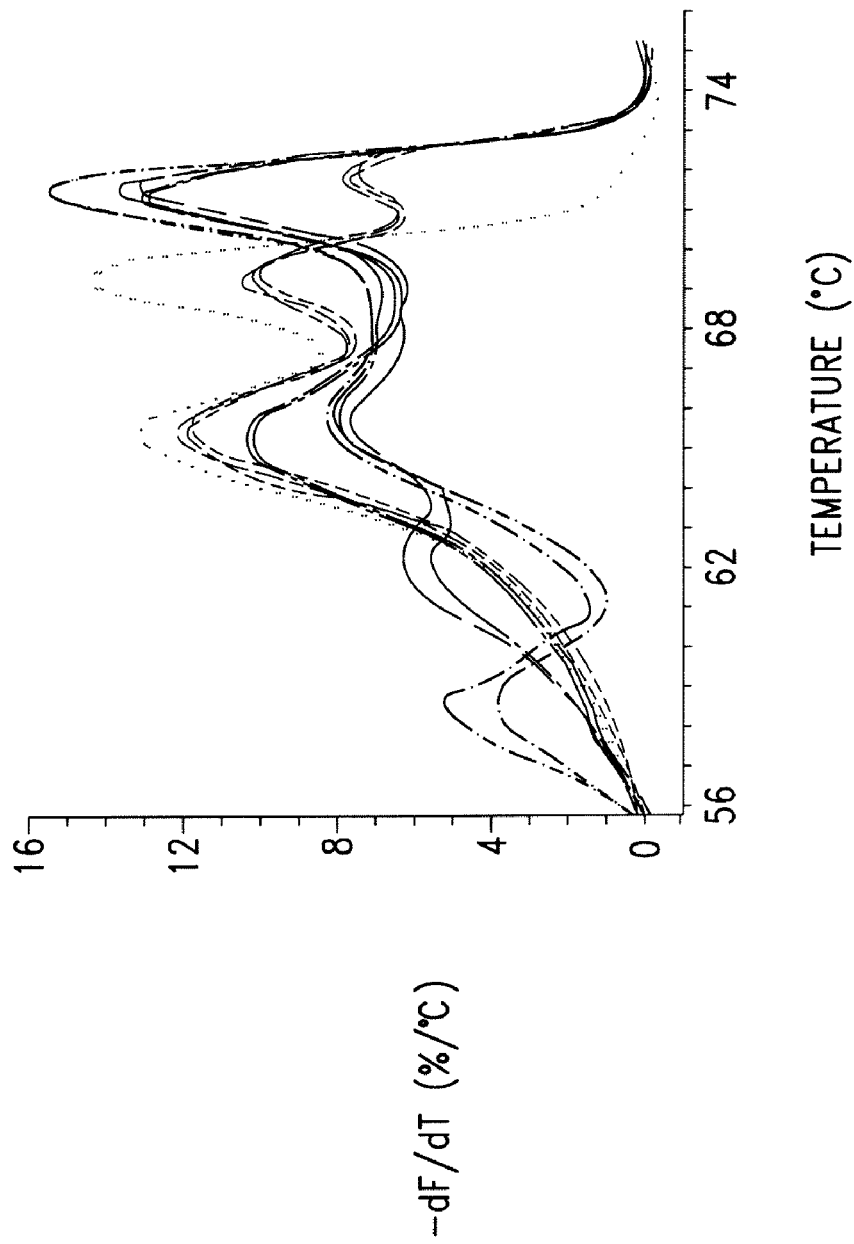
Figure 7D:
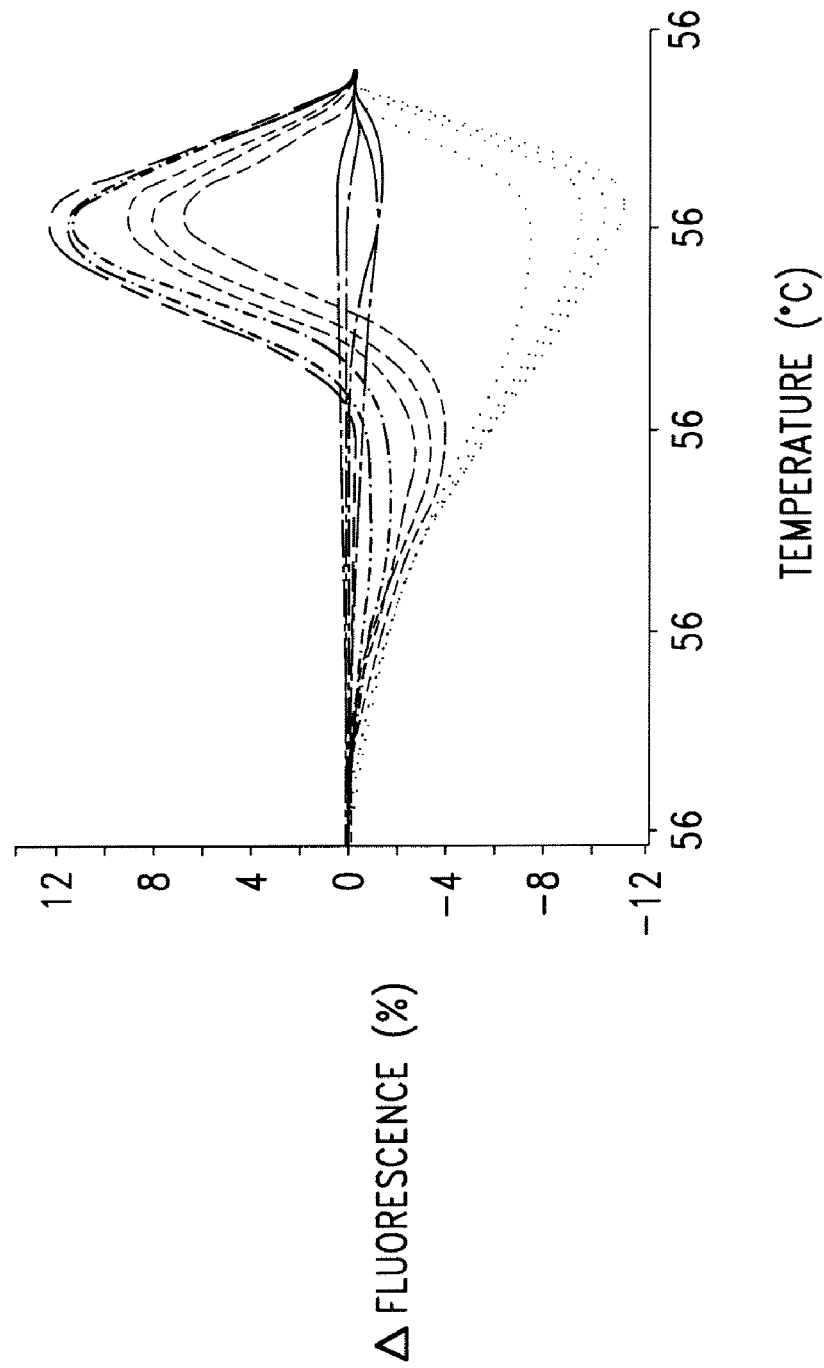

Three SNPs in two regions of exon 11 of the CFTR gene were analyzed with two unlabeled probes, sequences in part TCTTGGAGAA (SEQ. ID NO:5) and AGGTCAACGA (SEQ. ID NO:6). Two of the mutations were only six bases apart, allowing one of the probes to cover both mutations (FIG. 7A). Five replicates of each genotype were amplified and analyzed. The normalized melting curves after EBS (FIG. 7B) show regions of probe melting (56-74° C.) and PCR product melting (80-83° C.). On casual observation, it is not clear from the normalized melting curve what information can be extracted. However, when the probe region is displayed as a derivative plot (FIG. 7C), the melting transitions of all common alleles under both probes are apparent. Both unlabeled probes were matched to the wild type sequence, but one of the probes was made shorter and contained dU instead of dT to decrease its melting temperature. The more stable probe covered a single SNP, resulting in two alleles being separated by $T_m$, both being more stable than all alleles of the less stable probe. The less stable probe covered two SNPs, resulting in three peaks for common genotypes. The specific mismatch and its position within the probe affect duplex stability, allowing probe design that distinguishes multiple alleles. A difference plot of the PCR product melting transition is shown in FIG. 7D. The heterozygous, wild type, and homozygous mutant samples are clearly different. However, it is difficult to distinguish between different heterozygotes by PCR product melting alone. Unbiased hierarchal clustering grouped all heterozygotes together (data not shown). The three heterozygotes are all in the same SNP class (12), resulting in the same heteroduplex mismatches (C:A and T:G) and homoduplex matches (C:G and A:T). Although predicted stabilities of all three heterozygotes using nearest neighbor thermodynamics (13, 14) are not identical, definitive genotyping required the use of probes. The strength of product melting is to easily identify the presence of heterozygotes, while unlabeled probes further discriminate between heterozygotes and more easily identify homozygous variants. As illustrated with this example, combining both genotyping and scanning results in the display of both amplicon (PCR product) and unlabeled probe melting transitions.

EXAMPLE 5

CFTR Genotyping

Figure 8B:
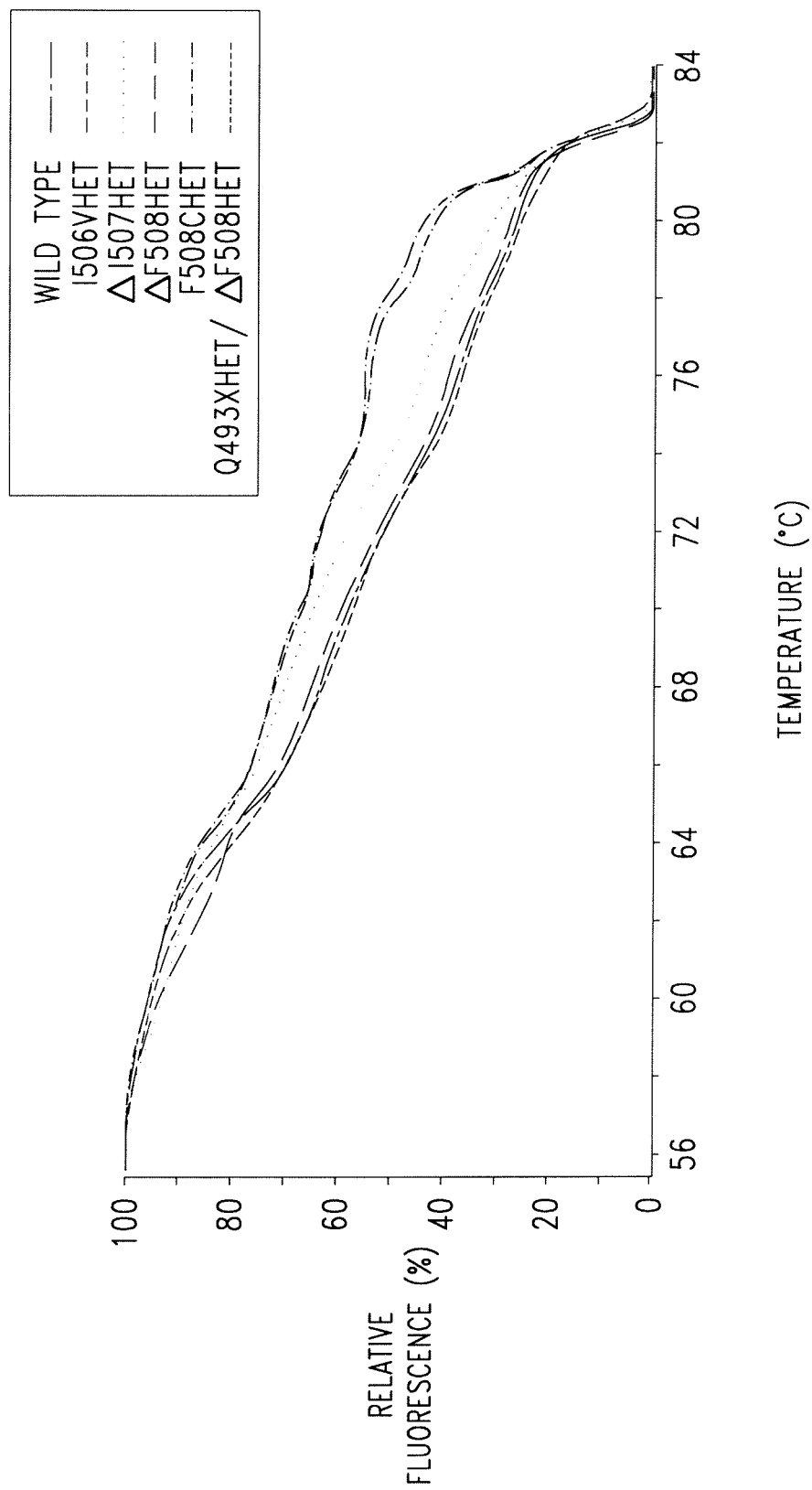
Figure 8C:
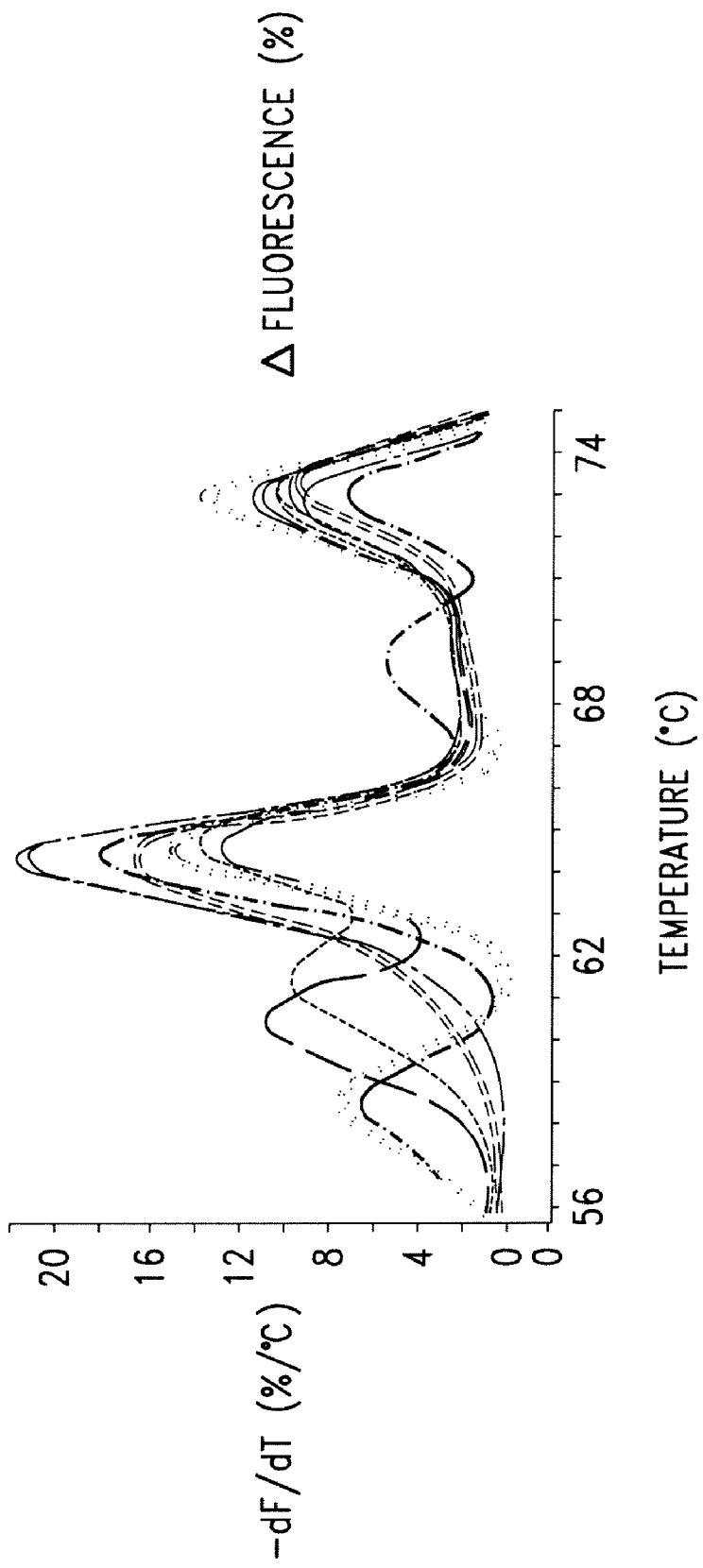
Figure 8D:
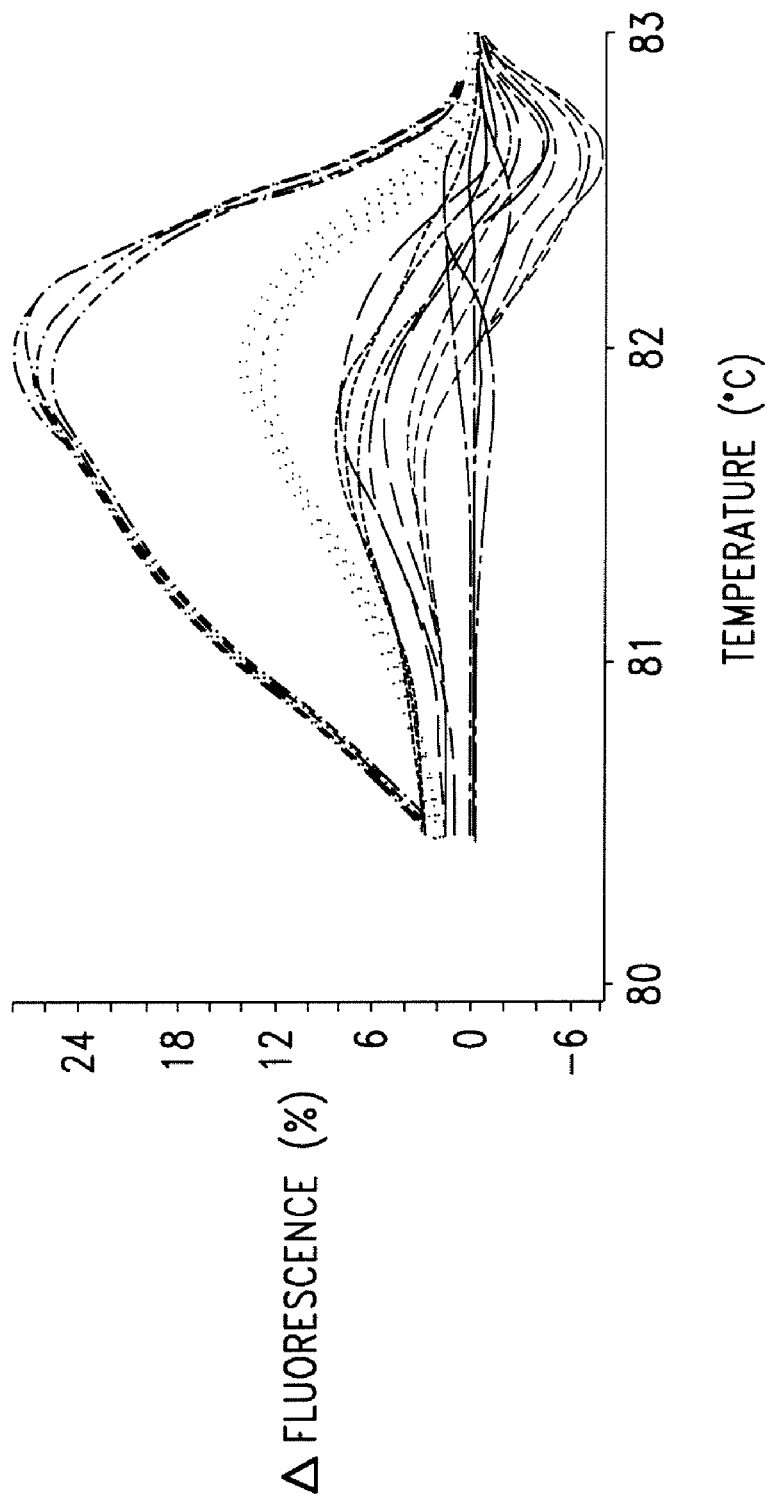

Three SNPs and two deletions within exon 10 of the CFTR gene were also analyzed with two unlabeled probes. The probe with the higher $T_m$, sequence in part TTCTCAGTTT (SEQ. ID NO:7), covered a single SNP, while the probe with the lower $T_m$, sequence in part TATCATCTTTG (SEQ. ID NO:8), covered two SNPs and two deletions (FIG. 8A). The normalized melting curves after EBS (FIG. 8B) show regions of low temperature probe (56-67° C.), high temperature probe (67-75° C.), and PCR product (80-83° C.) melting. When the probe regions are displayed as a derivative plot (FIG. 8C), all five heterozygous genotypes follow unique paths that distinguish them from wild type and each other. Four of the heterozygotes show resolved peaks, while one is identified by a broad peak resulting from a relatively stable mismatch (an A:G mismatch near one end of the probe in an AT-rich region). Allele discrimination does not require a unique $T_m$ for each allele, only that the curves are different in some region of the melting transition. A difference plot of the PCR product melting transition is shown in FIG. 8D. The double heterozygote shows the greatest deviation from wild type because two mismatches are present within the PCR product. The four single heterozygotes are all easily distinguishable from wild type. In contrast to exon 11, all heterozygotes could be genotyped by either PCR product or probe melting. Consideration of both regions often provides independent confirmation of genotype.

EXAMPLE 6

Whole Amplicon Genotyping of β Globin

β globin presents a gene target with known SNPs that are important for the analysis of hemoglobinpathies, most notable are the HbC and HbS mutations. Human genomic DNA samples of different β globin genotypes were amplified in a Roche LightCycler using 10 µl reaction volumes. 1× LCGreen® from Idaho Technology was used in PCR to amplify a 45 bp amplicon: 5'-CCATGGTGCACCTGACTC-CTGAGGAGAAGTCTGCCGTTACTGCCC-3' (SEQ. ID NO:9). The PCR product samples were heated from about 72° C. to about 88° C. at 0.3° C./s in the HR-1 melting instrument. The time required for melting is about 60 seconds.

Figure 9A:
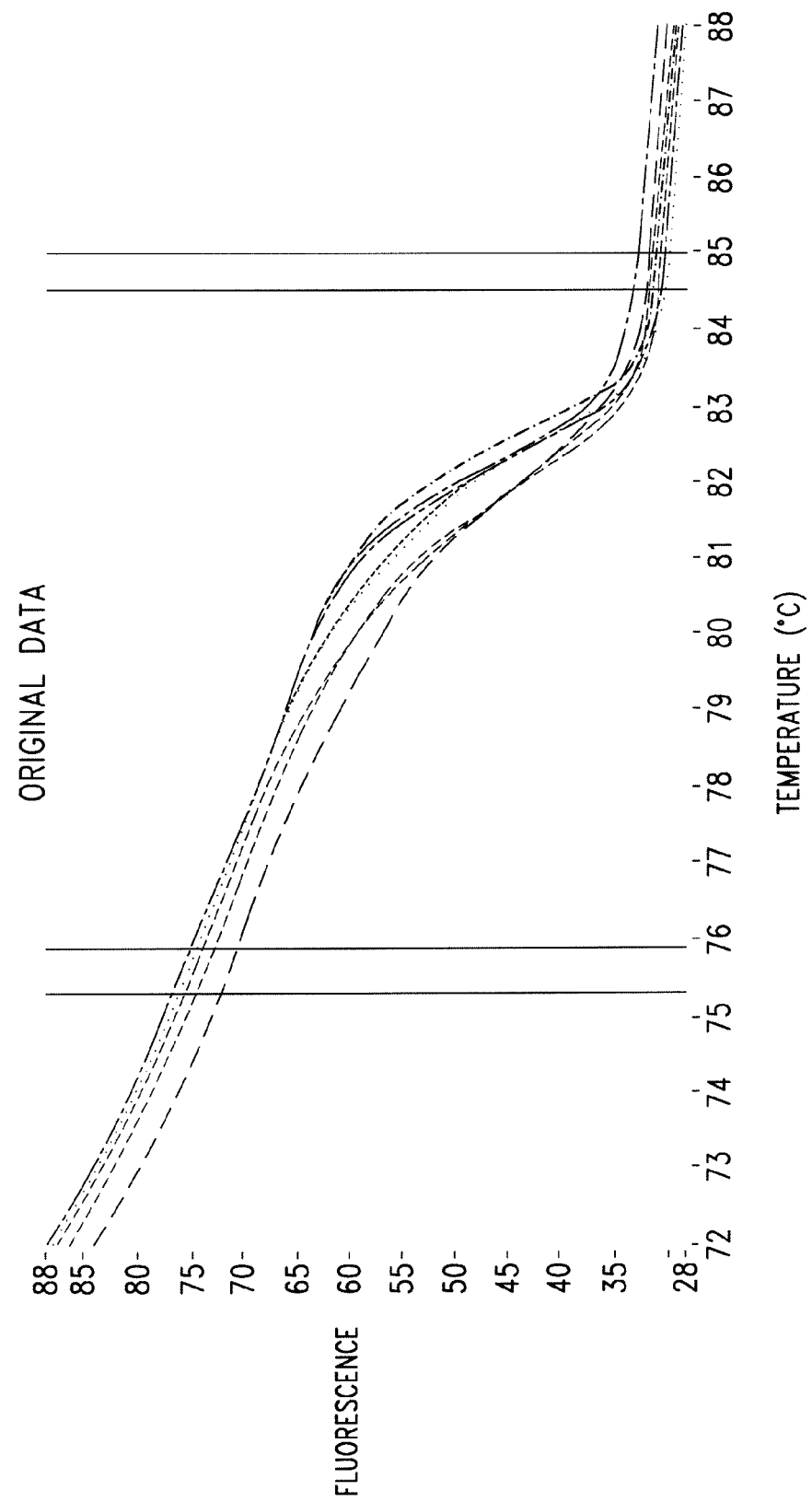
FIG. 9A shows the original melting curves for a β-globin amplicon including the HbS and HbC SNP loci.
Figure 9B:
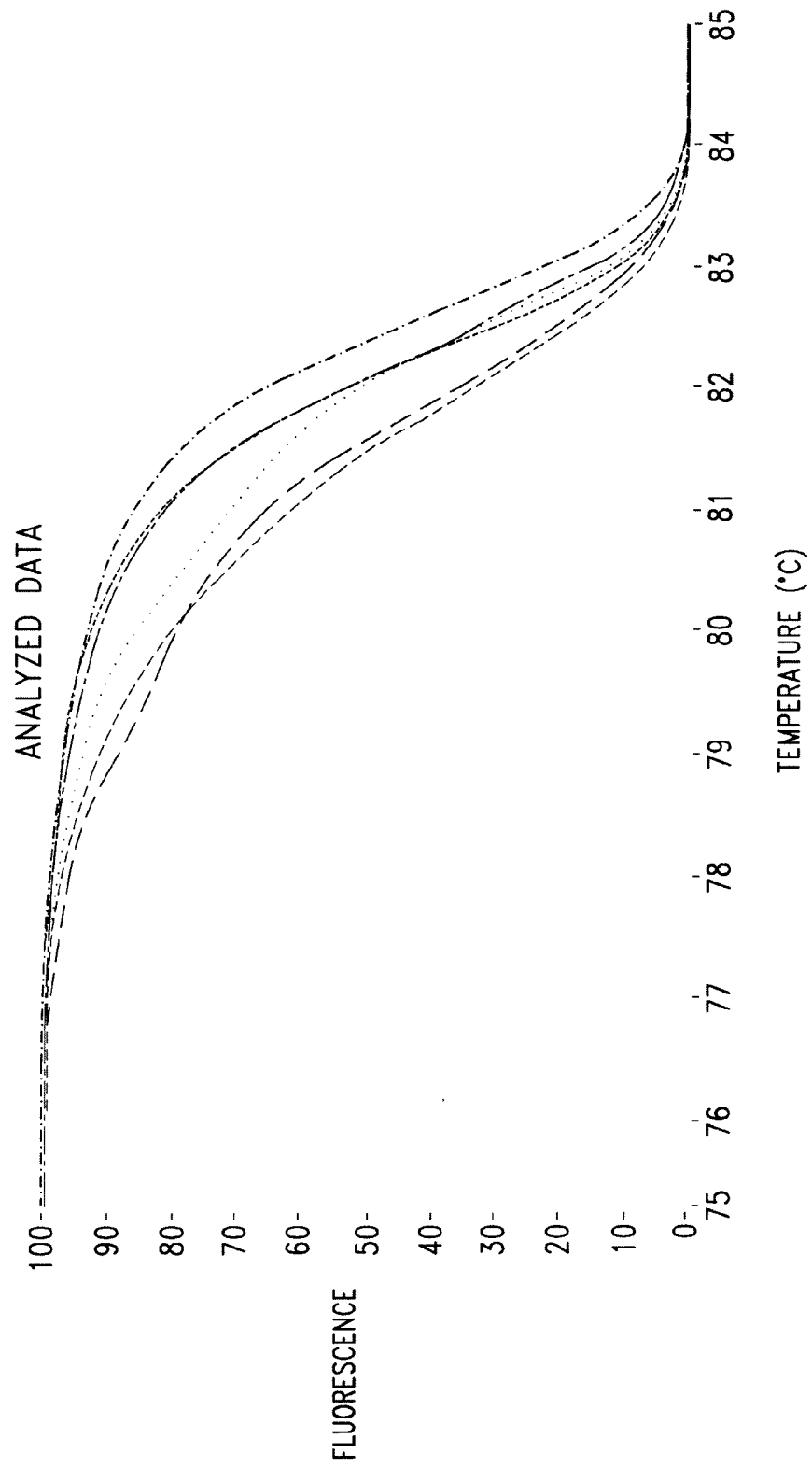
FIG. 9B shows the melting curve data after exponential background subtraction.

The HR-1 melting instrument measured and recorded the fluorescence of the samples as a function of temperature. The raw melting curve for the whole β globin amplicon is shown in FIG. 9A. The raw melting curve for the whole β globin amplicon is then normalized by the exponential background subtraction method described herein, which results in a melting curve that is the relative fluorescence of the samples as a function of temperature in FIG. 9B. The genotype clustering function is performed on the normalized melting curves from FIG. 9B. FIG. 9C shows the clustered genotypes of the normalized melting curves from FIG. 9B.

EXAMPLE 7

Factor V Leiden Wild Type Difference Plot Analysis

Human Factor V Leiden genomic DNA samples representing 60 different Factor V Leiden wild types were amplified in an ABI 9700 with 10 µl reaction volume and 12 µl oil overlay. The assay included a Factor V Leiden amplicon and an unlabeled probe, as described above in Example 2, in the presence of 1× LCGreen Plus®. The resultant PCR samples were heated from 58° C. to 88° C. at 0.1° C./s in a LightScanner melting instrument using a 96 well reaction plate. The total melting procedure required approximately 5 minutes for completion.

Figure 10A:
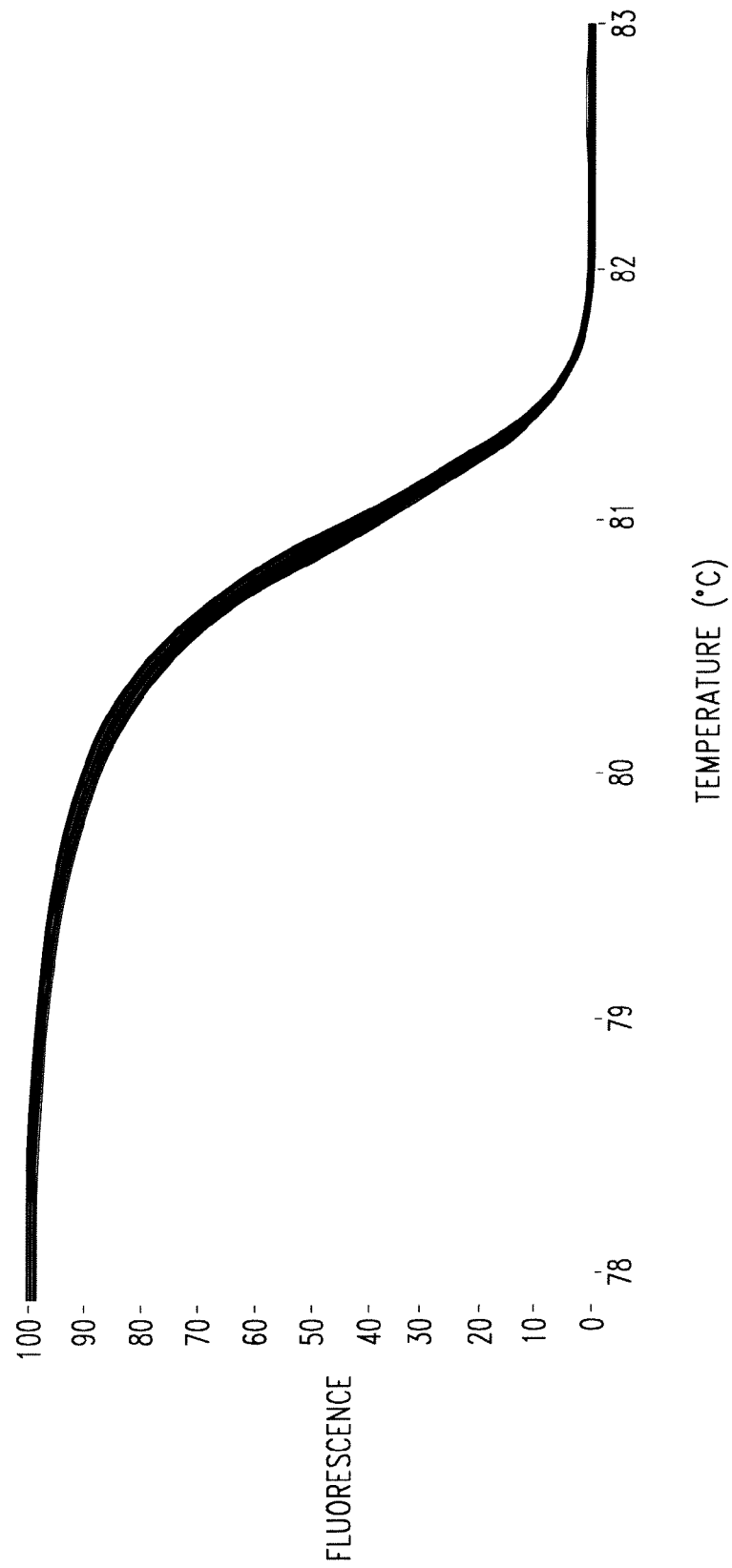
FIGS. 10A-C show high resolution melting curves of 60 sample wild types at the Factor V Leiden locus.

The LightScanner melting instrument measured and recorded the fluorescence as a fraction temperature. Execution of various difference plot functions provides a fluorescence difference value as a function of temperature. The melting curves for 60 Factor V Leiden wild types is shown in FIG. 10A after performing the exponential background subtraction function. The normalized melting curve appears as one thick black curve, which is characteristic of the substantial similarities of the 60 wild type samples.

Figure 10B:
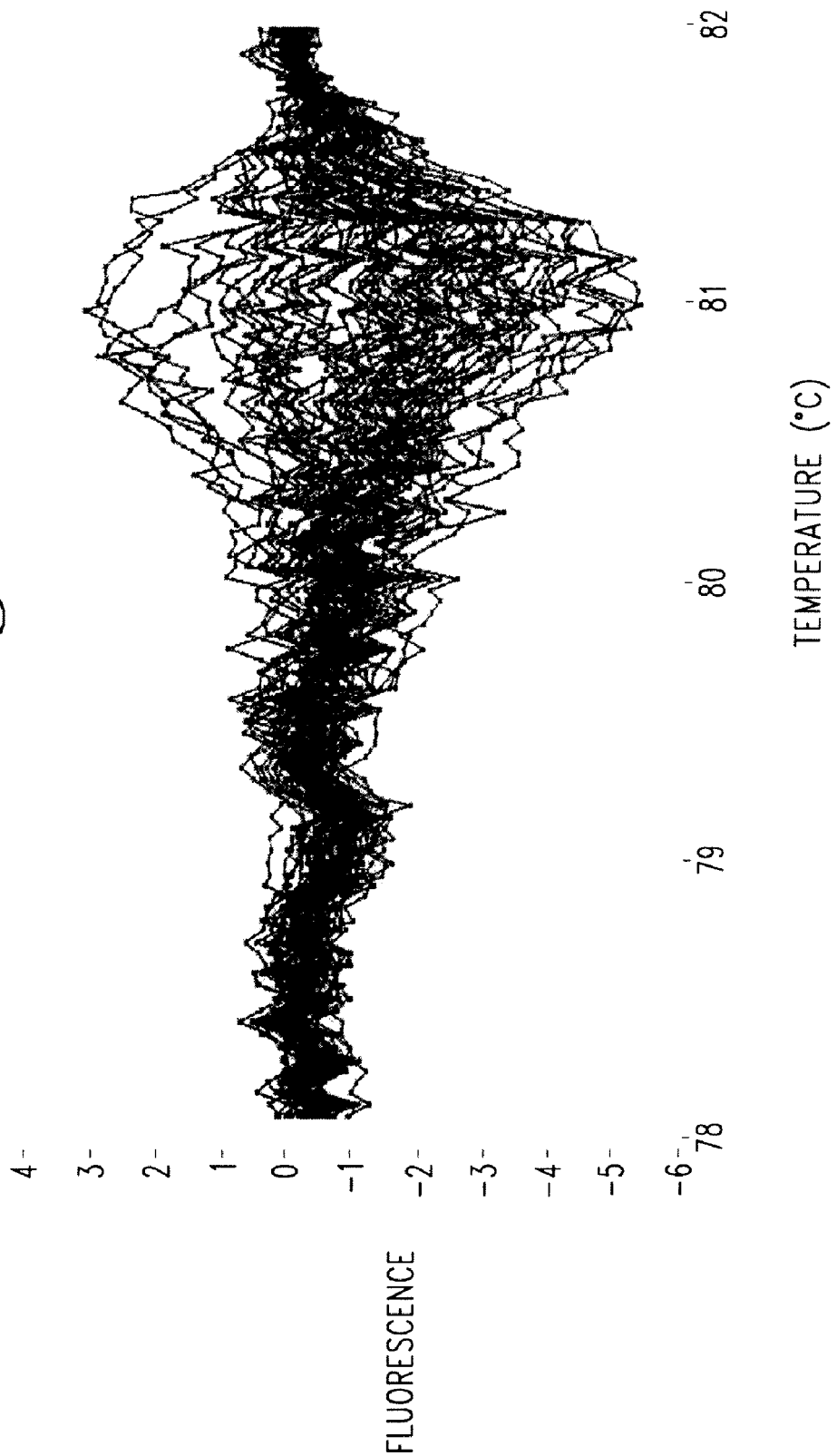

FIG. 10B represents the graphical result of the previous vertical difference plot technique, which is plot as the vertical fluorescence difference between the 60 wild type samples as a function of temperature. This previous vertical difference plot technique presents an interesting artifact when the melting curves have a sufficiently steep slope. The artifact manifests as a "bubble" approximately between 80.25° C. and 81.5° C. (FIG. 10B), which is the steepest portion of the raw data melting curve slope.

Figure 10C:
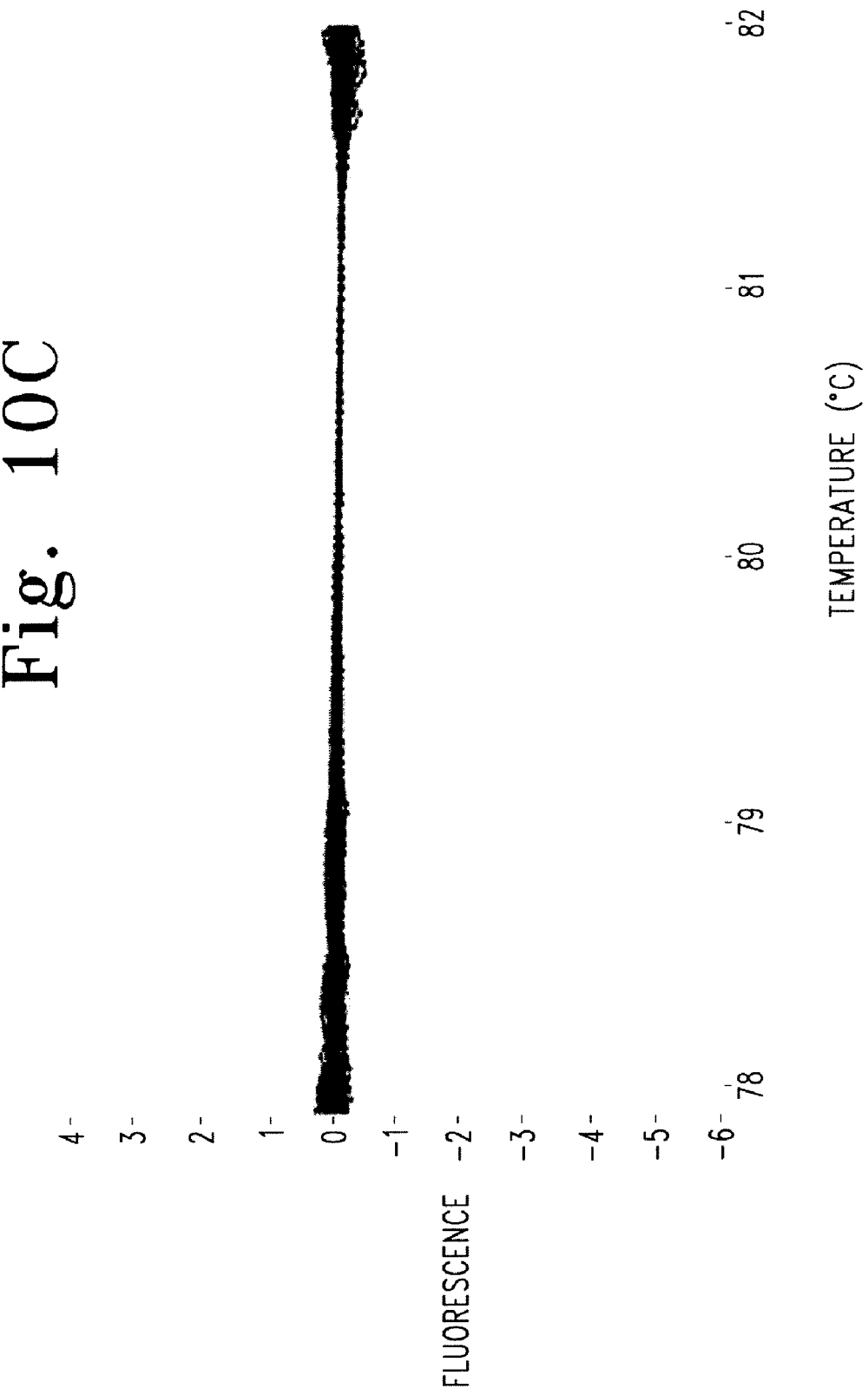

The artifact of the vertical difference plot represents the artificial amplification of small differences between the 60 wild type samples. FIG. 10C represents the results of the orthogonal difference plot function. As the difference plot function is designed to accurately measure the difference between the samples, the close proximity of the fluorescence difference plotted as a function of temperature is indicative of the significant similarity among the 60 wild type samples (FIG. 10C). The difference fluorescence vs. temperature plot of the 60 wild types appears as a single thick line approximately centered upon zero fluorescence difference.

Figure 11:
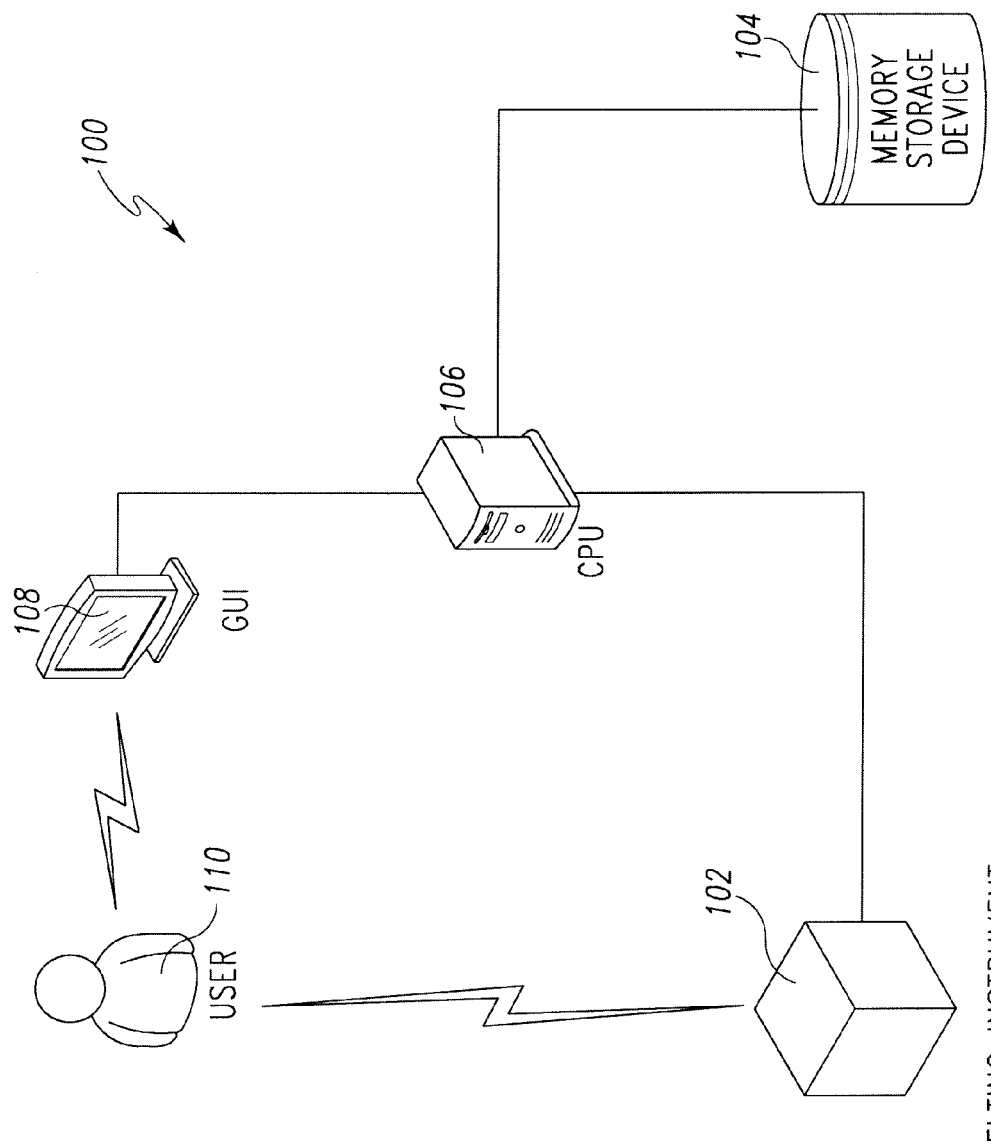
FIG. 11 is a block diagram of an illustrative example of the nucleic analyzing system.

Referring to FIG. 11, it is contemplated that the embodiments of the present invention can be implemented on a computer system 100. The computer system 100 comprises a nucleic acid melting instrument 102, a memory storage device 104 and a central processing unit (CPU) 106. The memory storage device 104 and the CPU 106 may be integral (not shown) within the housing of the melting instrument 102 or may be provided externally (FIG. 11), illustratively as a laptop or desktop computer. The system 100 alternatively can include a graphical user interface (GUI) 108 for viewing, manipulating, and analyzing the high resolution melting curve. The user 110 may interface directly with the melting instrument, GUI, or any other aspect of the system 100. The memory storage device 104 includes computer readable code that is the exact embodiment or equivalent to the embodiments of the invention described herein. The computer readable code includes instructions for performing the methods described herein and is executed by any suitable central processing device known in the art. Software is available with most melting instruments and often allows visualization of probe and product melting transitions as derivative peaks, usually by Salvitsky-Golay polynomial estimation of the slope at each point. Various central processing devices execute different coding languages, and coding languages are often distinct in their structure and execution, such that it is contemplated that variations in the methods and equations described herein are nonetheless within the spirit and scope of the invention. The various embodiments are given by example and the scope of the present invention is not intended to be limited by the examples and equations provided herein. Although the invention has been described in detail with reference to preferred embodiments, variations and modifications exist within the scope and spirit of the invention as described and defined in the following claims.

---

What is claimed is:

1. A method for clustering melting profiles of a plurality of nucleic acid samples, comprising measuring the fluorescence of each nucleic acid sample as a function of temperature to produce a respective raw melting curve for each respective nucleic acid sample, each respective sample comprising a respective nucleic acid and a molecule that binds the respective nucleic acid to form a respective fluorescently detectable complex, and clustering genotypes of the plurality of nucleic acid samples to form a plurality of clusters of melting curves, wherein the clustering is hierarchically achieved upon assigning a distance between each pair of melting profiles.

2. The method according to claim 1 further comprising normalizing the raw melting curves.

3. The method of claim 2 wherein the distance assigned is based on a distance metric selected from the group consisting of: the maximal distance between curves, the average of the absolute value of the distance between curves at all temperature points, and the average of the root mean square of the distance between curves at all temperature points.

4. The method of claim 2 wherein the number of clusters is determined automatically by selecting a maximum ratio of distances between adjacent cluster levels.

5. The method of claim 4 wherein accuracy of the number of clusters is obtained by ordering the ratios of distances between each two adjacent cluster levels.

6. The method of claim 2 wherein a distance between clusters is determined as the minimum distance between any two curves in each cluster.

7. The method according to claim 2 wherein each respective raw melting curve comprises a respective background fluorescence signal and a respective nucleic acid sample signal, and the respective background signals are separated from the respective nucleic acid sample signals by use of an exponential algorithm to generate respective corrected melting curves, the respective corrected melting curves comprising the respective nucleic acid sample signals.

8. The method according to claim 7 wherein each respective background signal is calculated by fitting a decreasing exponential to a slope of a respective raw fluorescence versus temperature curve, wherein the decreasing exponential is fit to the respective melting curve profile through at least two slope values located on the respective melting curve profile where no sample melting occurs.

9. The method according to claim 7 wherein respective first and second slope values are used to derive each respective background signal, the respective first and second slope values taken from points on the respective raw melting curve where no sample nucleic acid melting occurs.

10. The method according to claim 9 wherein each respective background signal is calculated using the equation $e^{a(T_R-T_L)}=B'(T_R)/B'(T_L)$, wherein $a=(\ln(B'(T_R)/B'(T_L)))/(T_R-T_L)$, $B'(T_L)$ is the first slope value, and $B'(T_R)$ is the second slope value, and the background signal separation comprises using the equation $M(T)=F(T)-Ce^{a(T-T_L)}$, wherein $M(T)$ is the respective nucleic acid sample signal, $F(T)$ is the respective raw melting curve, and $C=B'(T_L)/a$.

11. The method according to claim 9 wherein each respective nucleic acid sample is a double-stranded product of a PCR reaction.

12. The method according to claim 9 wherein each respective melting profile comprises a melting transition for both a PCR product and an unlabeled probe.

13. The method according to claim 7 wherein each respective background fluorescence signal is calculated by fitting a respective decreasing exponential to a respective background fluorescence versus temperature curve, the respective decreasing exponential being derived from the respective first slope value taken from a point before the nucleic acid melting transition and the respective second slope value taken from a point after the nucleic acid melting transition.

14. The method according to claim 7 comprising measuring a respective first slope value and a respective second slope value of the respective raw melting curve or a derivative thereof, the respective first slope value and the respective second slope value obtained from a region of the respective raw melting curve not attributed to the sample melting, and using the respective first slope value and respective second slope value to find an exponential representative of background noise to separate a respective background signal from a respective nucleic acid sample signal.

15. The method according to claim 7 further comprising performing a difference function to identify differences between a corrected melting curve of a first one of the plurality of nucleic acid samples and a corrected melting curve of a second one of the plurality of nucleic acid samples.

16. The method according to claim 15 further comprising performing a curve overlay function with the corrected melting curve of said first one of the plurality of nucleic acid samples and the corrected melting curve of said second one of the plurality of nucleic acid samples, the curve overlay function requiring a single data point.

17. The method according to claim 2 wherein the distance between normalized curves is determined as an orthogonal metric.

18. The method according to claim 17 wherein the orthogonal metric is calculated by using the following equation: $f_1(T)-f_2(T)=\max\{\sqrt{(1+f_1'(T)^2)}, \sqrt{(1+f_2'(T)^2)}\}$.

19. A system for analyzing a plurality of nucleic acid samples comprising: an instrument for sequentially heating fluorescently detectable complexes while monitoring their fluorescence, each complex comprising a nucleic acid and a fluorescent species, the melting instrument being adapted to measure and to record sample temperature and sample fluorescence to determine sample fluorescence as a function of sample temperature to produce respective melting profiles of the respective fluorescently detectable complexes, each melting profile comprising a respective background fluorescence signal and a respective sample fluorescence signal; a central processing unit (CPU) for performing computer executable instructions; and a memory storage device for storing computer executable instructions that when executed by the CPU cause the CPU to cluster genotypes of a plurality of nucleic acid samples, the clustering being dynamically achieved by associating the distance between the sample melting curves.

20. The system according to claim 19 wherein the CPU performs clustering of genotypes of a plurality of double stranded nucleic acid samples, wherein the clustering is dynamically achieved by associating a minimum distance between the sample melting curves of distinct genotype clusters.

21. The system of claim 19 wherein the CPU for performing computer executable instructions and the memory storage device for storing computer executable instructions together comprise a CPU for performing computer executable instructions and the memory storage device for storing computer executable instructions that, when executed by the CPU, cause the CPU to analyze respective nucleic acids for sequence variations, the process including separating respective background fluorescence signals from respective melting profiles by an exponential algorithm to generate respective corrected melting curves, respective corrected melting curves comprising respective sample signals.

22. The system according to claim 21 wherein separating respective background fluorescence signals from respective melting profiles comprises measuring a first slope value and a second slope value of each respective melting profile, the first slope value and the second slope value of each respective melting profile obtained from a region of the respective melting profile not attributed to sample melting, the first slope value and the second slope value used to find an exponential function representative of the respective background fluorescence, the first slope value and second slope value taken from points on the respective melting profile with a temperature greater than $T_m$.

23. The system according to claim 22, wherein the respective exponential function is calculated using the equation $e^{a(T_R-T_L)}=B'(T_R)/B'(T_L)$, wherein $a=(\ln(B'(T_R)/B'(T_L)))/(T_R-T_L)$, $B'(T_L)$ is the respective first slope value, and $B'(T_R)$ is the respective second slope value, and the subtraction comprises using the equation $M(T)=F(T)-Ce^{a(T-T_L)}$, wherein $M(T)$ is the respective sample signal, $F(T)$ is the respective melting profile, and $C=B'(T_L)/a$.

24. The system according to claim 19 wherein the CPU normalizes the raw melting curves.

25. The system of claim 24 wherein clustering is based on a distance metric selected from the group consisting of: the maximal distance between curves, the average of the absolute value of the distance between curves at all temperature points, and the average of the root mean square of the distance between curves at all temperature points.

26. The system of claim 24 wherein the CPU determines the number of clusters by selecting a maximum ratio of distances between adjacent cluster levels.

27. The system of claim 26 wherein the CPU determines accuracy of the number of clusters by ordering the ratios of distances between two each adjacent cluster levels, to determine the largest ratio.

28. The system of claim 24 wherein the CPU determines a distance between clusters as the minimum distance between any two curves in each cluster.

29. A method of analyzing a plurality of nucleic acid sample melting plots comprising on at least one machine programmed for this purpose subjecting each of the melting plots to exponential background subtraction using the equation $e^{a(T_R-T_L)}=B'(T_R)/B'(T_L)$, wherein $a=(\ln(B'(T_R)/B'(T_L)))/(T_R-T_L)$, $B'(T_L)$ is a first slope value, and $B'(T_R)$ is a second slope value, and the subtraction comprises using the equation $M(T)=F(T)-Ce^{a(T-T_L)}$, wherein $M(T)$ is a sample signal, $F(T)$ is a signal function, and $C=B'(T_L)/a$.

30. A method of analyzing a plurality of nucleic acid sample melting plots comprising on at least one machine programmed for this purpose subjecting each of the melting plots to the curve overlay function and the plurality of melting plots are shifted by using the equation $$\min\_c \int_a^b ((f(z)+c)-g(z))2\,dz = \int_a^b g(z)-f(z)\,dz$$

wherein $f(z)$ and $g(z)$ represent sections between two normalized fluorescence values and c is a constant that makes the mean difference of $(x_1(y)+c)-x_2(y)$ equal to zero.

31. A method of analyzing a plurality of nucleic acid sample melting plots comprising on at least one machine programmed for this purpose subjecting each of the melting plots to the difference plot function, and difference between a first melting plot and a second melting plot of the plurality of melting plots is approximated using $f_1(T)-f_2(T)=\max\{\sqrt{(1+f_1'(T)^2)}, \sqrt{(1+f_2'(T)^2)}\}$.

32. A method of analyzing a plurality of nucleic acid sample melting plots comprising on at least one machine programmed for this purpose subjecting each of the melting plots to the clustering function, the clustering function having a mathematical representation $\min\_\{f_1 \epsilon C_1, f_2 \epsilon C_2\}$, wherein $\|f_1-f_2\|$, further wherein $f_1$ represents a melting curve associated with subcluster $C_1$ to generate a plurality of clusters of melting plots.

33. A method of analyzing a plurality of nucleic acid sample melting plots comprising on at least one machine programmed for this purpose subjecting each of the melting plots to the exponential background subtraction, the method further performing on said at least one machine programmed for this purpose the curve overlay function, the difference plot function, and the clustering function.

34. A method for clustering melting profiles of a plurality of nucleic acid samples, comprising measuring the fluorescence of each nucleic acid sample as a function of temperature to produce a respective raw melting curve for each respective nucleic acid sample, each respective sample comprising a respective nucleic acid and a molecule that binds the respective nucleic acid to form a respective fluorescently detectable complex, normalizing the raw melting curves and genotyping the plurality of nucleic acid samples by unbiased hierarchal clustering by forming a plurality of clusters of the melting curves wherein each cluster represents a genotype.

35. A system for analyzing a plurality of curves each represented as a signal function comprising: an instrument comprising a central processing unit (CPU) for performing computer executable instructions; and a memory storage device for storing computer executable instructions that when executed by the CPU cause the CPU to cluster the plurality of curves, the clustering being hierachically achieved upon assigning a distance between each pair of signal functions.

36. The method of claim 35 wherein the distance is based on a distance metric selected from the group consisting of: the maximal distance between curves, the average of the absolute value of the distance between curves at all temperature points, and the average of the root mean square of the distance between curves at all temperature points.

* * * * *